United States Patent
Studer et al.

(10) Patent No.: US 11,326,148 B2
(45) Date of Patent: May 10, 2022

(54) METHODS OF DIFFERENTIATING STEM CELL-DERIVED ECTODERMAL LINEAGE PRECURSORS

(71) Applicant: MEMORIAL SLOAN-KETTERING CANCER CENTER, New York, NY (US)

(72) Inventors: Lorenz Studer, New York, NY (US); Bastian Zimmer, Lindenberg im Allgaeu (DE); Jason Tchieu, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 427 days.

(21) Appl. No.: 16/054,071

(22) Filed: Aug. 3, 2018

(65) Prior Publication Data

US 2019/0071643 A1 Mar. 7, 2019

Related U.S. Application Data

(63) Continuation of application No. PCT/US2017/016723, filed on Feb. 6, 2017.

(60) Provisional application No. 62/350,032, filed on Jun. 14, 2016, provisional application No. 62/299,361, filed on Feb. 24, 2016, provisional application No. 62/292,014, filed on Feb. 5, 2016.

(51) Int. Cl.
| | |
|---|---|
| *C12N 5/0775* | (2010.01) |
| *C12N 5/0793* | (2010.01) |
| *C12N 5/079* | (2010.01) |
| *C12N 5/00* | (2006.01) |
| *C12N 5/0735* | (2010.01) |
| *C12N 5/074* | (2010.01) |
| *A61K 35/12* | (2015.01) |

(52) U.S. Cl.
CPC ......... *C12N 5/0667* (2013.01); *C12N 5/0018* (2013.01); *C12N 5/0606* (2013.01); *C12N 5/0618* (2013.01); *C12N 5/0619* (2013.01); *C12N 5/0696* (2013.01); *A61K 35/12* (2013.01); *C12N 2501/01* (2013.01); *C12N 2501/115* (2013.01); *C12N 2501/155* (2013.01); *C12N 2501/16* (2013.01); *C12N 2501/727* (2013.01); *C12N 2501/999* (2013.01); *C12N 2506/02* (2013.01); *C12N 2506/03* (2013.01); *C12N 2506/04* (2013.01); *C12N 2510/00* (2013.01); *C12N 2533/52* (2013.01)

(58) Field of Classification Search
CPC .............. C12N 5/0619; C12N 5/0618; C12N 2506/02; C12N 2506/03; C12N 2506/04; C12N 2506/45
See application file for complete search history.

(56) References Cited

U.S. PATENT DOCUMENTS

| | | | | |
|---|---|---|---|---|
| 10,053,667 B2 * | 8/2018 | Dalton | ................ | C12N 5/0623 |
| 10,160,950 B2 * | 12/2018 | Zhang | ................ | C12N 5/0619 |
| 10,273,452 B2 * | 4/2019 | Chambers | ............... | A61P 25/00 |
| 2008/0268019 A1 | 10/2008 | Badylak et al. | | |
| 2009/0123433 A1 | 5/2009 | Shroff | | |
| 2011/0296542 A1 | 12/2011 | Wang et al. | | |
| 2013/0183674 A1 * | 7/2013 | Studer | ................ | C12N 5/0618 435/6.12 |
| 2013/0280804 A1 * | 10/2013 | Dalton | ................ | C12N 5/0623 435/368 |
| 2015/0159135 A1 | 6/2015 | Davis et al. | | |
| 2018/0291339 A1 * | 10/2018 | Studer | ..................... | A61P 1/00 |
| 2018/0346875 A1 * | 12/2018 | Qi | ................... | A61P 25/28 |
| 2021/0123018 A1 * | 4/2021 | Studer | .................... | A61K 35/30 |

FOREIGN PATENT DOCUMENTS

| | | |
|---|---|---|
| WO | WO 2010/096496 A2 | 8/2010 |
| WO | WO 2011/149762 A2 | 12/2011 |
| WO | WO 2012/103012 A1 | 8/2012 |
| WO | WO 2013/067362 A1 | 5/2013 |
| WO | WO 2013/166488 A1 | 11/2013 |
| WO | WO 2014/176606 A1 | 10/2014 |
| WO | WO 2015/077648 A1 | 5/2015 |
| WO | WO 2017/136834 A1 | 8/2017 |

OTHER PUBLICATIONS

Kim et al. Neuron 38:17-31, 2003 (Year: 2003).*
Menendez et al., "Wnt signaling and a Smad pathway blockade direct the differentiation of human pluripotent stem cells to multipotent neural crest cells," PNAS 108(48):19240-19245 (2011).
Steinbeck et al., "Moving Stem Cells to the Clinic: Potential and Limitations for Brain Repair," Neuron 86(1):187-206 (2015).
Supplementary European Search Report dated Jun. 28, 2019 in Application No. EP 17748353.
Anders et al., "Differential expression analysis for sequence count data," Genome Biology 11:R106 (2010). throughput sequencing data," Bioinformatics 31(2):166-169 (2015).
Bailey et al., "Lens Specification is the Ground State of All Sensory Placodes, from which FGF Promotes Olfactory Identity," Developmental Cell 11:505-517 (2006).
Bansal et al., "Specific Inhibitor of FGF Receptor Signaling: FGF-2-Mediated Effects on Proliferation, Differentiation, and MAPK Activation Are Inhibited by PD173074 in Oligodendrocyte Lineage Cells," J. Neurosci. Res., 74:486-493 (2003).

(Continued)

*Primary Examiner* — Marcia S Noble
(74) *Attorney, Agent, or Firm* — Baker Botts L.L.P.

(57) ABSTRACT

The presently disclosed subject matter provides for in vitro methods of inducing differentiation of human stem cells into neural crest, cranial placode or non-neuro ectoderm precursors, and cells generated by such methods. The presently disclosed subject matter also provides for uses of such cells for treating neurodegenerative and pituitary disorders.

10 Claims, 60 Drawing Sheets

Specification includes a Sequence Listing.

(56) References Cited

OTHER PUBLICATIONS

Anders et al., "HTSeq—a Python framework to work with high-
Cadigan et al., "Wnt signaling: complexity at the surface," J Cell Sci. 119:395-402 (2006).
Calder et al., "Retinoic Acid-Mediated Regulation of GLI3 Enables Efficient Motoneuron Derivation from Human ESCs in the Absence of Extrinsic SHH Activation," J Neurosci. 35(33):11462-11481 (2015).
Cermak et al., "Efficient design and assembly of custom TALEN and other TAL effector-based constructs for DNA targeting," Nucleic Acids Research 39(12):e82 (2011).
Chambers et al., "Highly efficient neural conversion of human ES and iPS cells by dual inhibition of SMAD signaling," Nature Biotechnology 27(3):275-280 (2009).
Chambers et al., "Combined small-molecule inhibition accelerates developmental timing and converts human pluripotent stem cells into nociceptors," Nature Biotechnology 30(7):715-720 (2012).
Chemaitilly et al., "Endocrine complications in long-term survivors of childhood cancers," Endocrine-Related Cancer 17:R141-159 (2010).
Chen et al., "Chemically defined conditions for human iPSC derivation and culture," Nat Methods 8(5):424-429 (2011).
Cong et al., "Multiplex Genome Engineering Using CRISPR/Cas Systems," Science 339:819-823 (2013).
Dincer et al., "Specification of Functional Cranial Placode Derivatives from Human Pluripotent Stem Cells," Cell Reports 5:1387-1402 (2013).
Doble et al., "GSK-3: Tricks of The Trade for A Multi-Tasking Kinase," J Cell Sci. 116:1175-1186 (2003).
Doyle et al., "TAL Effector-Nucleotide Targeter (TALE-NT) 2.0: tools for TAL effector design and target prediction," Nucleic Acids Research 40:W117-W122 (2012).
Dreser et al., "Grouping of histone deacetylase inhibitors and other toxicants disturbing neural crest migration by transcriptional profiling," Neurotoxicology 50:56-70 (2015).
Edgar et al., "LifeMap Discovery™: The Embryonic Development, Stem Cells, and Regenerative Medicine Research Portal," PLoS ONE 8(7):e66629 (2013).
Ezzat et al., "The Prevalence of Pituitary Adenomas: A Systematic Review," Cancer 101(3):613-619 (2004).
Groves et al., "Setting appropriate boundaries: Fate, patterning and competence at the neural plate border," Developmental Biology 389:2-12 (2014).
Huang et al., "Discovery of 3-[2-(Imidazo[1,2-b]pyridazin-3-yl)ethynyl]-4-methyl-N-{4-[(4-methylpiperazin-1-yl)-methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant," J. Med. Chem., 53:4701-4719 (2010).
International Search Report and Written Opinion dated Nov. 30, 2018 in International Application No. PCT/US18/49986.
International Search Report dated Jun. 9, 2017 in International Application No. PCT/US17/16723.
Kikuchi et al., "Multiplicity of the interactions of Wnt proteins and their receptors," Cell Signaling 19:659-671 (2007).
Lamolet et al., "A Pituitary Cell-Restricted T Box Factor, Tpit, Activates POMC Transcription in Cooperation with Pitx Homeoproteins," Cell 104:849-859 (2001).
Leung et al., "Differential BMP signaling controls formation and differentiation of multipotent preplacodal ectoderm progenitors from human embryonic stem cells," Developmental Biology 379:208-220 (2013).
Li et al., "Redundant activities of Tfap2a and Tfap2c are required for neural crest induction and development of other non-neural ectoderm derivatives in zebrafish embryos," Developmental Biology 304:338-354 (2007).
Lippmann et al., "Defined Human Pluripotent Stem Cell Culture Enables Highly Efficient Neuroepithelium Derivation without Small Molecule Inhibitors," Stem Cells 32:1032-1042 (2014).
Luo et al., "Induction of neural crest in Xenopus by transcription factor AP2α," PNAS 100(2):532-537 (2003).
Mali et al., "RNA-Guided Human Genome Engineering via Cas9," Science 339:823-826 (2013).
Maroof et al., "Directed Differentiation and Functional Maturation of Cortical Interneurons from Human Embryonic Stem Cells," Cell Stem Cell 12:559-572 (2013).
Merkle et al., "Generation of neuropeptidergic hypothalamic neurons from human pluripotent stem cells," Development 142:633-643 (2015).
Mica et al., "Modeling Neural Crest Induction, Melanocyte Specification, and Disease-Related Pigmentation Defects in hESCs and Patient-Specific iPSCs," Cell Reports 3:1140-1152 (2013).
Murry et al., "Differentiation of Embryonic Stem Cells to Clinically Relevant Populations: Lessons from Embryonic Development," Cell 132:661-680 (2008).
Panek et al., "In Vitro Pharmacological Characterization of PD 166285, a New Nanomolar Potent and Broadly Active Protein Tyrosine Kinase Inhibitor," J Pharmacol Exp Ther. 283(3):1433-1444 (1997).
Paterson et al., "Preclinical studies of fibroblast growth factor receptor 3 as a therapeutic target in multiple myeloma," Br. J. Haematol. 124:595-603 (2004).
Regal et al., "Prevalence and incidence of hypopituitarism in an adult Caucasian population in northwestern Spain," Clinical Endocrinology 55:735-740 (2001).
Rosenfeld et al., "Multistep signaling and transcriptional requirements for pituitary organogenesis in vivo," Recent Progress in Hormone Research 55:1-13 (2000).
Schorle et al., "Transcription factor AP-2 essential for cranial closure and craniofacial development," Nature 381:235-238 (1996).
Sklar et al., "Chronic Neuroendocrinological Sequelae of Radiation Therapy," Int. J. Radiation Oncology Biol. Phys. 31(5):1113-1121 (1995).
Smith, "Hormone replacement therapy in hypopituitarism," Expert Opinion on Pharmacotherapy 5(5):1023-1031 (2004).
Smith et al., "The role of the hypothalamic-pituitary-adrenal axis in neuroendocrine responses to stress," Dialogues Clin Neurosci. 8:383-395 (2006).
Stanton et al., "Small-molecule modulators of the Sonic Hedgehog signaling pathway," Mol. Biosyst. 6:44-54 (2010).
Steinbeck et al., "Functional Connectivity under Optogenetic Control Allows Modeling of Human Neuromuscular Disease," Cell Stem Cell 18:134-143 (2016).
Suga et al., "Self-formation of functional adeno-hypophysis in three-dimensional culture," Nature 480:57-62 (2011).
Sun et al., "Design, Synthesis, and Evaluations of Substituted 3-[(3- or 4-Carboxyethylpyrrol-2-yl) methylidenyl] indolin-2-ones as Inhibitors of VEGF, FGF, and PDGF Receptor Tyrosine Kinases," Journal of Medicinal Chemistry 42:5120-5130 (1999).
Tabar, "Making a Pituitary Gland in a Dish," Cell Stem Cell 9:490-491 (2011).
Takahashi et al., "Induction of Pluripotent Stem Cells from Mouse Embryonic and Adult Fibroblast Cultures by Defined Factors," Cell 126:663-676 (2006).
Tanaka et al., "FGF-induced vesicular release of Sonic hedgehog and retinoic acid in leftward nodal flow is critical for left-right determination," Nature 435:172-177 (2005).
Van Gelderen et al., "Familial isolated growth hormone deficiency," Clinical Genetics 20:173-175 (1981).
Villalobos et al., "Phenotypic characterization of multi-functional somatotropes, mammotropes and gonadotropes of the mouse anterior pituitary," Pflugers Arch—Eur J Physiol 449:257-264 (2004).
Wand, "The Influence of Stress on the Transition from Drug Use to Addiction," Alcohol Res Health 31(2):119-136 (2008).
Webster et al., "Role of the hypothalamic-pituitary-adrenal axis, glucocorticoids and glucocorticoid receptors in toxic sequelae of exposure to bacterial and viral products," J Endocrinol 181:207-221 (2004).
Zhou et al., "A Structure-Guided Approach to Creating Covalent FGFR Inhibitors," Chem & Biol., 17:285-295 (2010).

(56) References Cited

OTHER PUBLICATIONS

Zhu et al., "Molecular Physiology of Pituitary Development: Signaling and Transcriptional Networks," Physiol Rev 87:933-963 (2007).
Zimmer et al., "Evaluation of Developmental Toxicants and Signaling Pathways in a Functional Test Based on the Migration of Human Neural Crest Cells," Environ Health Perspect 120:1116-1122 (2012).
Leung et al., "WNT/β-catenin signaling mediates human neural crest induction via a pre-neural border intermediate," Development, 143(3):398-410 (2016).
Blauwkamp et al., "Endogenous Wnt signalling in human embryonic stem cells generates an equilibrium of distinct lineage-specified progenitors," Nature Communications 3:1070 (2012).
Chen, "Splitting hESC/hiPSC lines with EDTA in feeder free conditions," (Dec. 10, 2012), StemBook, ed. The Stem Cell Research Community, StemBook, doi/10.3824/stembook.1.88.1, http://www.stembook.org.
Hamby et al., "Structure-Activity Relationships for a Novel Series of Pyrido[2,3-d]pyrimidine Tyrosine Kinase Inhibitors," J Med Chem. 40:2296-2303 (1997).
Lee et al., "Large-scale screening using familial dysautonomia induced pluripotent stem cells identifies compounds that rescue IKBKAP expression," Nature Biotechnology 30(12):1244-1248 (2012).
Livak et al., "Analysis of Relative Gene Expression Data Using Real-Time Quantitative PCR and the 2(-ΔΔC(T)) Method," Methods 25:402-408 (2001).
Morrison et al., "Transient Notch Activation Initiates an Irreversible Switch from Neurogenesis to Gliogenesis By Neural Crest Stem Cells," Cell 101:499-510 (2000).
Nunez et al., "Multifunctional cells of mouse anterior pituitary reveal a striking sexual dimorphism," J Physiol 549.3:83 5-843 (2003).
Rivera, "Lymphocytic hypophysitis: Disease spectrum and approach to diagnosis and therapy," Pituitary 9:35-45 (2006).
Sanjana et al., "A transcription activator-like effector toolbox for genome engineering," Nature Protocols 7(1):171-192 (2012).
Szarek et al., "Hypothalamic input is required for development of normal numbers of thyrotrophs and gonadotrophs, but not other anterior pituitary cells in late gestation sheep," J Physiol 586.4:1185-1194 (2008).
Trapnell et al., "Differential gene and transcript expression analysis of RNA-seq experiments with TopHat and Cufflinks," Nature Protocols 7(3):562-578 (2012).
Xie et al., "Regulation of the Mouse Cartilage-derived Retinoic Acid-sensitive Protein Gene by the Transcription Factor AP-2," The Journal of Biological Chemistry 273(9):5026-5032 (1998).
Yamamoto et al., "TSU68 Prevents Liver Metastasis of Colon Cancer Xenografts by Modulating the Premetastatic Niche," Cancer Res 68(23):9754-9762 (2008).

* cited by examiner

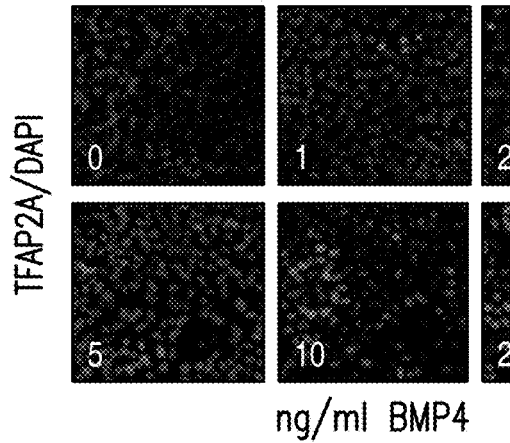
FIG. 2A
FIG. 2B
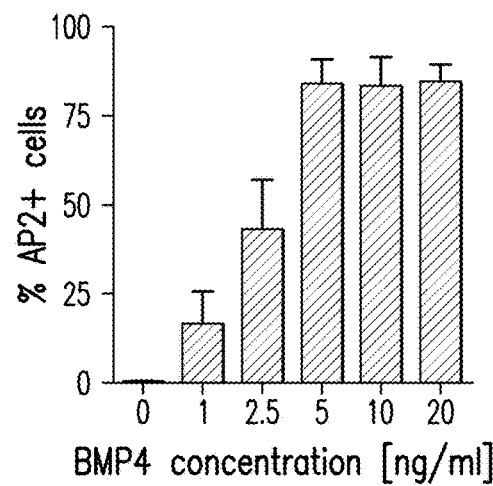
FIG. 2C
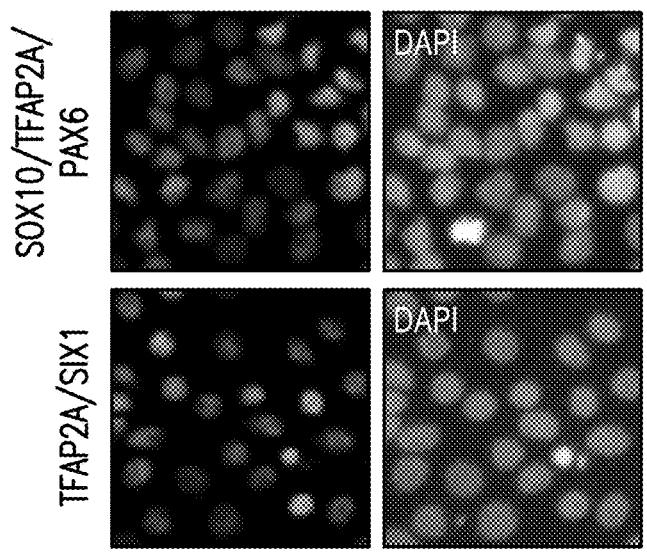
FIG. 2D
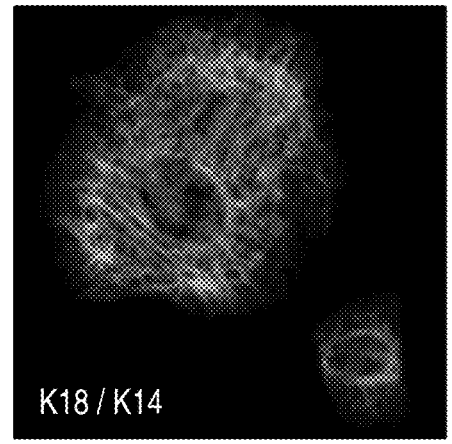
FIG. 2E

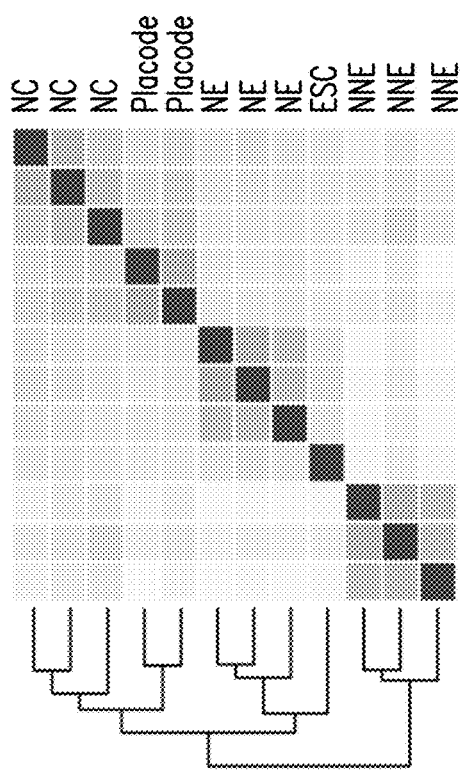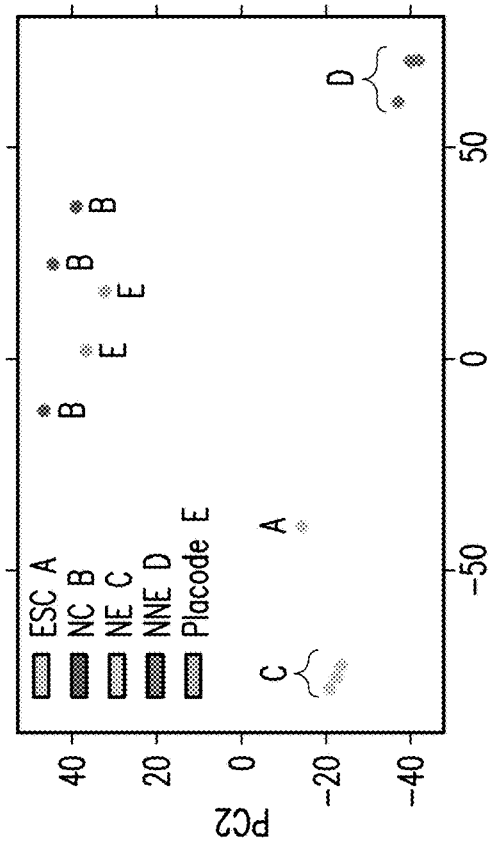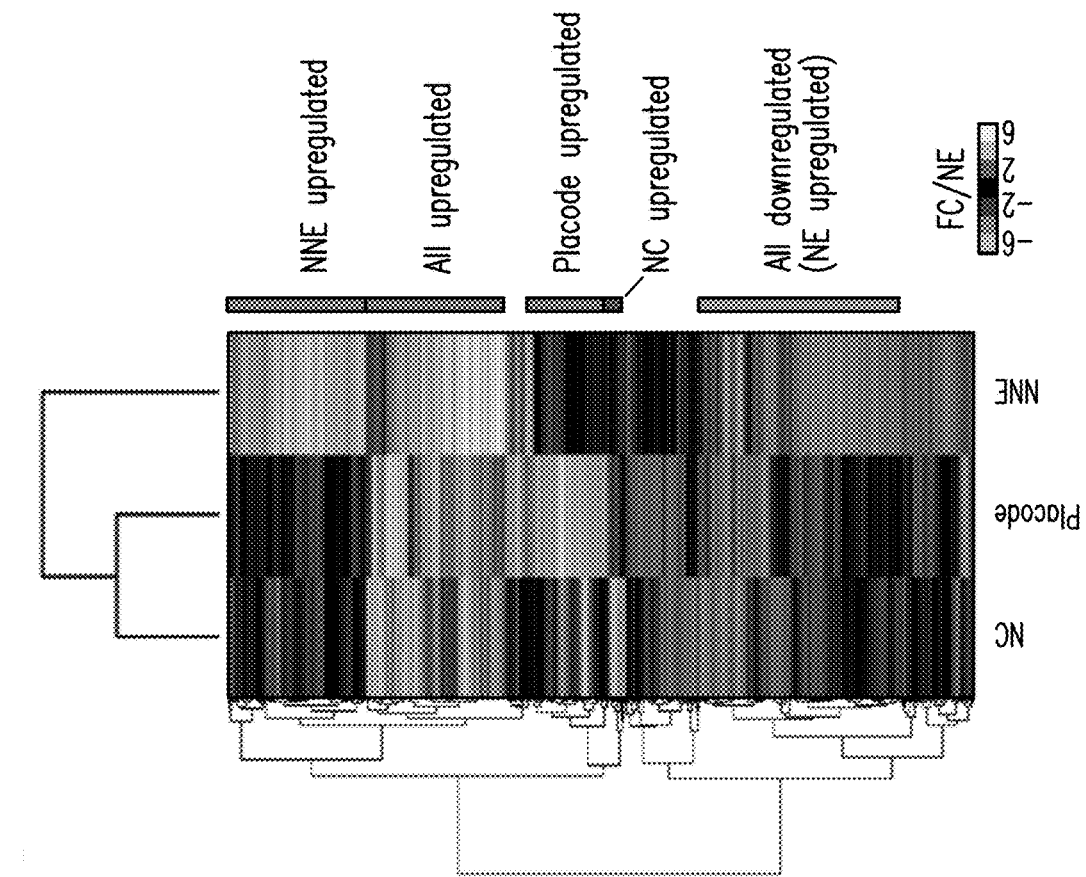
FIG. 4A
FIG. 4B
FIG. 4C

| Enriched GO Terms: | | p-value |
|---|---|---|
| All upregulated: | Extracellular matrix organization | $2.4 \times 10^{-15}$ |
| | RNA PolII transcription activity | $3.2 \times 10^{-15}$ |
| NC upregulated: | Calcium ion binding | $2.0 \times 10^{-14}$ |
| | Cell adhesion | $2.7 \times 10^{-07}$ |
| Placode upregulated: | Synaptic transmission | $6.4 \times 10^{-15}$ |
| | Ion membrane transport | $2.1 \times 10^{-07}$ |
| NNE upregulated: | Small molecule metabolic process | $2.8 \times 10^{-14}$ |
| | Negative regulation of proliferation | $1.6 \times 10^{-13}$ |
| | Extracellular matrix organization | $8.0 \times 10^{-10}$ |
| All downregulated: | Synaptic transmission | $1.0 \times 10^{-16}$ |
| | Nervous system development | $1.9 \times 10^{-10}$ |

FIG. 4D

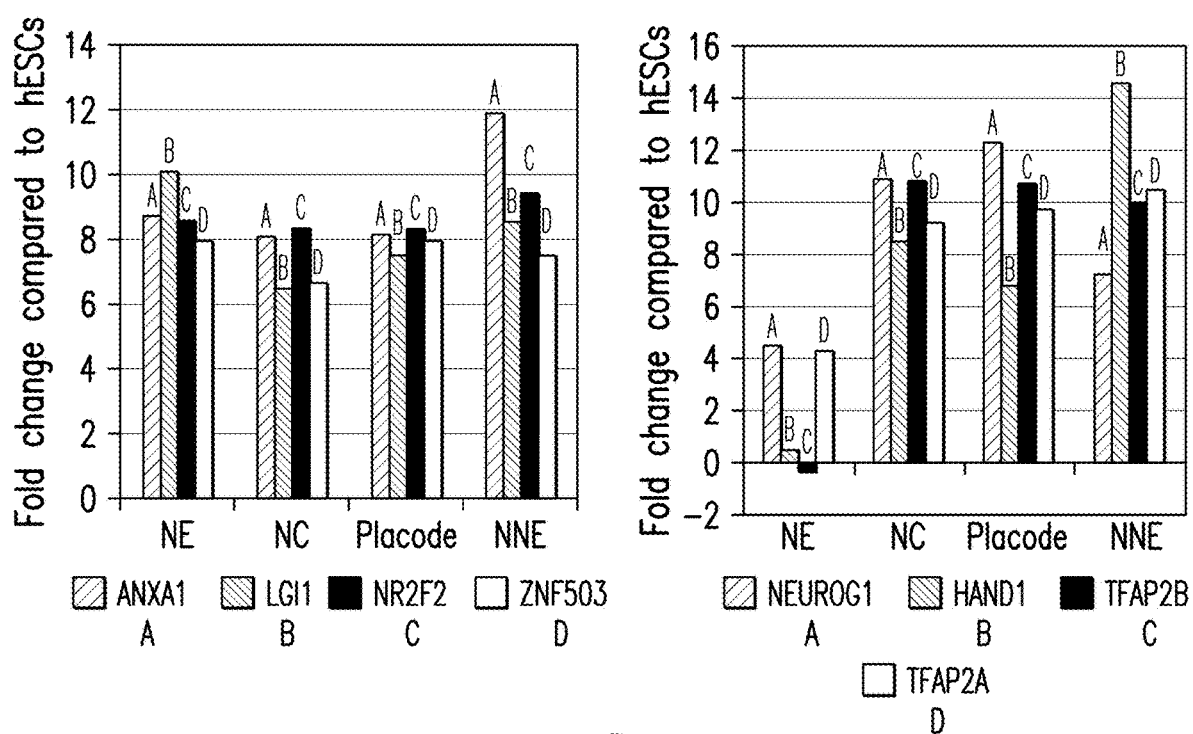

FIG. 4E

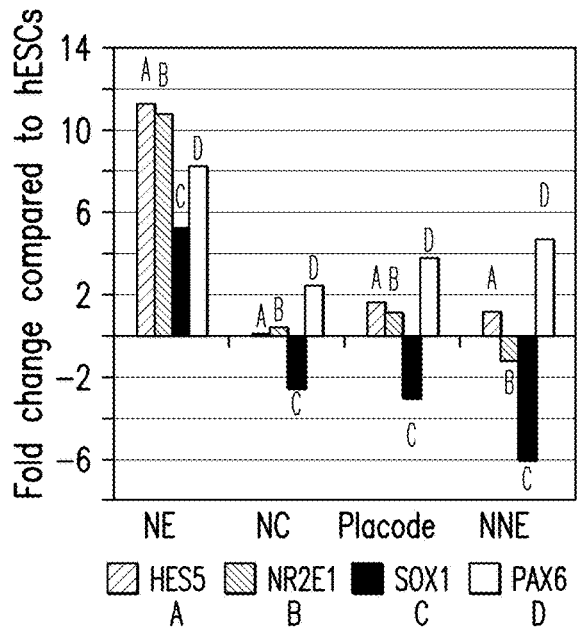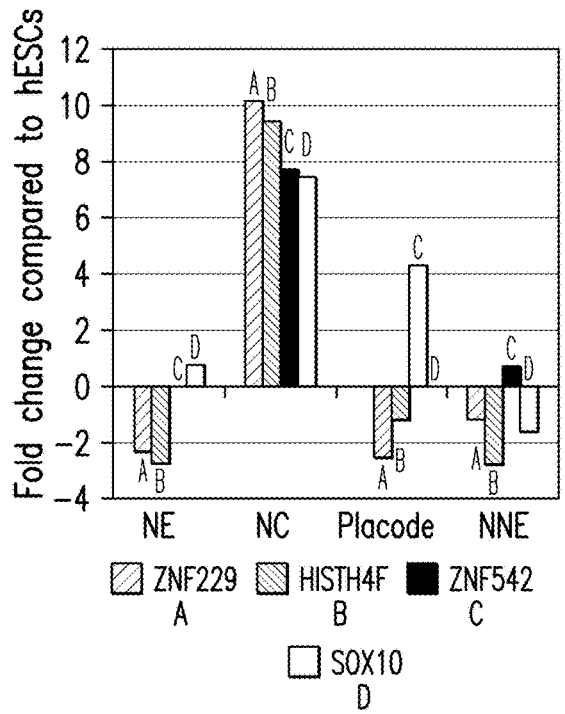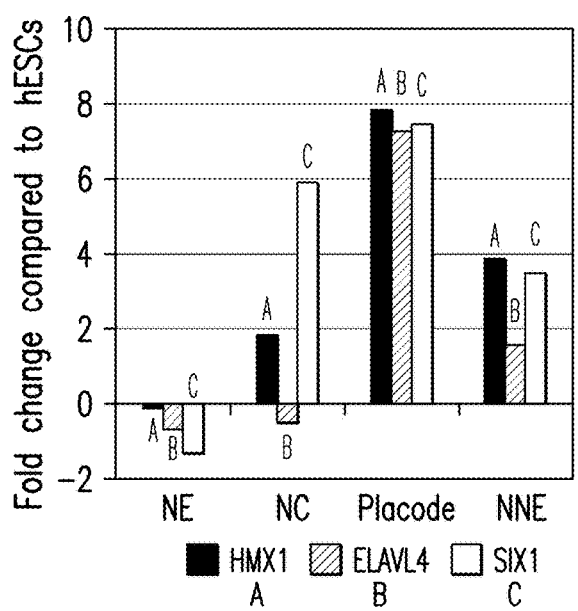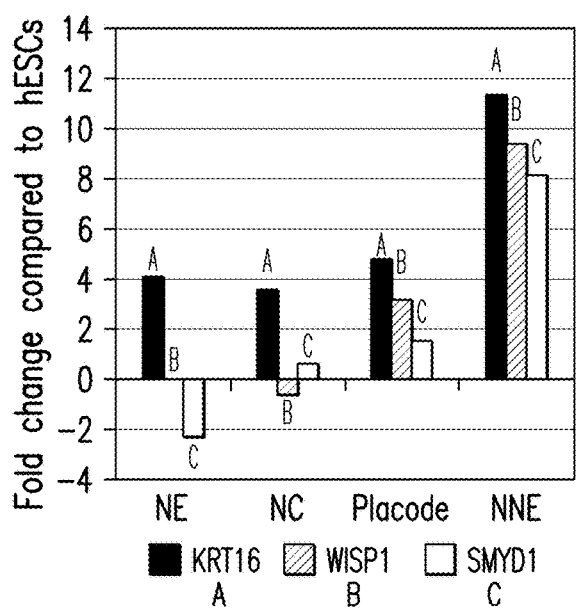
FIG. 4F

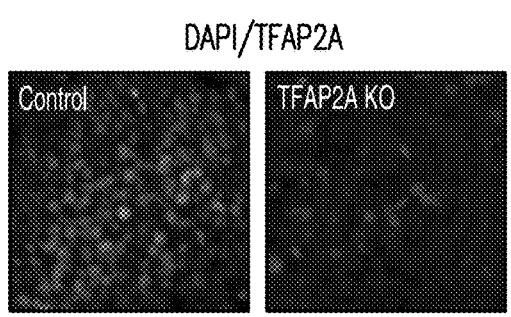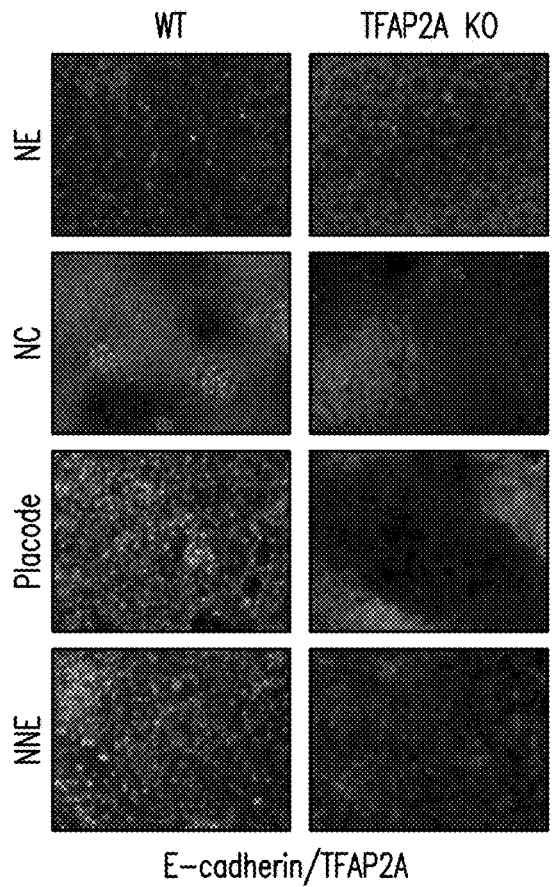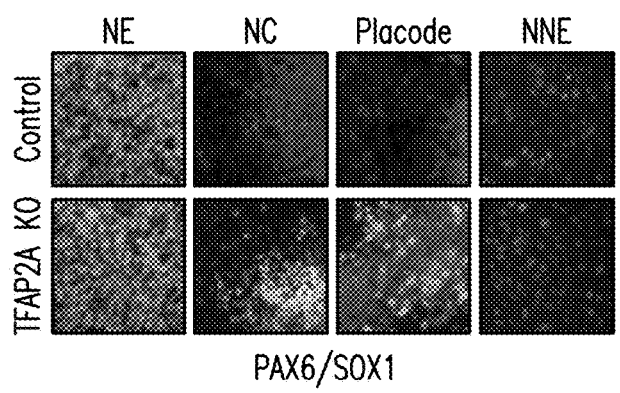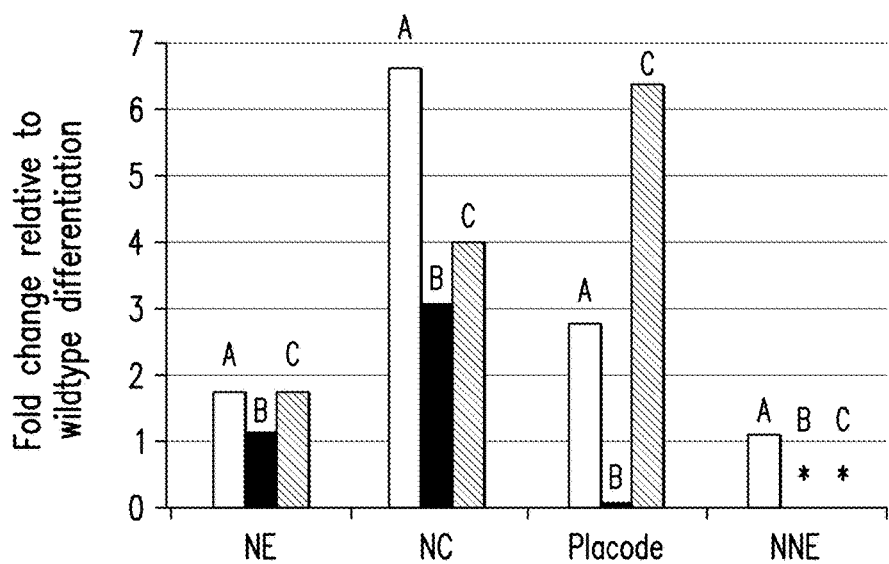

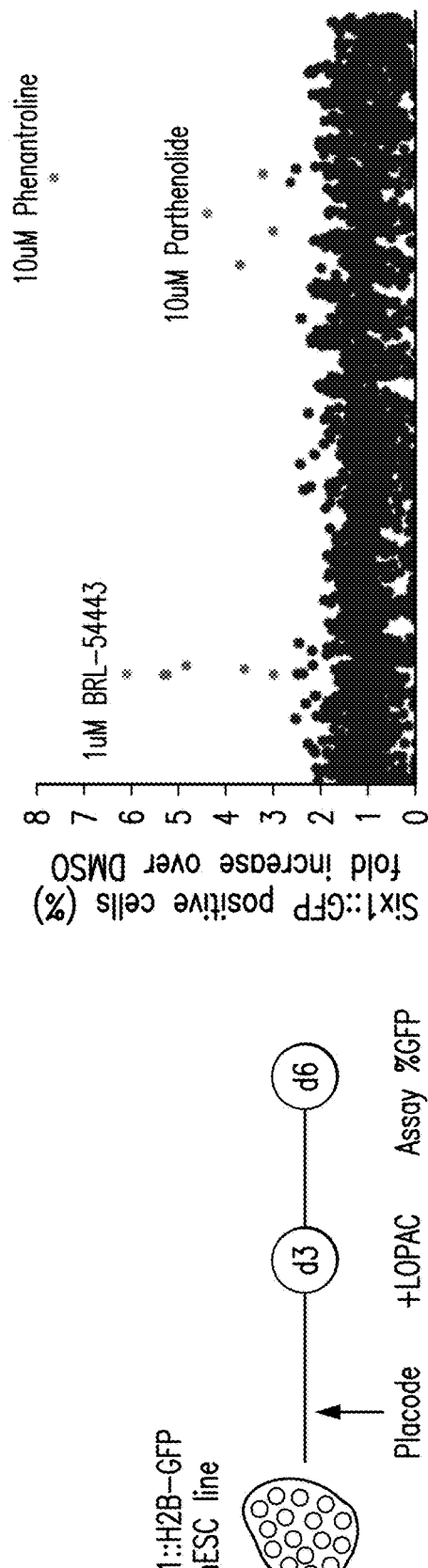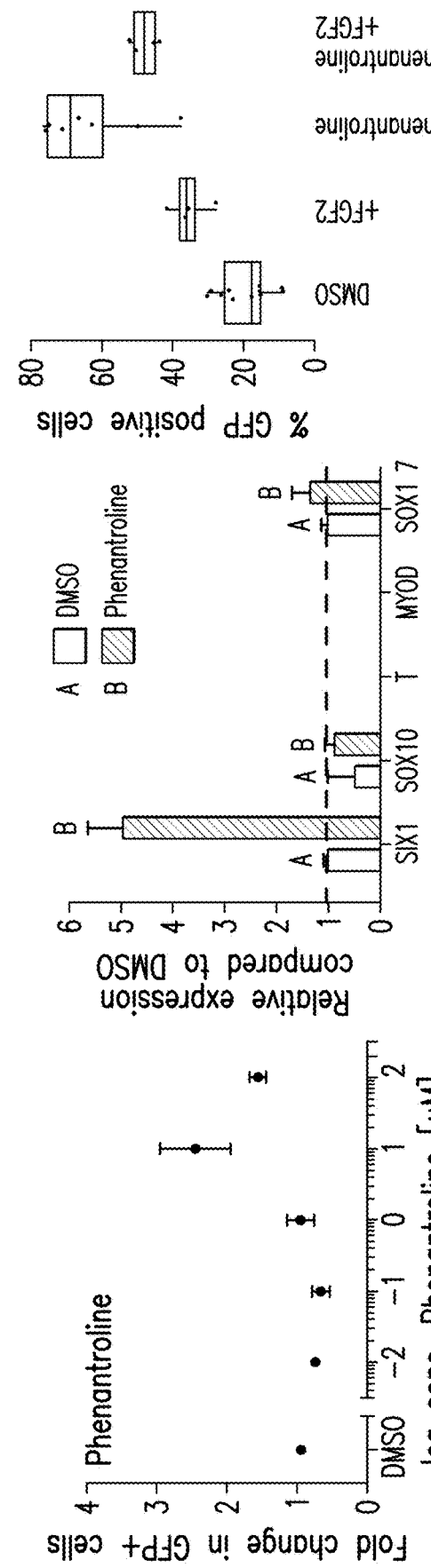

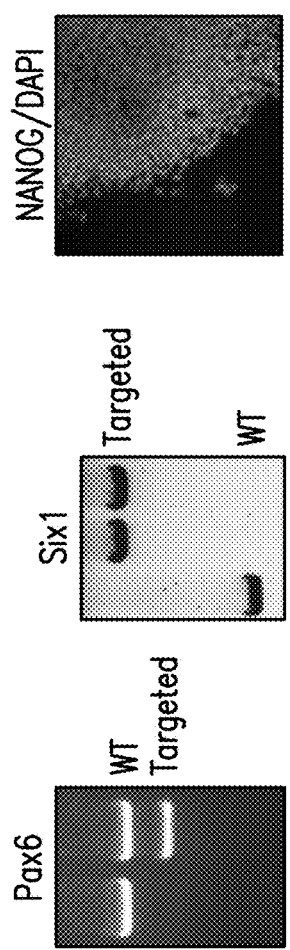
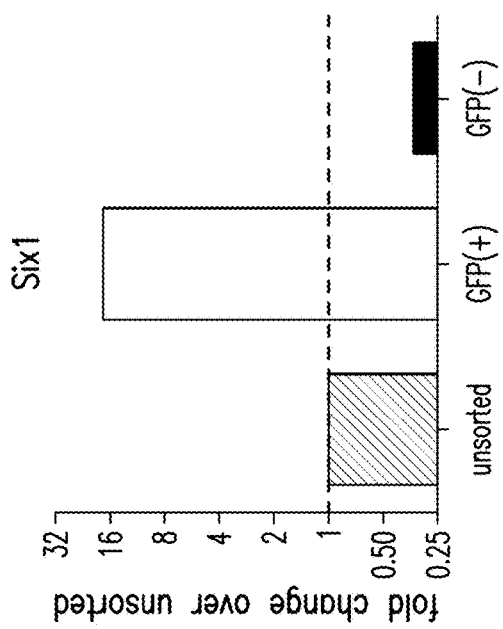
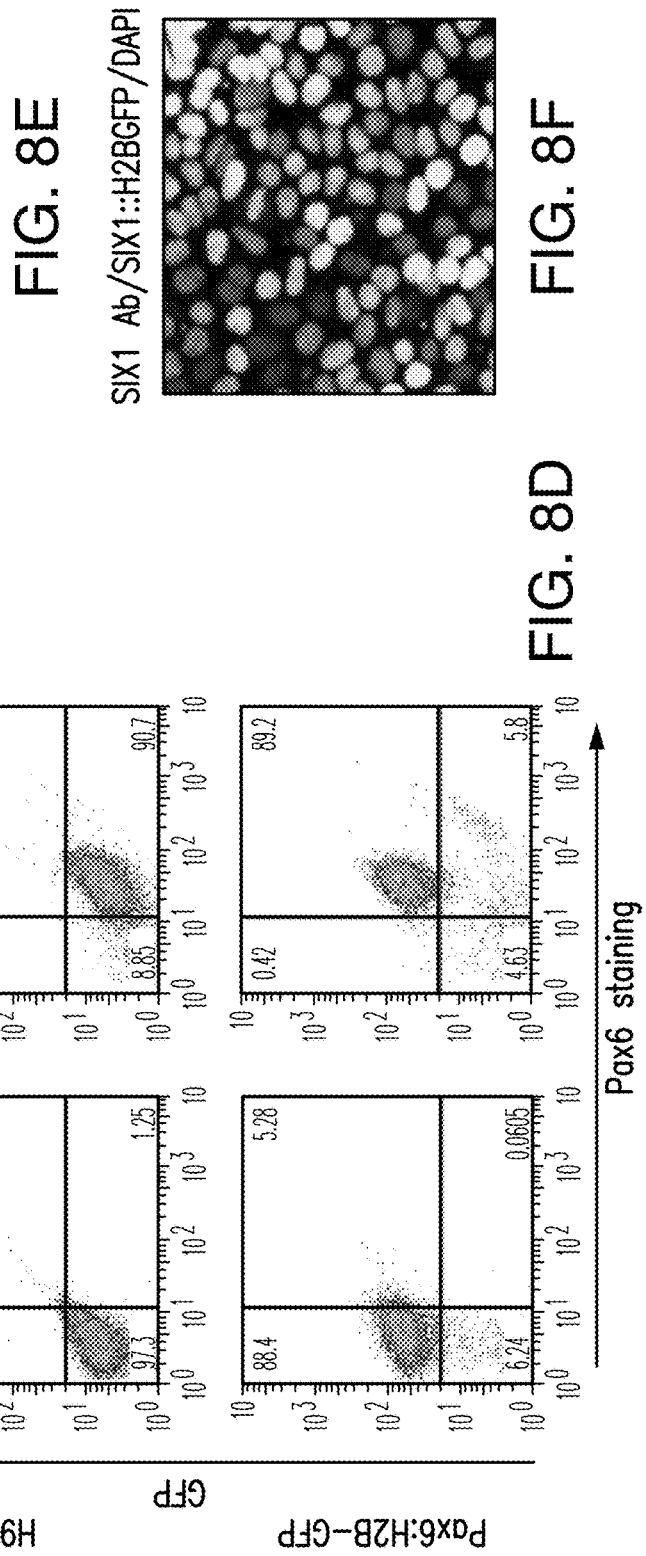
FIG. 8B
FIG. 8C
FIG. 8E
FIG. 8F
FIG. 8D

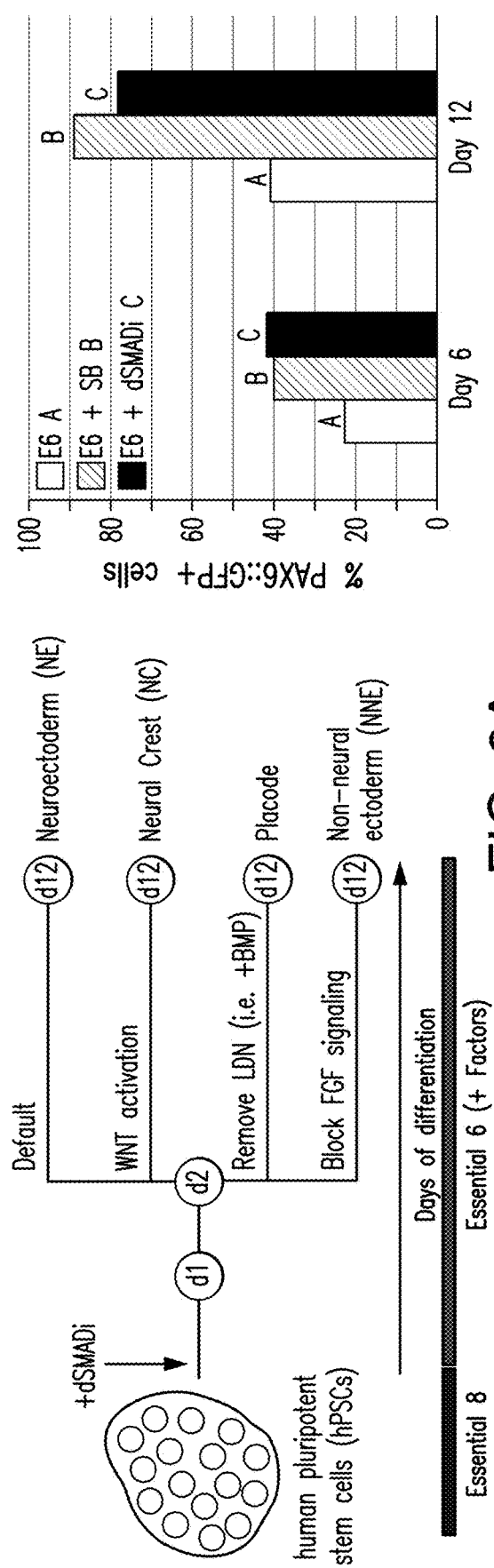
FIG. 9A
FIG. 9B
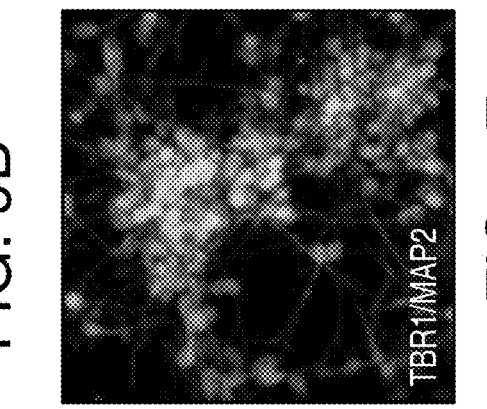
FIG. 9E
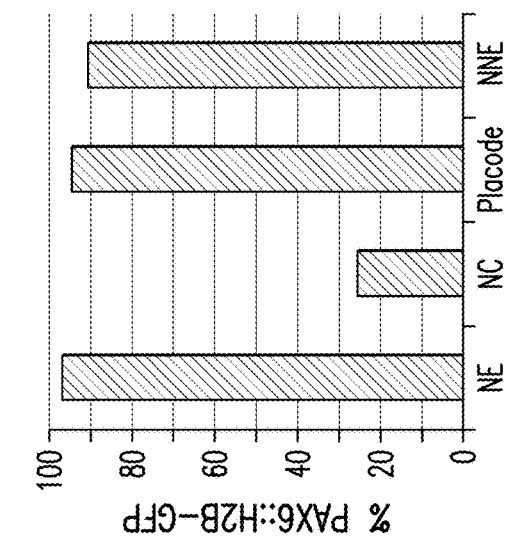
FIG. 9D
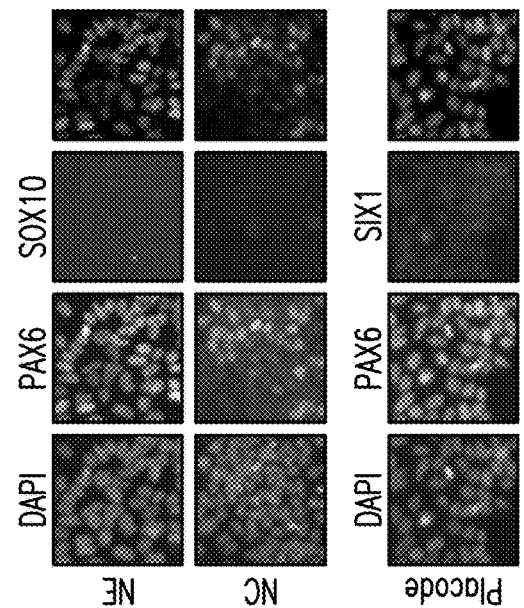
FIG. 9C

```
                              TACCAGCCTATCTACCCCCAGTCGCAAGATCCTTACTCCCACGTCAACGACCCCTACAG    SEQ ID NO: 1
                                       AP2A-88 →
                                                  ← AP2A-92
                                          FIG. 12A

B1                   B1    7   ACCCTACCAGCCTATCTACCCCCAGTCGCAAGATCCTTACTCCCACGTCAACGACCCCTA    66   SEQ ID NO: 2
no deletion/SNP      UCSC  61  ACCCTACCAGCCTATCTACCCCCAGTCGCAAGATCCTTACTCCCACGTCAACGACCCCTA   120

AP2A.4               H9_wt 6   CACCCTACCAGCCTATCTACCCCCAG----TC--GCAAGATCCTTACTCCCACGTCAACG    59   SEQ ID NO: 3
Δ5bp                 AP2_4 61  CACCCTACCAGCCTATCTACCCCCAGNATAGNGGGCAAGACCCTTACTCCTACGTCCTGA   120   SEQ ID NO: 4
D71X

AP2A.10              H9_wt 5   CCACCCTACCAGCCTATCTACCCCCAGTCGCAAGATCCTTACTCCCACGTCAACGACCCC    64   SEQ ID NO: 5
Δ18bp                AP2_10 61 CCACCCTACCAGCCTATCTACCCC------------------TCCNAGGTAAACAACCCC   102   SEQ ID NO: 6
Q70X

AP2A.11              H9_wt 9   CCTACCAGCCTATCTACCCCCAGTCGCAAGATCCTTACTCCCACGTCAACGACCCCTACA    68   SEQ ID NO: 7
Δ10bp                AP2_11 61 CCTACCAGCCTATCTACCCCCAGT----------TTACACCCATATCCACGACCCCTACA   110   SEQ ID NO: 8
V159X

FIG. 12B
```

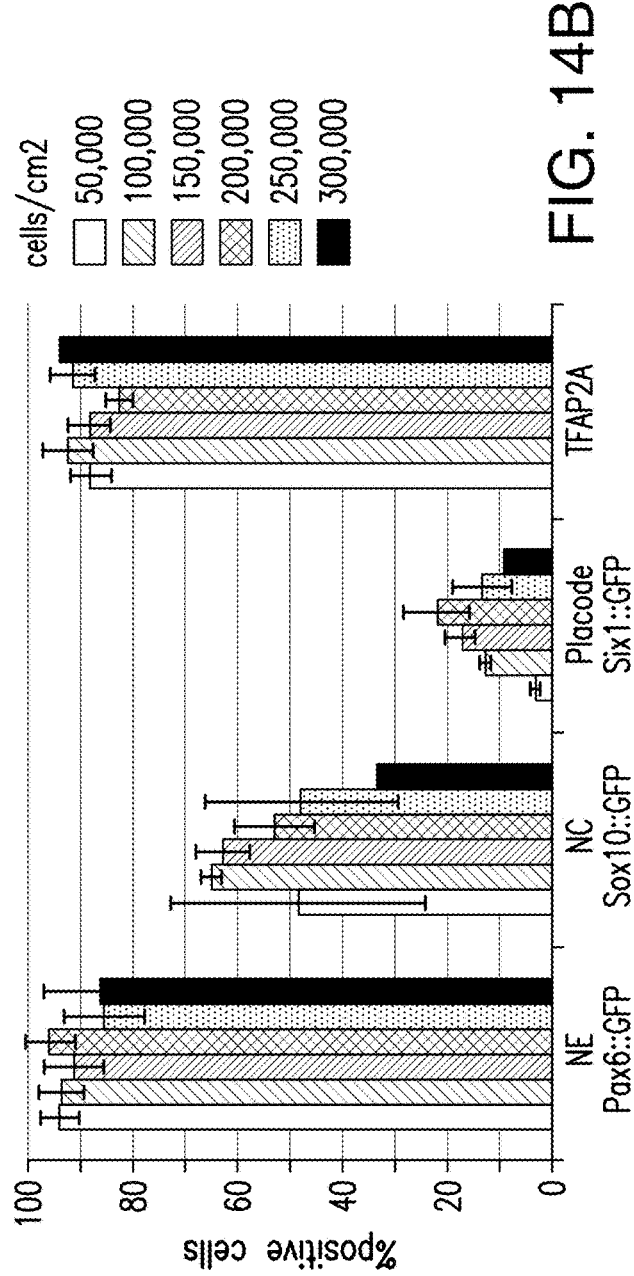
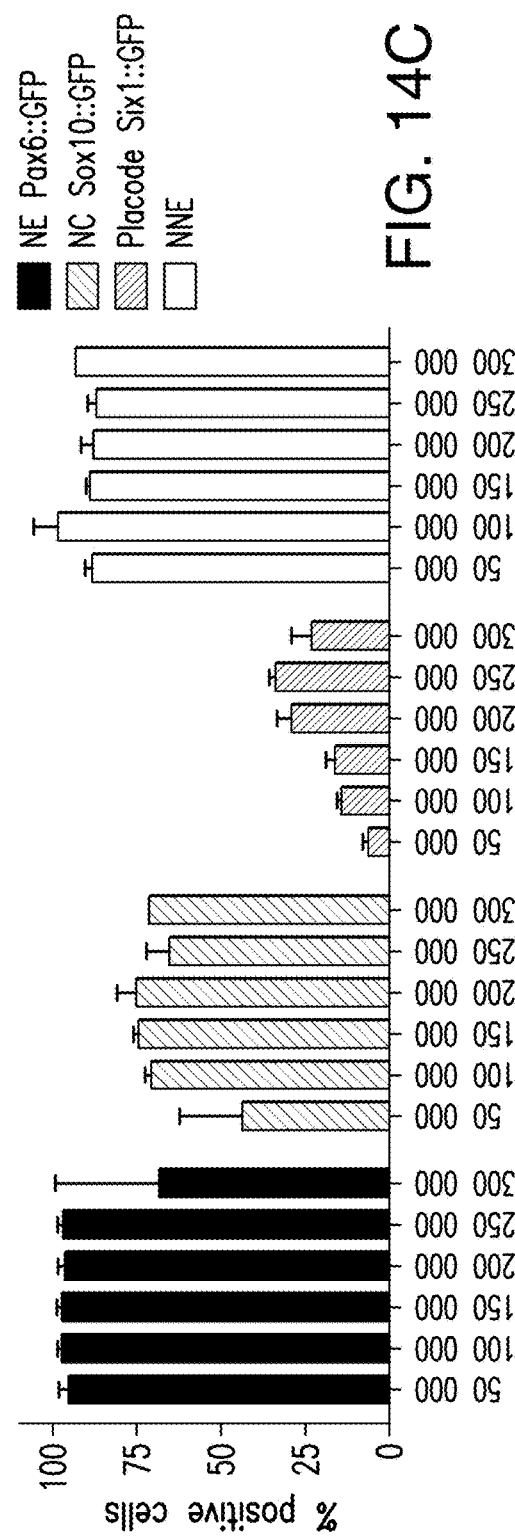

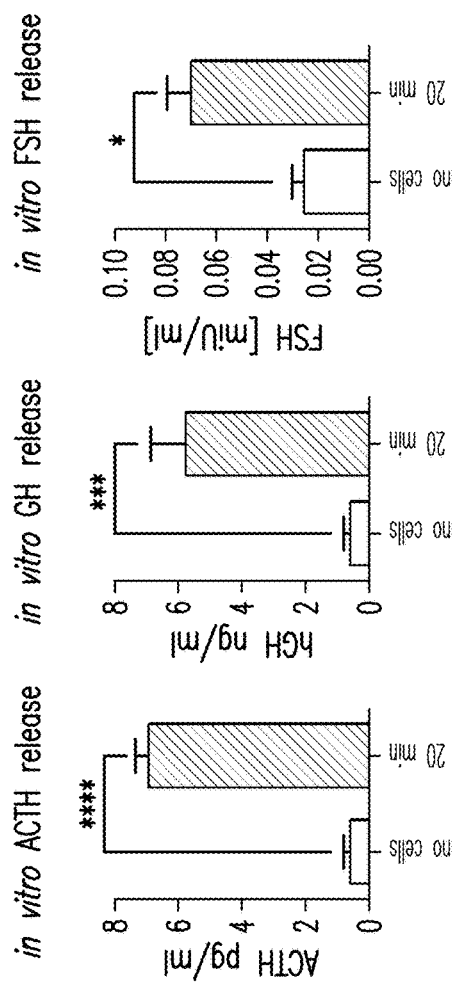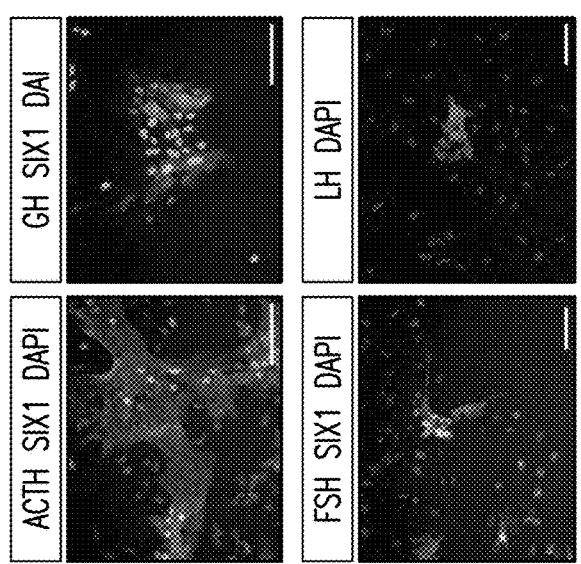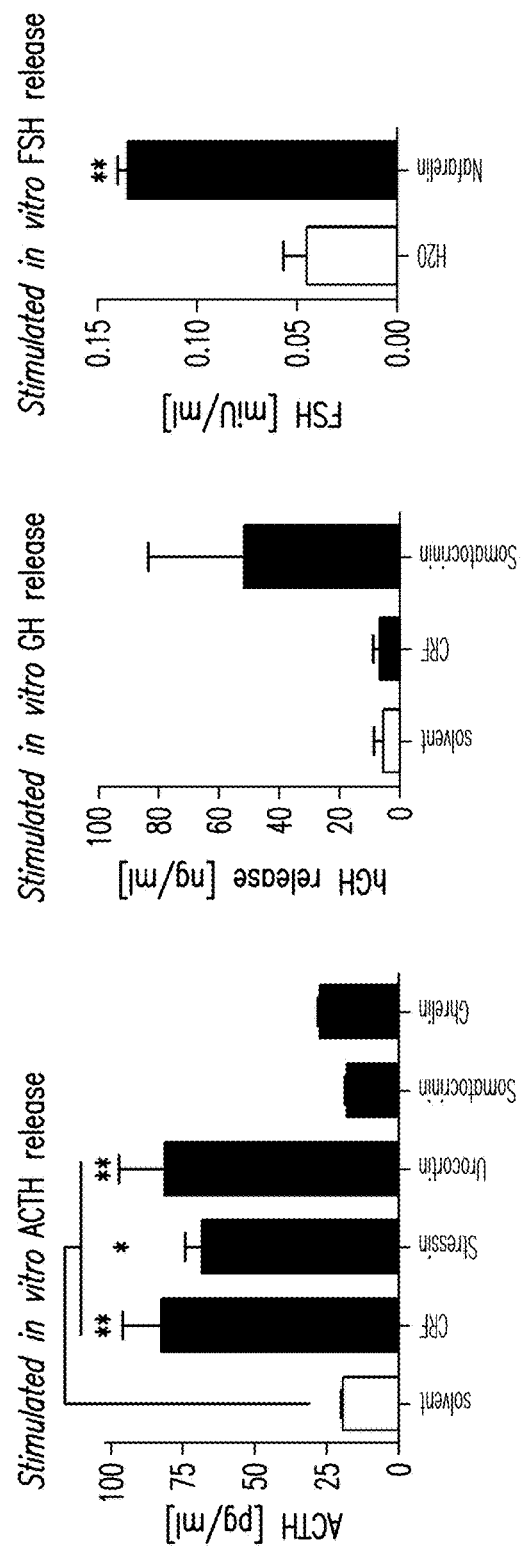

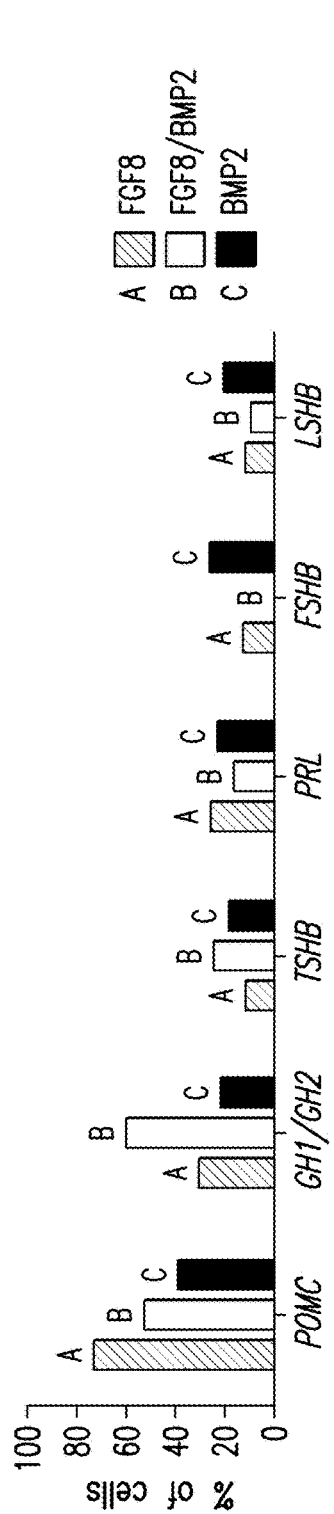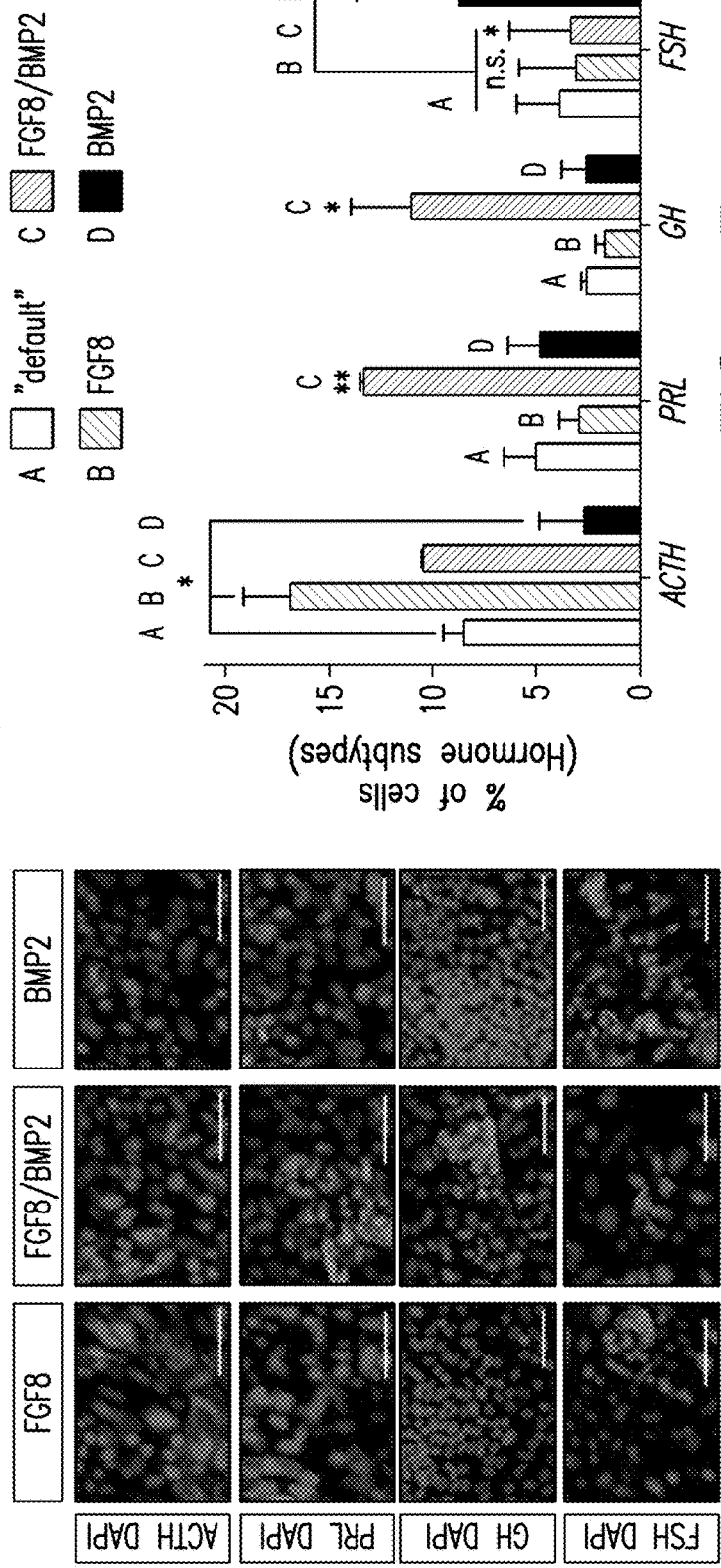

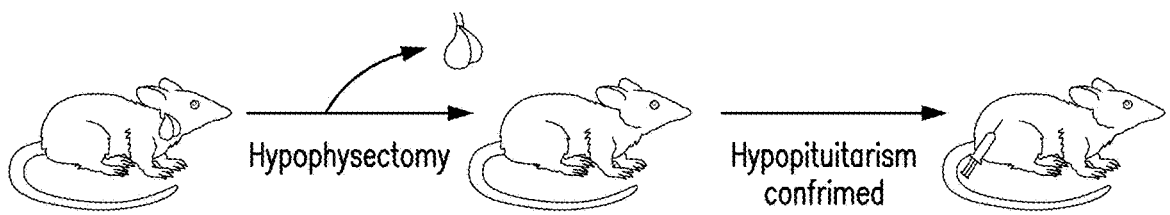
FIG. 21A
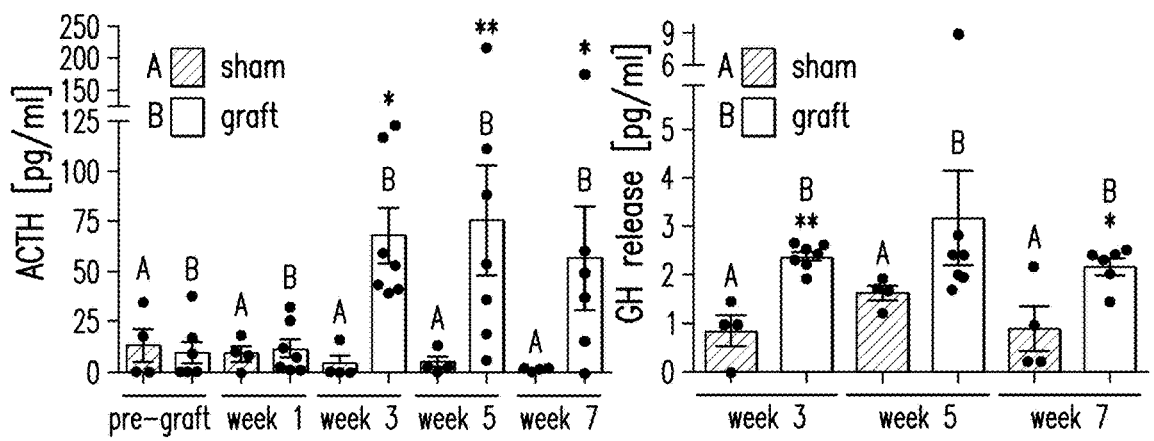
FIG. 21B
FIG. 21C
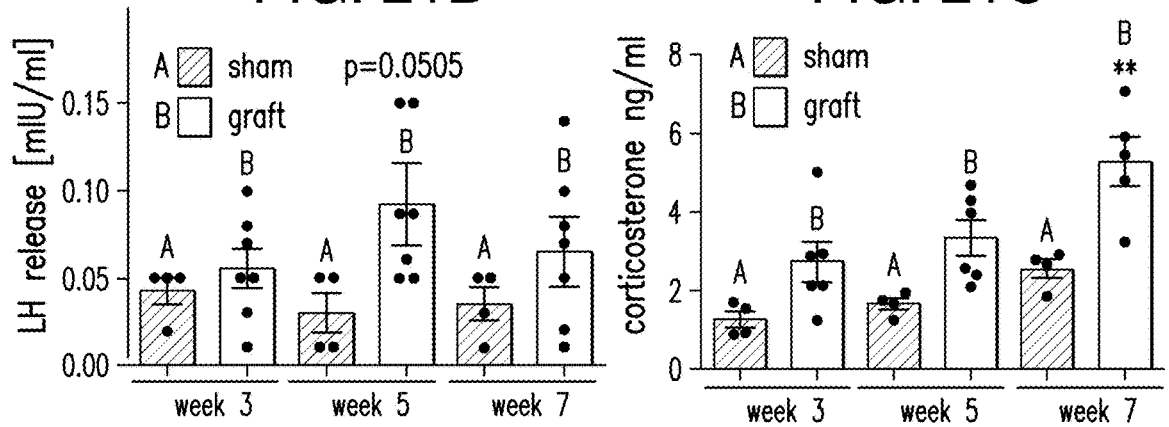
FIG. 21D
FIG. 21E
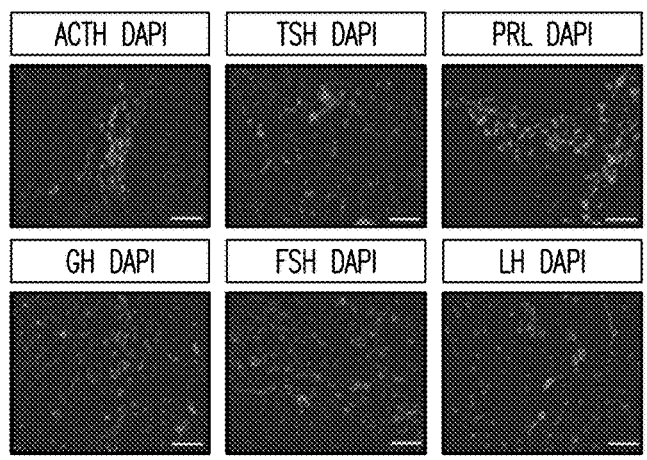
FIG. 21F
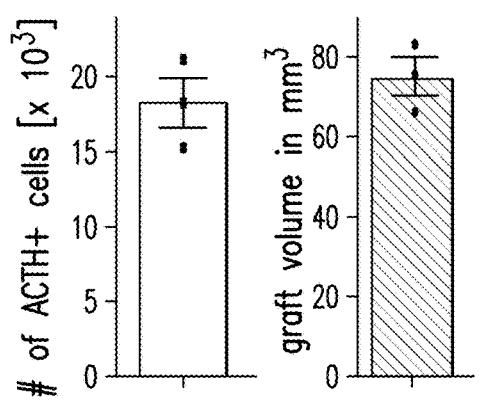
FIG. 21G

| Target | FP | | RP | | Design RefSeq |
|---|---|---|---|---|---|
| ACTB | CCAACCGCGAGAAGATGAC | SEQ ID NO: 10 | TAGCACAGCCTGGATAGCAA | SEQ ID NO: 44 | NM_001101.3 |
| FSHB | GTCGTTTCTGCATAAGCATCA | SEQ ID NO: 11 | CTGGCTGGGTCCTTATACAC | SEQ ID NO: 45 | NM_000510.2 |
| GAPDH | GAACGGGAAGCTTGTCATCAA | SEQ ID NO: 12 | ATCGCCCCACTTGATTTTGG | SEQ ID NO: 46 | NM_002046.4 |
| GATA2 | GCCTGTGGCCTCTACTACAA | SEQ ID NO: 13 | GTCTGGATCCCTTCCTTCTTCA | SEQ ID NO: 47 | NM_001145661.1 |
| GH1 | ACTGGGCAGATCTTCAAGCA | SEQ ID NO: 14 | GCAGCCCGTAGTTCTTGAGTA | SEQ ID NO: 48 | NM_000515.3 |
| GH2 | CCCGTCGCCTGTACCA | SEQ ID NO: 15 | TGTTGGAATAGACTCTGAGAAGCA | SEQ ID NO: 49 | NM_022557.3 |
| HESX1 | GTTGGTATAGAGGCCGAAGACC | SEQ ID NO: 16 | CCAGGATAGCACTTTACTCTAAAGACA | SEQ ID NO: 50 | NM_003865.2 |
| ISL1 | TCGCCTTGCAGAGTGACATA | SEQ ID NO: 17 | CCCGGTCCTCCTTCTGAAAA | SEQ ID NO: 51 | NM_002202.2 |
| LHB | GCACCAAGGATGCAGATGC | SEQ ID NO: 18 | GCTCCCTGGATGCCCAT | SEQ ID NO: 52 | NM_000894.2 |
| LHX3 | TCGGACAAGGACAGCCGTTCA | SEQ ID NO: 19 | GCCCATTTCCGCCAAGGAA | SEQ ID NO: 53 | NM_178138.3 |
| LHX4 | GGACTGTGGGGTTAGTGACA | SEQ ID NO: 20 | CCCCACGTTGCCATAAATCC | SEQ ID NO: 54 | NM_033343.2 |
| MYOD1 | ACGAAGGCGCCTACTACA | SEQ ID NO: 21 | GCAGTCTAGGCTCGACAC | SEQ ID NO: 55 | NM_002478.4 |
| NANOG | TGCCTTGCTTTGAAGCATCC | SEQ ID NO: 22 | TTTCTTCAGGCCCACAAATCAC | SEQ ID NO: 56 | NM_024865.2 |
| NEUROD1 | GGCCCCAGGGTTATGAGACTA | SEQ ID NO: 23 | ATCAGCCCACTCTCGCTGTA | SEQ ID NO: 57 | NM_002500.4 |
| OTX2 | AGGAGGTGGCACTGAAAATCA | SEQ ID NO: 24 | CTGTTGTTGGCGGCACTTA | SEQ ID NO: 58 | NM_021728.2 |
| PAX2 | CGGCTGTGTCAGCAAAATCC | SEQ ID NO: 25 | GCTTGGAGCCACCGATCA | SEQ ID NO: 59 | NM_000278.3 |
| PAX3 | GCGGTCTGTGATCCAAACA | SEQ ID NO: 26 | TCCTCCTCTTCACCTTTCCC | SEQ ID NO: 60 | NM_181461.3 |
| PAX6 | CCCCACATATGCAGACACACA | SEQ ID NO: 27 | GAACTGACACACCAGGGGAAA | SEQ ID NO: 61 | NM_001604.5 |
| PAX8 | GCCCAGTGTCAGCTCCATTA | SEQ ID NO: 28 | GCTGTCCATAGGGAGGTTGAA | SEQ ID NO: 62 | NM_003466.3 |
| PITX1 | CCGTGTGGACCAACCTCA | SEQ ID NO: 29 | GGTTACGCTCGCGCTTAC | SEQ ID NO: 63 | NM_002653.4 |
| PITX2 | GCTGTGTGGACCAACCTTAC | SEQ ID NO: 30 | CCCGAAGCCATTCTTGCATA | SEQ ID NO: 64 | NM_000325.5 |
| POMC | CTCACCACGGAAAGCAACC | SEQ ID NO: 31 | CTGCTCGTCGCCATTTCC | SEQ ID NO: 65 | NM_000939.2 |
| POU1F1 | AGGAACTCAGGCGGAAAAGTA | SEQ ID NO: 32 | CAGGGCCTCCCCAACA | SEQ ID NO: 66 | NM_000306.2 |
| POU5F1 | GGTATTCAGCCAAACGACCAT | SEQ ID NO: 33 | CCGCAGCTTACACATGTTCT | SEQ ID NO: 67 | NM_002701.4 |
| PRL | GGGCATGGAGCTGATAGTCA | SEQ ID NO: 34 | TCCCGACCAGACAGGGTA | SEQ ID NO: 68 | NM_000948.4 |
| PROP1 | AGTCAGCCTTTGGGAGGAAC | SEQ ID NO: 35 | GTGACGGCTCTTGCTTCC | SEQ ID NO: 69 | NM_006261.4 |
| SIX1 | AGAACCGGAGGCAAAGAGAC | SEQ ID NO: 36 | CTGCTTGTTGGAGGAGGAGTTA | SEQ ID NO: 70 | NM_005982.3 |
| SIX6 | AGGTGGGCAACTGGTTCA | SEQ ID NO: 37 | CCCGGAACCCTGTGAC | SEQ ID NO: 71 | NM_007374.2 |
| SOX17 | CACAACGCCGAGTTCAGCAA | SEQ ID NO: 38 | GCTCTGCCTCCTCCACCAA | SEQ ID NO: 72 | NM_022454.3 |
| SOX2 | CATGAAGGAGCACCCGGATTA | SEQ ID NO: 39 | CGGGCAGCGTGTACTTATCC | SEQ ID NO: 73 | NM_003106.2 |
| SOX3 | GTGTGAAACGGCCCATGAAC | SEQ ID NO: 40 | GTGCATCTTGGGGTTCTCCA | SEQ ID NO: 74 | NM_005634.2 |
| T | CGCTTCAAGGAGCTCACCAA | SEQ ID NO: 41 | GCCAGACACGTTCACCTTCA | SEQ ID NO: 75 | NM_003181.2 |
| TBX19 | ACCCAGTTCATAGCCGTGAC | SEQ ID NO: 42 | AGGCTTTGGCAAAAGGATTGTAC | SEQ ID NO: 76 | NM_005149.2 |
| TSHB | AATACCAGGATGCCCACTCC | SEQ ID NO: 43 | GTATTGCACTTGCCACACTTACA | SEQ ID NO: 77 | NM_000549.4 |

| Blast Hits | Gene Symbol | Gene Aliases |
|---|---|---|
| NM_001101 | ACTB | |
| NM_001018080.1\|NM_000510.2 | FSHB | |
| NM_002046\|NM_001256799 | GAPDH | |
| NM_032638\|NM_001145661\|NM_001145662 | GATA2 | |
| NM_022560\|NM_000515\|NM_022559\|NM_022562\|NM_022561 | GH1 | |
| NM_022558\|NM_002059\|NM_022557 | GH2 | |
| NM_003865.2 | HESX1 | |
| NM_002202.2 | ISL1 | |
| NM_000894 | LHB | CGB4\|hLHB\|LSH-B |
| NM_014564.2\|NM_178138.3 | LHX3 | LIM3\|CPHD3\|M2-LHX3 |
| NM_033343.2 | LHX4 | CPHD4 |
| NM_002478.4 | MYOD1 | |
| NM_024865 | NANOG | |
| NM_002500 | NEUROD1 | |
| NM_172337.1\|NM_021728.2 | OTX2 | |
| NM_003989.3\|NM_000278.3\|NM_003987.3\|NM_003988.3\|NM_003990.3 | PAX2 | |
| NM_181459.3\|NM_001127366.2\|NM_000438.5\|NM_181458.3\|NM_181457.3\|NM_013942.4\|NM_181460.3\|NM_181461.3 | PAX3 | |
| NM_001258465\|NM_001258464\|NM_001258463\|NM_000280\|NM_001604\|NM_001127612\|NM_001258462 | PAX6 | |
| NM_013992.3\|NM_013953.3\|NM_013952.3\|NM_003466.3 | PAX8 | |
| NM_002653.4 | PITX1 | BFT\|CCF\|POTX\|PTX1\|LBNBG |
| NM_000325.5\|NM_153426.1\|NM_153427.1 | PITX2 | |
| NM_000939.2\|NM_001035256.1 | POMC | LPH\|MSH\|NPP\|POC\|ACTH\|CLIP |
| NM_000306\|NM_001122757 | POU1F1 | PIT1\|CPHD1\|GHF-1\|Pit-1\|PQU1F1a |
| NM_001173531\|NM_203289\|NM_002701 | POU5F1 | |
| NM_000948.4\|NM_001163558.1 | PRL | |
| NM_006261 | PROP1 | CPHD2\|PROP-1 |
| NM_005982 | SIX1 | |
| NM_007374 | SIX6 | Six9\|OPTX2\|MCOPCT2 |
| NM_022454.3 | SOX17 | |
| NM_003106.2 | SOX2 | |
| NM_005634 | SOX3 | PHP\|GHDX\|MRGH\|PHPX\|SOXB |
| NM_003181.2 | T | |
| NM_005149.2 | TBX19 | TPIT\|TBS19\|dJ747L4.1 |
| NM_001277991\|NM_000549 | TSHB | TSH-B\|TSH-BETA |

FIG. 27 continued

Supplementary Table S2. Antibodies used in this study, related to Figure 1, 2, 3, 4, 6, 7, S1, S2, S3 and S5

| Antigen | Company | Catalogue # | diluition |
|---|---|---|---|
| ACTH | NIDDK | hACTH-IC | 1:100 |
| CRYAA | OriGene | CF505577 | 1:100 |
| CRYAB | OriGene | CF500680 | 1:100 |
| DLX3 | Santa Cruz | Sc-98522 | 1:100 |
| ECAD | BD Pharmigen | 560062 | 1:200 |
| EYA1 | Avia Systems Biology | ARP32434_P050 | 1:200 |
| FOXG1 | StemCulture | NCFAB | 1:1000 |
| FSH | NIDDK | hBetaFSH-IC-3 | 1:100 |
| GFP | Abcam | Ab13970 | 1:1000 |
| GH | NIDDK | hGH-IC-2 | 1:100 |
| HESX1 | Sigma | HPA024187 | 1:500 |
| LH | NIDDK | hBetaLH-IC-3 | 1:100 |
| LHX3 (rabbit) | Millipore | AB3202 | 1:300 |
| LHX3 (mouse) | DSHB | 67.4E12 | 1:100 |
| NKX2.1 (TTF1) | Thermo Scientific | MS-699 | 1:200 |
| OCT4 | Cell Signaling | 2840 | 1:400 |
| PAX3 | DSHB | Pax3 | 1:100 |
| PAX6 | Covance | PRB-278P | 1:800 |
| PITX1 | Sigma | HPA008743 | 1:500 |
| PRL | NIDDK | hPRL-IC-5 | 1:100 |
| SIX1 | Sigma | HPA001893 | 1:500 -1:1000 |
| SIX3/6 | Santa Cruz | sc-9126 X | 1:300 |
| SOX10 | Santa Cruz | sc-17342 | 1:100 |
| SOX2 | Cell Signaling | 3579 | 1:400 |
| TFAP2A | DSHB | 3B5 | 1:100 |
| TSH | NIDDK | hBetaTSH-IC-2 | 1:100 |

FIG. 28

SEQUENCE LISTING

```
<160> NUMBER OF SEQ ID NOS: 77

<210> SEQ ID NO 1
<211> LENGTH: 59
<212> TYPE: DNA
<213> ORGANISM: Homo sapiens

<400> SEQUENCE: 1
taccagccta tctaccccca gtcgcaagat ccttactccc acgtcaacga ccctacag      59

<210> SEQ ID NO 2
<211> LENGTH: 60
<212> TYPE: DNA
<213> ORGANISM: Homo sapiens

<400> SEQUENCE: 2
accctaccag cctatctacc cccagtcgca agatccttac tcccacgtca acgacccta    60

<210> SEQ ID NO 3
<211> LENGTH: 54
<212> TYPE: DNA
<213> ORGANISM: Homo sapiens

<400> SEQUENCE: 3
caccctacca gcctatctac ccccagtcgc aagatcctta ctcccacgtc aacg          54

<210> SEQ ID NO 4
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other

<400> SEQUENCE: 4
caccctacca gcctatctac ccccagnata gngggcaaga cccttactcc tacgtcctga   60
```

```
<210> SEQ ID NO 5
<211> LENGTH: 60
<212> TYPE: DNA
<213> ORGANISM: Homo sapiens

<400> SEQUENCE: 5
ccaccctacc agcctatcta cccccagtcg caagatcctt actcccacgt caacgacccc    60

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, t, g, unknown or other

<400> SEQUENCE: 6
ccaccctacc agcctatcta ccccctccnag gtaaacaacc cc                      42

<210> SEQ ID NO 7
<211> LENGTH: 60
<212> TYPE: DNA
<213> ORGANISM: Homo sapiens

<400> SEQUENCE: 7
cctaccagcc tatctacccc cagtcgcaag atccttactc ccacgtcaac gacccctaca    60

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctaccagcc tatctacccc cagtttacac ccatatccac gacccctaca               50

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctctctgctc ggcccccctca cctccagtct ggtggacttg gggtcctaag tggggagg     58

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccaaccgcga gaagatgac                                                 19

<210> SEQ ID NO 11
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcgtttctg cataagcatc a                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaacgggaag cttgtcatca a                                             21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcctgtggcc tctactacaa                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
actgggcaga tcttcaagca                                               20

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccgtcgcct gtacca                                                   16

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gttggtatag aggccgaaga cc                                            22

<210> SEQ ID NO 17
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgccttgca gagtgacata                                                   20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcaccaagga tggagatgc                                                    19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcggacaagg acagcgttca                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggactgtggg gttagtgaca                                                   20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgaaggcgc ctactaca                                                     18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgccttgctt tgaagcatcc                                                   20

<210> SEQ ID NO 23
<211> LENGTH: 21
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 23
ggccccaggg ttatgagact a                                          21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aggaggtggc actgaaaatc a                                          21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggctgtgtc agcaaaatcc                                            20

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcggtctgtg atcgaaaca                                             19

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccccacatat gcagacacac a                                          21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcccagtgtc agctccatta                                            20

<210> SEQ ID NO 29
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 29
ccgtgtggac caacctca                                                    18

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctgtgtgga ccaaccttac                                                  20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcaccacgg aaagcaacc                                                   19

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggaactcag gcggaaaagt a                                                21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtattcagc caaacgacca t                                                21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gggcatggag ctgatagtca                                                  20

<210> SEQ ID NO 35
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 35
agtcagcctt tgggaggaac                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agaaccggag gcaaagagac                                               20

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aggtgggcaa ctggttca                                                 18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacaacgccg agttgagcaa                                               20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgaaggag cacccggatt a                                             21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtgtgaaacg gcccatgaac                                               20

<210> SEQ ID NO 41
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 41
cgcttcaagg agctcaccaa                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acccagttca tagccgtgac                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aataccagga tgcccactcc                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tagcacagcc tggatagcaa                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctggctgggt ccttatacac                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atcgccccac ttgattttgg                                              20

<210> SEQ ID NO 47
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 47
gtctggatcc cttccttctt ca                                              22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcagcccgta gttcttgagt a                                               21

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgttggaata gactctgaga agca                                            24

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccaggatagc agtttactct aaagaca                                         27

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cccggtcctc cttctgaaaa                                                 20

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctccctgga tgcccat                                                    17

<210> SEQ ID NO 53
<211> LENGTH: 19
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 53
gcccatttcc gccaaggaa                                                  19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccccacgttg ccataaatcc                                                 20

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcagtctagg ctcgacac                                                   18

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tttcttcagg cccacaaatc ac                                              22

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atcagcccac tctcgctgta                                                 20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctgttgttgg cggcactta                                                  19

<210> SEQ ID NO 59
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 59
gcttggagcc accgatca                                                        18

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcctcctctt caccttccc                                                       20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaactgacac accaggggaa a                                                    21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gctgtccata gggaggttga a                                                    21

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggttacgctc gcgcttac                                                        18

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cccgaagcca ttcttgcata                                                      20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctgctcgtcg ccatttcc                                                       18

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cagggcctcc ccaaca                                                         16

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccgcagctta cacatgttct                                                     20

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tcccgaccag acagggta                                                       18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtgagcgctc ttgcttcc                                                       18

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctgcttgttg gaggaggagt ta                                                  22

<210> SEQ ID NO 71
<211> LENGTH: 16
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 71
cccggaaccc tgtgac                                                    16

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gctctgcctc ctccacgaa                                                 19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgggcagcgt gtacttatcc                                                20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtgcatcttg gggttctcca                                                20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gccagacacg ttcaccttca                                                20

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aggctttggc aaaaggattg tac                                            23

<210> SEQ ID NO 77
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 77
gtattgcact tgccacactt aca                                              23
```

METHODS OF DIFFERENTIATING STEM CELL-DERIVED ECTODERMAL LINEAGE PRECURSORS

CROSS REFERENCE TO RELATED APPLICATIONS

The application is a Continuation of International Patent Application No. PCT/US17/16723 filed Feb. 6, 2017, which claims priority to U.S. Provisional Patent Application No. 62/292,014 filed Feb. 5, 2016, U.S. Provisional Patent Application No. 62/299,361 filed Feb. 24, 2016, and U.S. Provisional Patent Application No. 62/350,032 filed Jun. 14, 2016, the contents of each of which are incorporated by reference in their entireties herein, and priority to each of which is claimed.

SEQUENCE LISTING

The specification further incorporates by reference the Sequence Listing submitted herewith via EFS on Nov. 21, 2018. Pursuant to 37 C.F.R. § 1.52(e)(5), the Sequence Listing text file, identified as 072734_0766_SL.txt, is 17,717 bytes and was created on Nov. 21, 2018. The entire contents of the Sequence Listing are hereby incorporated by reference. The Sequence Listing does not extend beyond the scope of the specification and thus does not contain new matter.

1. INTRODUCTION

The presently disclosed subject matter relates to cells of the four main ectodermal lineages, CNS, neural crest, cranial placode, and non-neural ectoderm, derived from human stem cells, and uses thereof for cell-based treatment and drug discovery in neurological disorders.

2. BACKGROUND OF THE INVENTION

Early developmental cell types are difficult to isolate and study in humans. The directed differentiation of pluripotent stem cells (PSCs) offers a model system to access early fate decisions in a systematic manner for applications in basic and translational biology. Several strategies exist to differentiate PSCs into early lineages such as spontaneous differentiation paradigms and directed differentiation strategies based on the in vitro modulation of developmental pathways known to act during development in vivo. Factors that greatly affect outcome across various differentiation platforms include the use of feeder cells, monolayer versus embryoid body based strategies or complex media compositions. For example, many published protocols involve media containing serum or serum-replacement factors such as KSR for deriving a desired fate. Batch-to-batch variability in the manufacturing of those reagents affects reproducibility of differentiation making it often necessary to pursue laborious lot testing in order to generate a specific cell type of interest (Blauwkamp et al., 2012). While such extensive quality control strategies for complex reagents such as KSR are feasible for any single protocol, they prevent the development of more ambitious strategies aimed at generating dozens or possibly hundreds of defined cell types in a modular fashion.

Protocols have been established to derive multiple cell types of the nervous system based on the addition LDN193189 and SB431542, small molecules that inhibit the BMP and TGFβ signaling pathways, respectively, which thereby inhibits SMAD signaling. This inhibitory cocktail combination, termed dual SMAD inhibition (dSMADi), allows for the efficient generation of cells in the central nervous system (CNS) defaulting towards an anterior neuroectoderm (NE) marked by expression of the transcription factor Pax6 (Chambers et al., 2009). Modifications to dSMADi can yield many different neural subtypes along the neuraxis of the embryo including forebrain, midbrain and spinal cord progenitors. In addition, dSMADi can be adapted to generate non-CNS cell types such as neural crest (NC) (Mica et al., 2013), cranial placode (CP) and non-neural ectoderm (NNE) (Dincer et al., 2013). Overall, dSMADi is a robust and widely used platform that that will generate a near homogenous layer of Pax6+NE. However, even for deriving Pax6+NE under dSMADi, the acquisition of the most anterior, telencephalic marker FOXG1+ in PAX6+ cells, can be affected by KSR batch variability. Therefore, a scalable and fully modular differentiation platform should be devoid of KSR or other complex media factors.

3. SUMMARY OF THE INVENTION

The presently disclosed subject matter relates to neural crest (NC), cranial placode (CP), and non-neural ectoderm (NNE) precursors derived from human stem cells, e.g., by in vitro differentiation.

The presently disclosed subject matter is based at least in part on the discovery that the non-CNS ectodermal lineages of the neural crest, cranial placode and non-neural ectoderm can be differentiated from human stem cells by inhibition of SMAD signaling (for example, by inhibition of TGFβ/Activin-Nodal signaling) along with activation of BMP signaling, wherein BMP signaling is activated for at least 2 days after initial contact of the cells to effective amounts of one or more SMAD inhibitor and one or more BMP activator, and wherein the cells are further contacted with effective amounts of one or more NC, CP or NNE lineage specific activators and inhibitors. For example, the stem cells can be differentiated to NC by further contacting the cells with effective amounts of one or more Wnt activator; CP can be differentiated from the stem cells by further contacting the stem cells with effective amounts of one or more activator of FGF; and NNE can be differentiated from the stem cells by further contacting the stem cells with effective amounts of one or more inhibitor of FGF.

In certain embodiments, the cells are contacted to effective amounts of the one or more inhibitor of transforming growth factor beta (TGFβ)/Activin-Nodal signaling and one or more activator of BMP signaling for at least about 2 days. In certain embodiment, the cells are contacted to effective amounts of one or more inhibitor of transforming growth factor beta (TGFβ)/Activin-Nodal signaling for at least about 12 days. In certain embodiments, effective amounts of the one or more inhibitor of transforming growth factor beta (TGFβ)/Activin-Nodal signaling and one or more activator of BMP signaling are contacted to the population of cells concurrently.

In certain embodiments, the presently disclosed subject matter provides for in vitro methods for inducing differentiation of human stem cells into non-CNS NC precursors comprising contacting a population of human stem cells with effective amounts of one or more inhibitor of TGFβ/Activin-Nodal signaling, effective amounts of one or more activator of BMP signaling, and effective amounts of one or more activator of wingless (Wnt) signaling. In certain embodiments, the cells are contacted with the effective amounts of one or more activator of BMP signaling for at least about 2 days, or at least about 3 days, to produce a population of cells that express detectable levels of one or markers selected from TFAP2A, TFAP2B, NEUROG1, HAND1, ISL1, BRN3a and/or MASH1. In certain embodiments, the cells are contacted with effective amounts of the foregoing agents for a period of time such that at least 10%, 20%, 30%, 40%, 50% or 60% or more of the cells express detectable levels of the foregoing markers. In certain embodiments, the effective amounts of one or more activator of Wnt signaling and inhibitor of TGFβ/Activin-Nodal signaling are contacted to the cells concurrently, wherein the concentration of Wnt activator is increased about 2 days after the cells are initially contacted with the Wnt activator, and wherein the cells are contacted with the increased level of Wnt for up to about 10, 11, or 12 days or more. In certain embodiment, the cells express detectable levels of SOX10, for example, after about 12 days after initially contacted with the effective amounts of the one or more inhibitor of TGFβ/Activin-Nodal signaling. In certain embodiments, the cells are contacted with effective amounts of the foregoing agents for a period of time such that at least 10%, 20%, 30%, 40%, 50% or 60% or more of the cells express detectable levels of SOX10.

In certain embodiments, the presently disclosed subject matter provides for in vitro methods for inducing differentiation of human stem cells into non-CNS CP precursors comprising contacting a population of human stem cells with effective amounts of one or more inhibitor of TGFβ/Activin-Nodal signaling, effective amounts of one or more activator of BMP signaling, and effective amounts of one or more activator of fibroblast growth factors (FGF) signaling. In certain embodiments, the cells are contacted with the effective amounts of one or more activator of BMP signaling for at least about 2 days, or at least about 3 days, to produce a population of cells that express detectable levels of one or more markers selected from TFAP2A, TFAP2B, NEUROG1, HAND1, ISL1, BRN3a, and/or MASH1. In certain embodiments, the cells are contacted with effective amounts of the foregoing agents for a period of time such that at least 10%, 20%, 30%, 40%, 50% or 60% or more of the cells express detectable levels of the foregoing markers. In certain embodiments, the effective amounts of one or more activator of FGF signaling is contacted to the cells at least 2 days after the cells are contacted with the inhibitor of TGFβ/Activin-Nodal signaling. In certain embodiment, the cells express detectable levels of SIX1 and/or ELAVL4, for example, after about 12 days after initially contacted with the inhibitor of TGFβ/Activin-Nodal signaling. In certain embodiments, the cells express detectable levels of one or more lens placode precursor markers selected from SIX1, PAX6, PITX3, Crystallin alpha A, and/or Crystallin alpha B about 12 days after the cells are contacted with the inhibitor of TGFβ/Activin-Nodal signaling. In certain embodiments, the cells are contacted with effective amounts of the foregoing agents for a period of time such that at least 10%, 20%, 30%, 40%, 50% or 60% or more of the cells express detectable levels of the foregoing markers.

In certain embodiments, the cells are further contacted with effective amounts of one or more activator of Wnt signaling at least 2 days after being contacted with the effective amounts of one or more inhibitor of TGFβ/Activin-Nodal signaling, wherein the cells are contacted to the effective amounts of one or more Wnt activator for about 2 days. In certain embodiments, the cells are not contacted with an activator of FGF during or after contact of the cells with an activator of Wnt. In certain embodiments, the cells express detectable levels of the trigeminal placode precursor marker PAX3, for example, after about 12 days after initially contacted with the effective amounts of one or more inhibitor of TGFβ/Activin-Nodal signaling. In certain embodiments, the cells are contacted with effective amounts of the foregoing agents for a period of time such that at least 10%, 20%, 30%, 40%, 50% or 60% or more of the cells express detectable levels of SI1 and/or PAX3.

In certain embodiments, the presently disclosed subject matter provides for in vitro methods for inducing differentiation of human stem cells into pituitary cells, or cranial placode precursors thereof, by contacting the cells with effective amounts of one or more inhibitor of TGFβ/Activin-Nodal signaling, effective amounts of one or more activator of BMP signaling, effective amounts of one or more activator of Sonic Hedgehog (SHH) signaling, and effective amounts of one, two or more activators of FGF signaling. In certain embodiments, the activators of FGF signaling activate FGF8 and FGF10 signaling. In certain embodiments, the cells are contacted with the effective amounts of one or more activator of BMP signaling for at least about 2 days, or at least about 3 days. In certain embodiments, the cells are contacted with the effective amounts of one or more activator of SHH signaling and the effective amounts of one, two or more activators of FGF signaling at least 4 days after the cells are contacted with the effective amounts of one or more inhibitor of TGFβ/Activin-Nodal signaling, and wherein the cells are contacted for up to at least 26 days or more with the one or more SHH activator and the one, two or more FGF activators.

In certain embodiments, the foregoing methods to produce a population of pituitary cells, or cranial placode precursors thereof, produces a population of cells that express detectable levels of one or more markers selected from PITX1, PITX2, LUX, LHX4, HESX1, SIX6, TBX19, PAX6, or combinations thereof. In certain embodiments, the cells are contacted with effective amounts of the foregoing agents for a period of time such that at least 10%, 20%, 30%, 40%, 50% or 60% or more of the cells express detectable levels of the foregoing markers.

In certain embodiments, the cells are further contacted with effective amounts of one or more dorsalizing agents, for example, an activator of FGF signaling; effective amounts of one or more ventralizing agent, for example, an activator of BMP signaling; or a combination thereof, wherein the cells are contacted with the agent(s) at least 30 days after the cells are contacted to the effective amounts of one or more inhibitor of TGFβ/Activin-Nodal signaling. In certain embodiments, the cells are contacted with the effective amounts of the agent(s) for at least 30 days or more.

In certain embodiments, the presently disclosed subject matter provides for in vitro methods for inducing differentiation of human stem cells into non-CNS NNE precursors comprising contacting a population of human stem cells with effective amounts of one or more inhibitor of TGFβ/Activin-Nodal signaling, effective amounts of one or more activator of BMP signaling, and effective amounts of one or more inhibitor of FGF signaling. In certain embodiment, the cells express detectable levels of TFAP2A, and do not express detectable levels of SIX1 and/or SOX10, for example, after about 12 days after initially contacted with the effective amounts of one or more inhibitor of TGFβ/Activin-Nodal signaling. In certain embodiments, the cells are contacted with effective amounts of the foregoing agents for a period of time such that at least 10%, 20%, 30%, 40%, 50% or 60% or more of the cells express detectable levels of TFAP2A.

In certain embodiments, the method comprises concurrently contacting said population of human stem cells with said effective amounts of one or more inhibitor of TGFβ/Activin-Nodal signaling and said effective amounts of one or more activator of BMP signaling.

In certain embodiments, said population of human stem cells are differentiated into a population of differentiated cells that express one or more neural crest, cranial placode or non-neural ectoderm lineage marker on or after about 12 days after initial contact with said effective amounts of one or more inhibitor of TGFβ/Activin-Nodal signaling.

The present disclosure also provides for a population of in vitro differentiated cells expressing one or more neural crest, cranial placode or non-neural ectoderm lineage marker prepared according to the methods described herein. In certain embodiments, the differentiated cell population is derived from a population of human stem cells. The presently disclosed subject matter further provides for compositions comprising such a differentiated cell population.

Furthermore, the presently disclosed subject matter provides for kits for inducing differentiation of stem cells.

In certain embodiments, the kit comprises (a) one or more inhibitor of transforming growth factor beta (TGFβ)/Activin-Nodal signaling, (b) one or more activator of BMP signaling, (c) one or more activator of Wnt signaling, and (d) instructions for inducing differentiation of the stem cells into a population of differentiated cells that express one or more neural crest lineage marker.

In certain embodiments, the kit comprises (a) one or more inhibitor of transforming growth factor beta (TGFβ)/Activin-Nodal signaling, (b) one or more activator of BMP signaling, (c) one or more activator of FGF signaling, and (d) instructions for inducing differentiation of the stem cells into a population of differentiated cells that express one or more cranial placode lineage marker. In certain embodiments, the kit optionally comprises (e) one or more activator of Wnt signaling.

In certain embodiments, the kit comprises (a) one or more inhibitor of transforming growth factor beta (TGFβ)/Activin-Nodal signaling, (b) one or more activator of BMP signaling, (c) one or more inhibitor of FGF signaling, and (d) instructions for inducing differentiation of the stem cells into a population of differentiated cells that express one or more non-neural ectoderm lineage marker.

In certain embodiments, the kit comprises (a) one or more inhibitor of transforming growth factor beta (TGFβ)/Activin-Nodal signaling, (b) one or more activator of BMP signaling (c) one or more activator of SHH signaling, (d) two or more activators of FGF signaling, and (e) instructions for inducing differentiation of the stem cells into a population of differentiated cells that express one or more pituitary cell or pituitary cell precursor marker.

In certain embodiments, the present disclosure provides for kits comprising the stem cell-derived precursors prepared according to the methods described herein. In certain embodiments, the stem cell-derived cells are mature, differentiated cells.

In certain embodiments, said one or more inhibitor of TGFβ/Activin-Nodal signaling is a small molecule selected from the group consisting of SB431542, derivatives thereof, and mixtures thereof. In certain embodiments, said one or more activator of Wnt signaling lowers glycogen synthase kinase 3β (GSK3β) for activation of Wnt signaling. In certain embodiments, said one or more activator of Wnt signaling is a small molecule selected from the group consisting of CHIR99021, WNT3A, derivatives thereof, and mixtures thereof. In certain embodiments, said activators of FGF signaling are selected from the group consisting of FGF2, FGF8, FGF10, derivatives thereof, and mixtures thereof. In certain embodiments, said inhibitor of FGF signaling is a small molecule selected from the group consisting of SU5402, derivatives thereof, and mixtures thereof. In certain embodiments, said activator of BMP signaling is selected from the group consisting of BMP4, BMP2, derivatives thereof, and mixtures thereof. In certain embodiments, the activator of SHH signaling is selected from the group consisting of Sonic hedgehog (SHH), C25II and smoothened (SMO) receptor small molecule agonists such as purmorphamine, derivatives thereof, and mixtures thereof.

In certain embodiments, said human stem cells are selected from the group consisting of human embryonic stem cells, human induced pluripotent stem cells, human parthenogenetic stem cells, primordial germ cell-like pluripotent stem cells, epiblast stem cells, and F-class pluripotent stem cells.

In certain embodiments, the method further comprises subjecting said population of differentiated cells to conditions favoring maturation of said differentiated cells into a population of NC-derived neurons, CP-derived neurons, or NNE-derived cells.

The presently disclosed subject matter further provides for methods of treating a neurodegenerative disorder or pituitary disorder in a subject. In certain embodiments, the method comprises administering an effective amount of the differentiated cell population described herein into a subject suffering from a neurodegenerative disorder or pituitary disorder.

The presently disclosed subject matter further provides for a differentiated cell population described herein for treating a neurodegenerative disorder or pituitary disorder in a subject.

The presently disclosed subject matter further provides for uses of the differentiated cell population described herein in the manufacture of a medicament for treating a neurodegenerative disorder or pituitary disorder.

In certain embodiments, the pituitary disorder is a hypopituitary disorder.

4. BRIEF DESCRIPTION OF THE FIGURES

FIGS. 1A-1F shows (A) the protocol for differentiating neuroectoderm (NE), neural crest (NC), cranial placode (CP), non-neural ectoderm (NNE) from human pluripotent stem cells (hPSC) in KSR media. (B) Expression of SOX1, PAX6, TFAP2A, SOX10 in NE, NC, CP and NNE differentiated in KSR. (C, D) Differentiation of the human pluripotent stem cells in KSR media into specific cell types produced an average of 95%, 50% and 58% of NE, Placode and NC, respectively. (E) The percentage of cells expressing PAX6 was improved upon addition of SB431542 (SB) or dSMADi (i.e., SB and LDN193189) to human pluripotent stem cells cultured in E6 media, wherein the percentage of PAX6 positive cells increased to nearly 90% and 80%, respectively. (F) A comparative gene expression analysis of hPSCs differentiated towards NC fate in KSR media versus E6 media revealed a lack of non-neural marker expression when cultured in E6 media.

FIGS. 2A-2J (A) BMP signaling has been shown to be important for the formation of NNE and Placode in the developing chick embryo (Groves and LaBonne, 2014). (B, C) TFAP2A expression is rapidly upregulated within three days of treatment with BMP in a dose dependent manner, in combination with SB431542 in E6 media. (D) At 20 ng/ml BMP, cells become TFAP2A positive and lack the expression of SOX10 and SIX1 implying that NNE is triggered by strong BMP signaling activation. (E) Culturing hPSC with SB, BMP and SU5402 generated NNE progenitors, which expressed immature (K14 positive) and mature (K18 positive) epidermal cell markers. (F) A three day BMP pulse in combination with SB431542 resulted in differentiation of hPSCs into SIX1 positive CP progenitors. (G) The addition of FGF2, but not FGF8, to the E6 culture comprising SB431542 and BMP during differentiation of hPSC enhanced the formation of SIX1 positive CP cells to nearly 50%. (H, I) Terminal differentiation of SIX1 positive CP precursors (by culturing the cells for 30 days) resulted in an increase in lens specific factors such as PITX3, Crystallin Alpha A and B. (J) Exposure of hPSC to Wnt activation in combination with SB431542, BMP and FGF2 in E6 media differentiated the cells into CP precursors expressing SIX1 and PAX3, indicative of trigeminal placode fate.

FIGS. 3A-3C (A) Activation of Wnt signaling in combination with a short pulse of BMP4 (1 ng/nil) and SB431542 was capable to generate a nearly homogenous SOX10 positive NC population. (B) The addition of both Wnt and BMP, along with SB431542 to the E6 media, activated TFAP2A expression as well as DLX3, another marker of the non-neural ectodermal fates. (C) Differentiation of the SOX10 positive NC precursors gave rise to autonomic and sensory neurons marked by Isl1 and Mash1 positive expression.

FIGS. 4A-4F shows (A, B) the transcriptional expression signatures of all 4 human ectodermal lineages. NE clustered closely with hESCs, while NNE clustered the furthest apart from all other ectodermal lineages. NC and CP clustered closely to each other. (C D) The 4 ectodermal progenitors upregulate and downregulate expression of different genes, which were subjected to gene ontology analysis (Edgar et al., 2013). Genes associated with extracellular matrix reorganization were significantly enriched in all non-CNS derived cell types. Ontologies associated with NE involve synaptic transmission and nervous system development. (E) Genes specifically upregulated during ectoderm differentiation that are shared between the CNS and non-CNS fates include ANXA1, LGI1, NR2F2 and ZNF503. Factors expressed by non-CNS cell precursors that distinguish the cells from CNS precursors include NEUROG1, HAND1, TFAP2A and TFAP2B. (F) Cells of the 4 ectoderm lineages also exhibited differences in gene expression. In NE, SOX1, Hes5 and PAX6 were upregulated, while low-level PAX6 transcripts could be found in all other lineages. High levels of the zinc finger protein ZNF229 were specifically observed in the NC lineage. ELAVL4 and SMYD1 were preferentially expressed in placode and NNE, respectively.

FIGS. 5A-5D (A) Knockout of TFAP2A expression in hESC resulted in a loss of TFAP2A expression after a short 3-day induction in the presence of high BMP. (B) Wild-type hESCs exhibited robust upregulation of E-cadherin at day 6 of differentiation under CP or NNE conditions, compared to TFAP2A knockout cells, which did not express E-cadherin under the CP or NNE conditions. (C, D) Differentiation of NE was not affected by TFAP2A knockout, as evident by PAX6 and SOX1 expression. Although NC and CP protocols resulted in increased levels of SOX1 and PAX6 expression in TFAP2A knockout versus wild type cells, SOX10 and SIX1 expression was also detected, indicating that abolishing TFAP2A expression is not sufficient to suppress non-CNS cell types.

FIGS. 6A-6E shows (A) a small molecule screen using the Library of Pharmacologically Active Compounds (LOPAC) using the Six1::H2B-GFP reporter line to identify compounds that enhance CP induction. (B, C) Three candidate compounds that increased expression of SIX1 above the levels observed in control differentiations were identified: BRL-5443 a serotonin receptor agonist; Parthenolide, a plant hormone that has the capacity to inhibit NF-kB and STAT mediated confirmation transcription; and Phenantroline, a metalloprotease inhibitor. (D) Differentiation towards CP showed a five-fold increase in SIX1 expression in the presence of Phenantroline over controls, without inducing the expression of other lineage markers such as Sox10, T, MyoD or Sox17. (E) There was a nearly 4-fold increase (69% versus 18%) of SIX1 positive cells upon addition of Phenantroline to the CP protocol in the absence of FGF2. After the addition of FGF2, or FGF2 plus Phenantroline, the enrichment of SIX1 positive cells was decreased to, 34% and 46%, respectively.

FIGS. 8A-8F Shows the generation of PAX6::H2B-GFP and SIX1::H2B-GFP hESC reporter cell lines.

FIGS. 9A-9E Shows (A) KSR differentiation protocol used in the presence of E6 media. (B) Although hESCs can differentiate into NE precursors in E6 without addition of any small molecules, the percentage of cells expressing PAX6 was further improved upon addition of SB431542 or dSMADi to nearly 90% and 80%, respectively. (C, D) NC induction did not generate either PAX6 or SOX10 positive cells in E6 media, indicating that Wnt activation may alter the regional identity of differentiating cells rather than inducing NC. (E) PAX6 positive NE efficiently differentiated further into Tbr1 positive cortical neurons in E6 media.

Figure 10:
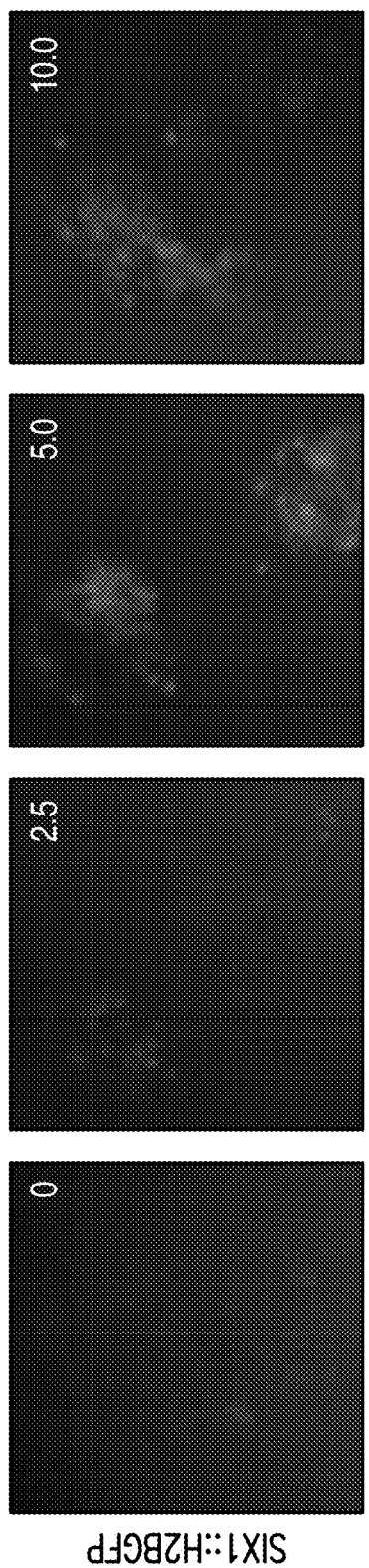

FIG. 10 Shows that a three-day pulse of BMP signaling in combination with SB431542 was sufficient to generate SIX1 positive CP precursors in E6 media. Dose-response studies showed that moderate concentrations of BMP4 (around 5 ng/ml) resulted in CP induction.

Figure 11:
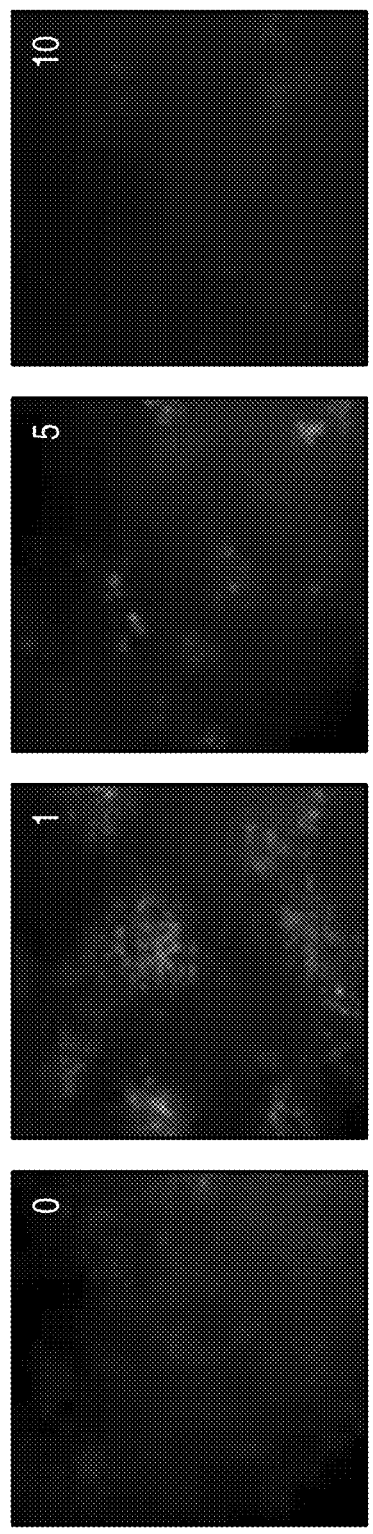

FIG. 11 Shows that a three-day pulse of BMP signaling in combination with SB431542 was sufficient to generate SOX10 positive NC precursors in E6 media. Dose-response studies showed that low concentrations of BMP4 (around 1 ng/ml) resulted in strong NC induction.

Figure 12C:
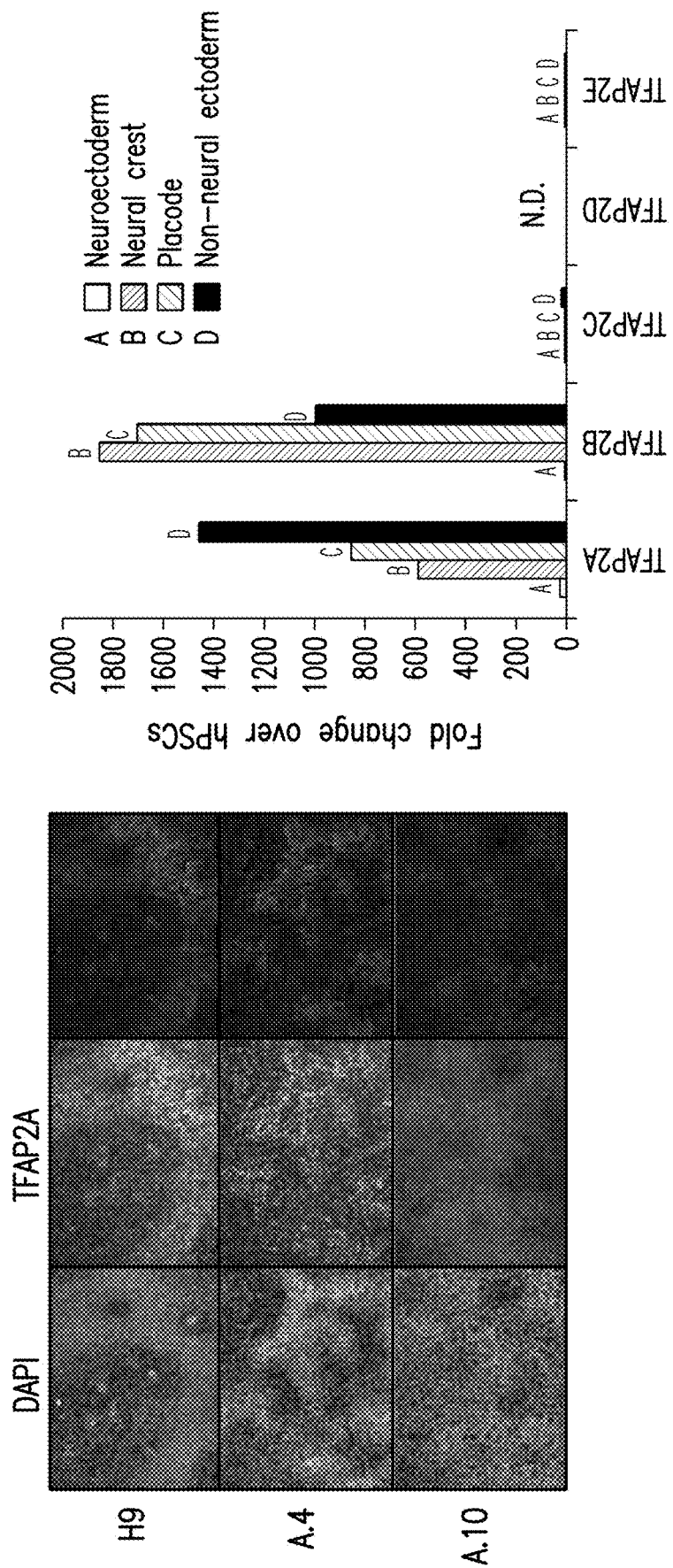

FIGS. 12A-12C Shows the generation of TFAP2A knockout hESCs using the CRISPR/Cas9 system. (A, B) Two guide RNAs were used to induce frame shift deletions in TFAP2A, and positive clones were sequenced to determine the extent and the nature of the deletion. FIG. 12A discloses SEQ ID NO: 1. FIG. 12B discloses SEQ ID NOS 2-8 in order of appearance. (C) Ablation of TFAP2A expression was confirmed using a short 3-day induction in the presence of high BMPs, which failed to elicit TFAP2A expression, compared to wild-type cells.

Figure 13A:
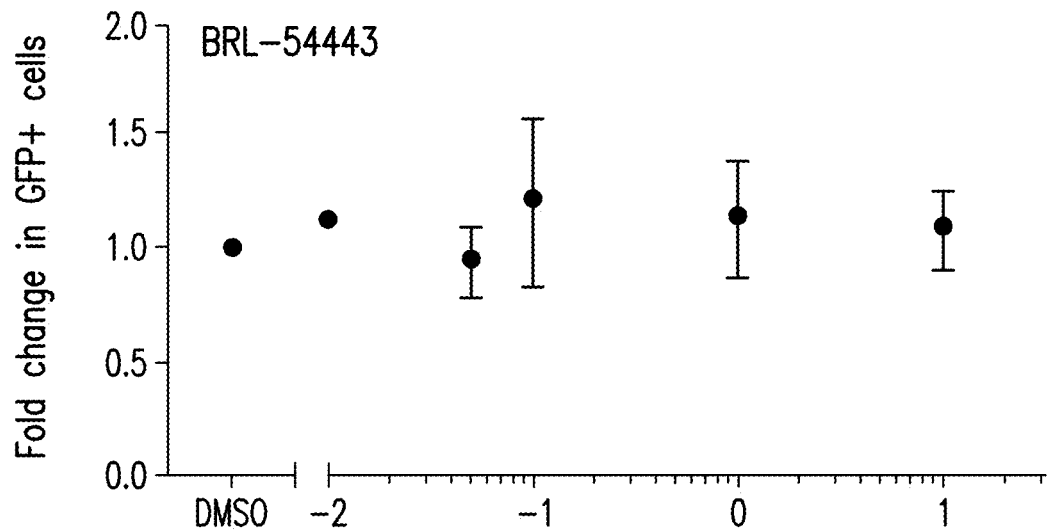
Figure 13B:
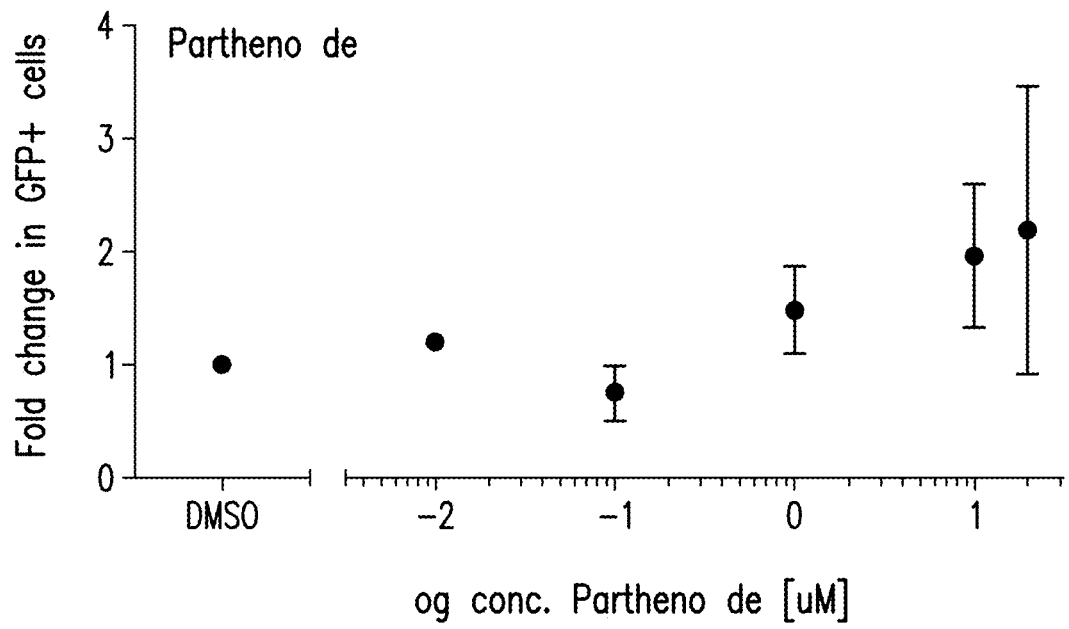

FIGS. 13A-13B Shows that (A) BRL-5443 and (B) Parthenolide increased the level of SIX1 expressing CP precursor cells differentiated from hESCs using the CP protocol.

Figure 14A:
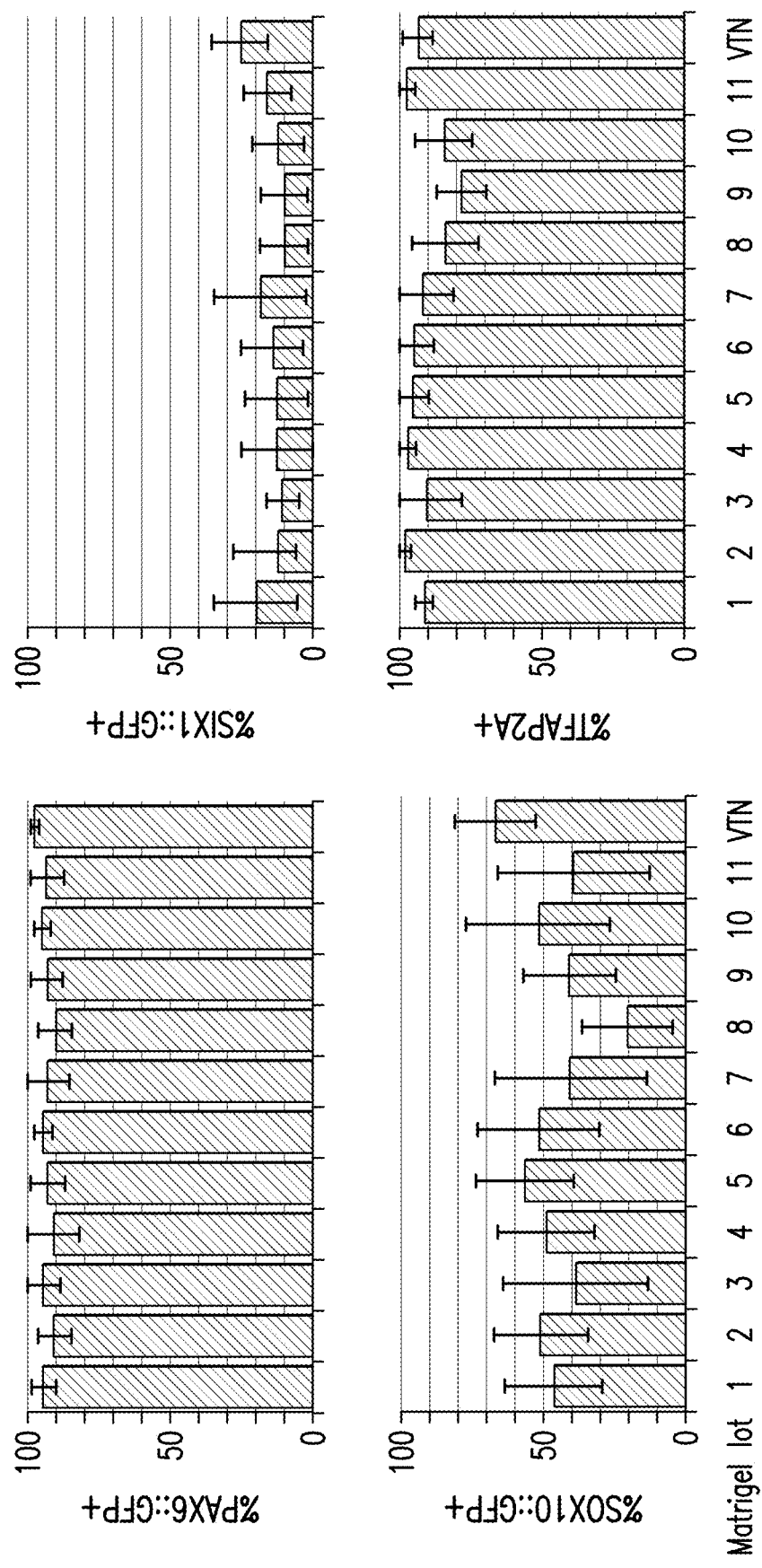

FIGS. 14A-14C Shows (A) that both Matrigel substrate (a coating substrate composed of thousands of proteins) and Vitronectin substrate (a coating substrate composed of a single recombinant protein) yielded highly robust induction efficiencies. Differentiations using 50,000 to 300,000 cells/$cm^2$ using both Matrigel (B) and Vitronectin (C) did not affect cell fate determination.

Figure 15A:
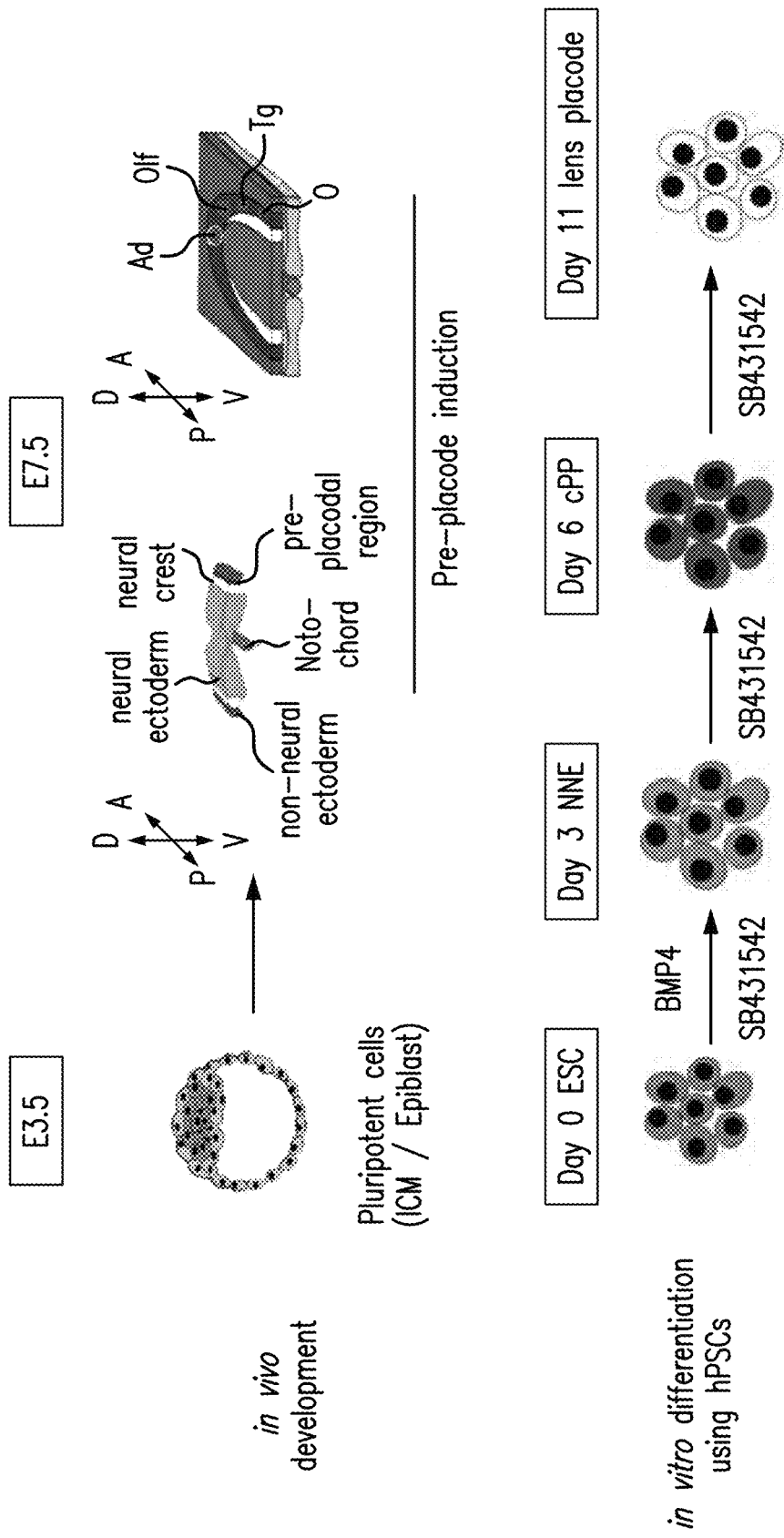
Figure 15B:
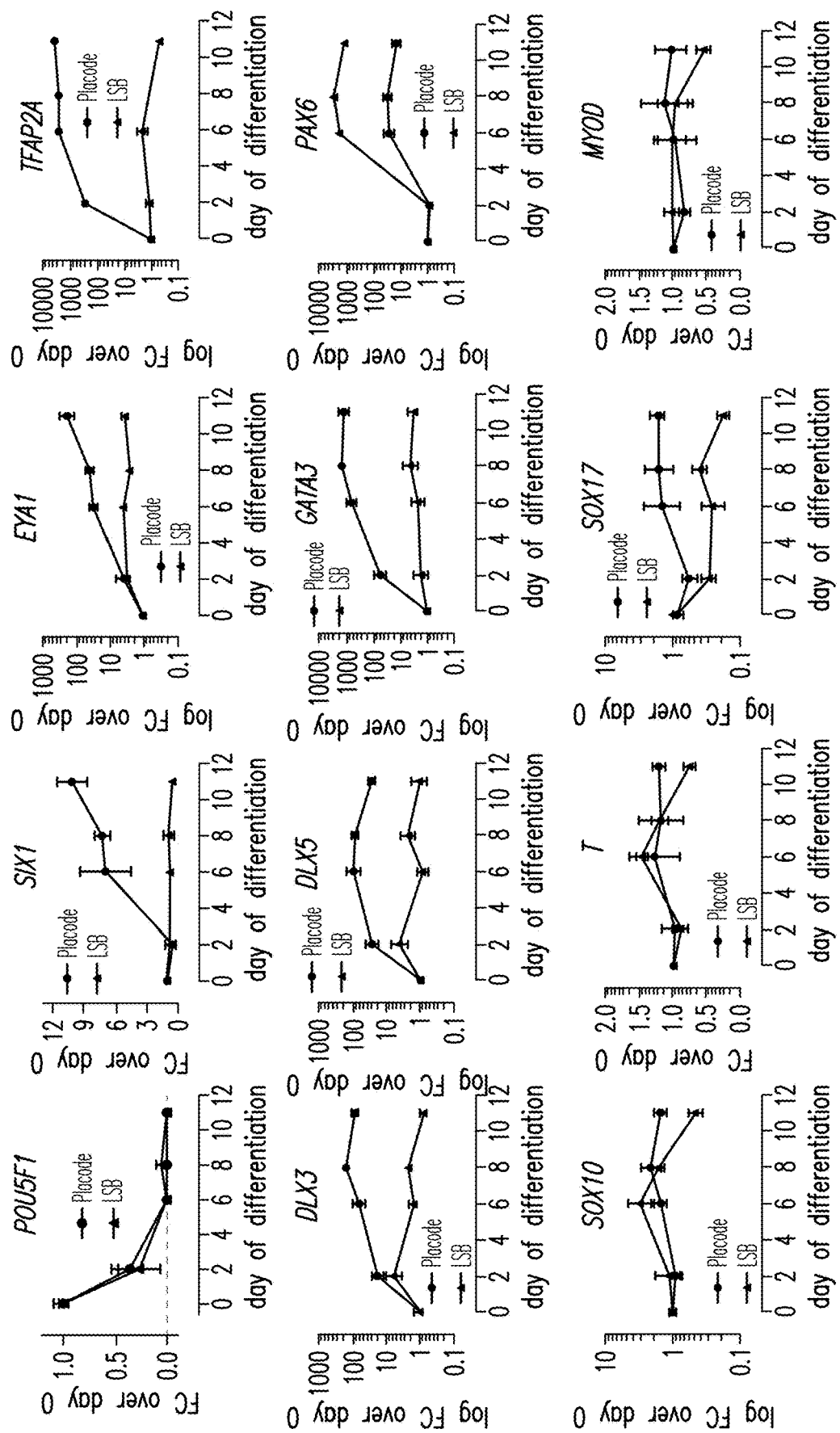
Figure 15C:
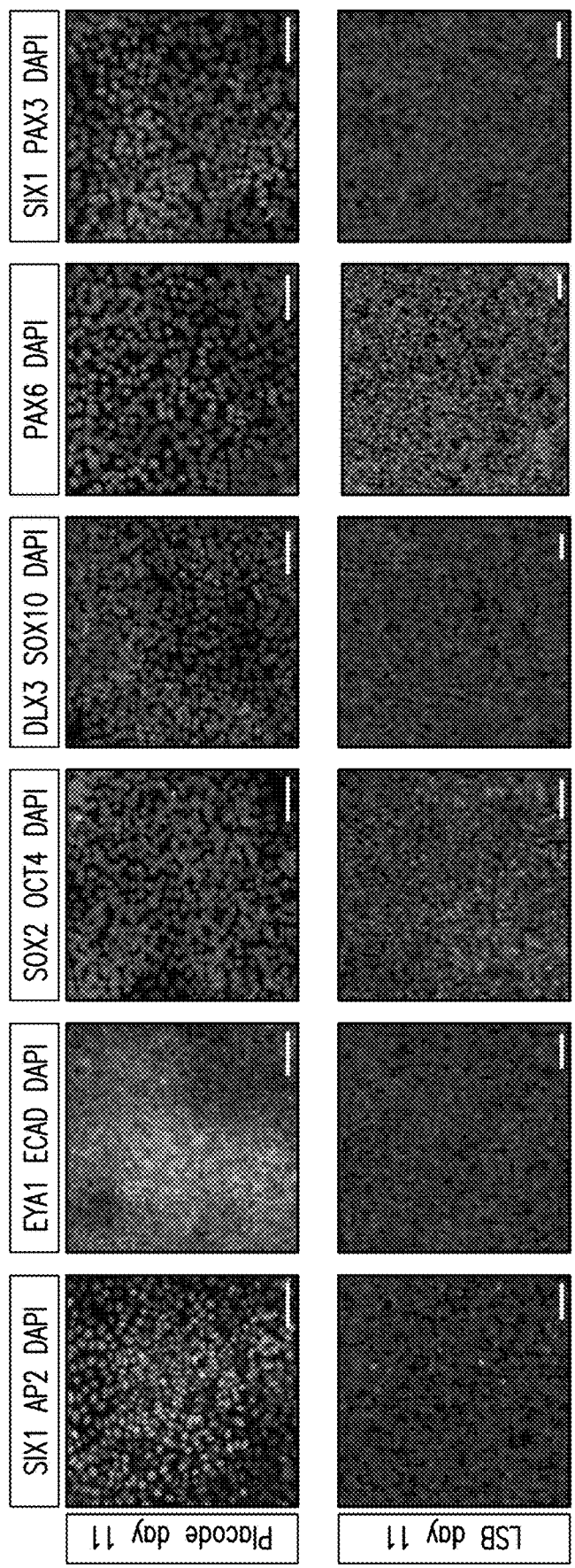

FIGS. 15A-15C Shows Differentiation of hPSCs into cranial placode using chemically defined conditions. (A) Schematic representation of cranial placode in vivo development and protocol for directed differentiation of human pluripotent stem cells. (B) Real-time PCR gene expression time course of key cranial placode (SIX1, EYA1), non-neural ectoderm (TFAP2A, DLX3/5, GATA3) genes as well as genes probing for potential contaminates (SOX10, T, SOX17, MYOD). Values are normalized to GAPDH and expression on day 0 of differentiation (right before switch to differentiation medium) and plotted as mean±SEM from 4 independent differentiations. (C) Immunofluorescence analysis comparing protein expression on day 11 of cranial placode induction protocol and LSB (neuroectoderm). Scale bars: 50 μm.

Figure 16A:
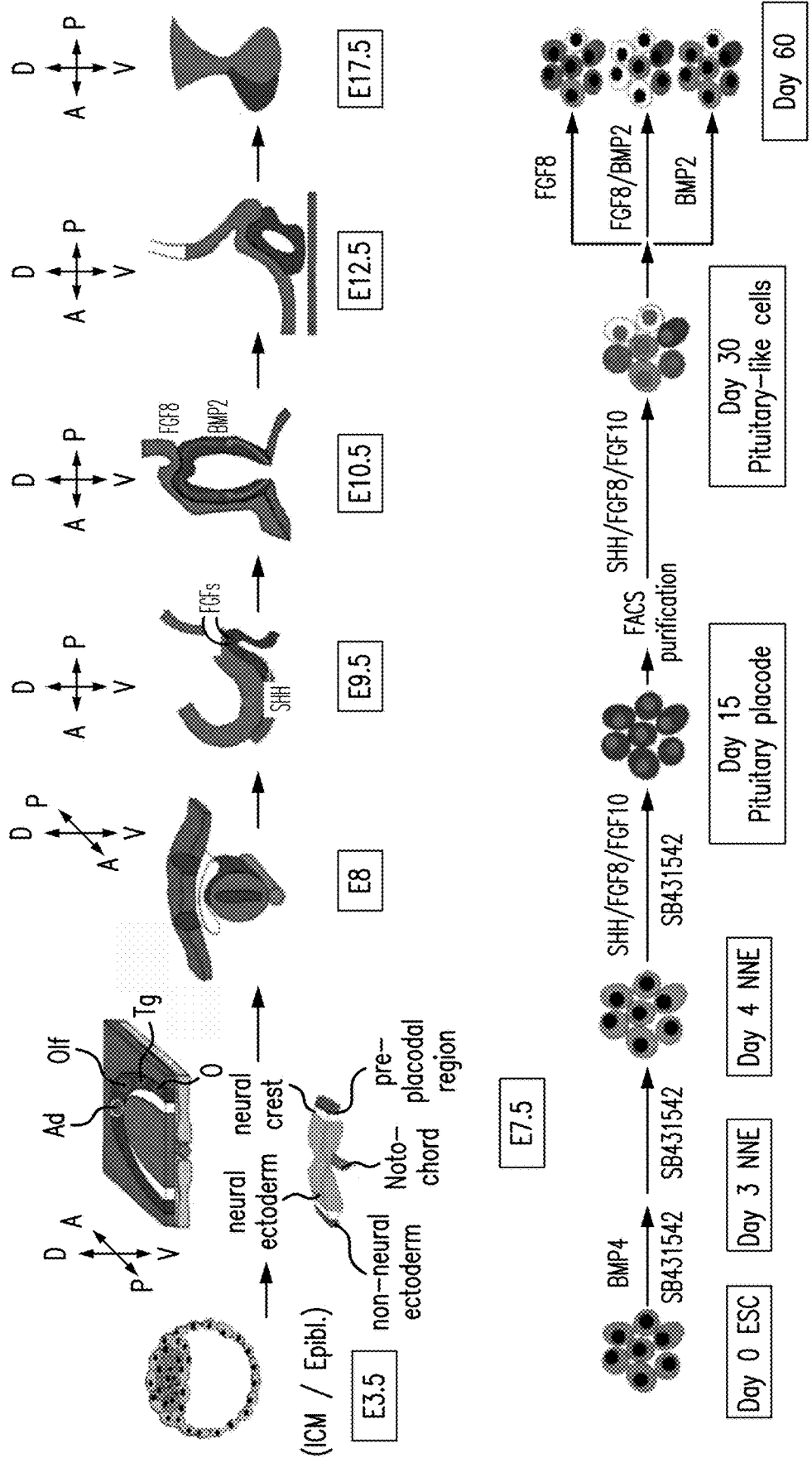
Figure 16B:
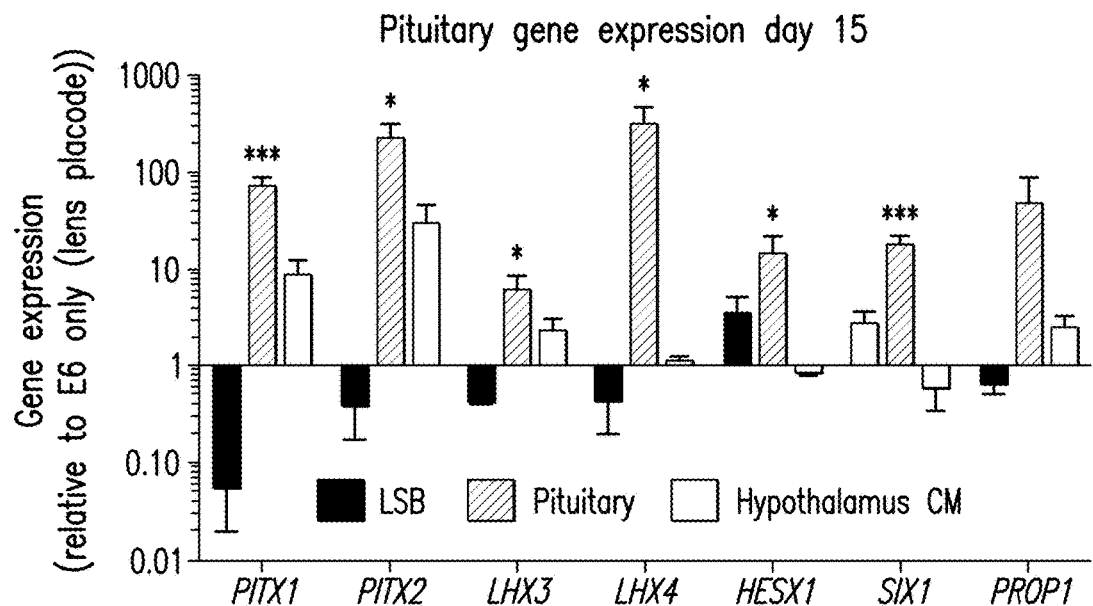
Figure 16C:
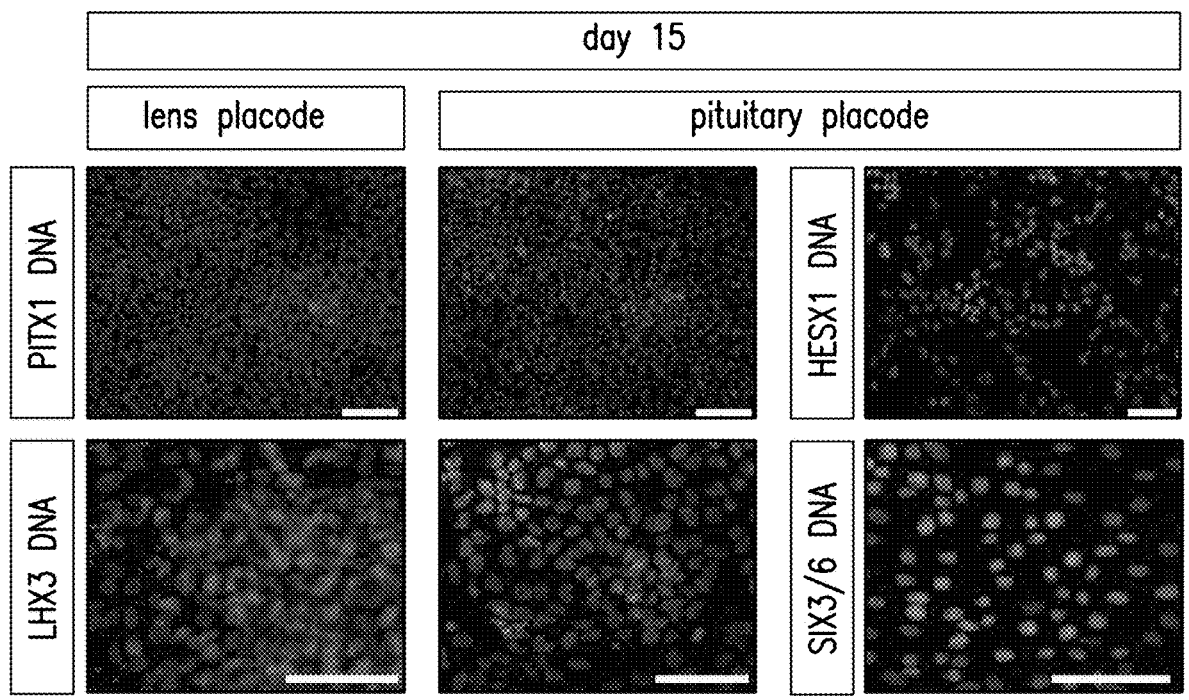

FIGS. 16A-16C Shows pituitary specification of anterior cranial placode derived hPSCs. (A) Schematic representation of pituitary gland in vivo development and protocol for directed differentiation of human pluripotent stem cells into anterior pituitary-like cells. (B) Real-time PCR analysis comparing expression of key genes involved in pituitary development in LSB, Pituitary condition and medium conditioned by hypothalamic neuroectoderm (Hypothalamus CM) after 15 days of differentiation in the respective medium. Values are normalized to GAPDH and gene expression on day 15 of lens differentiation (E6 only) and plotted as mean±SEM of at least 4 independent experiments. *: $p<0.05$, : $p<0.01$, *: $p<0.001$ compared to E6 only condition on day 15. (C) Immunofluorescence analysis comparing expression of PITX1, LHX3 after 15 days of differentiation under lens or pituitary conditions as well as expression of HESX1 and SIX3/6 on day 15 of pituitary differentiation. Scale bars: 50 μm.

Figure 17A:
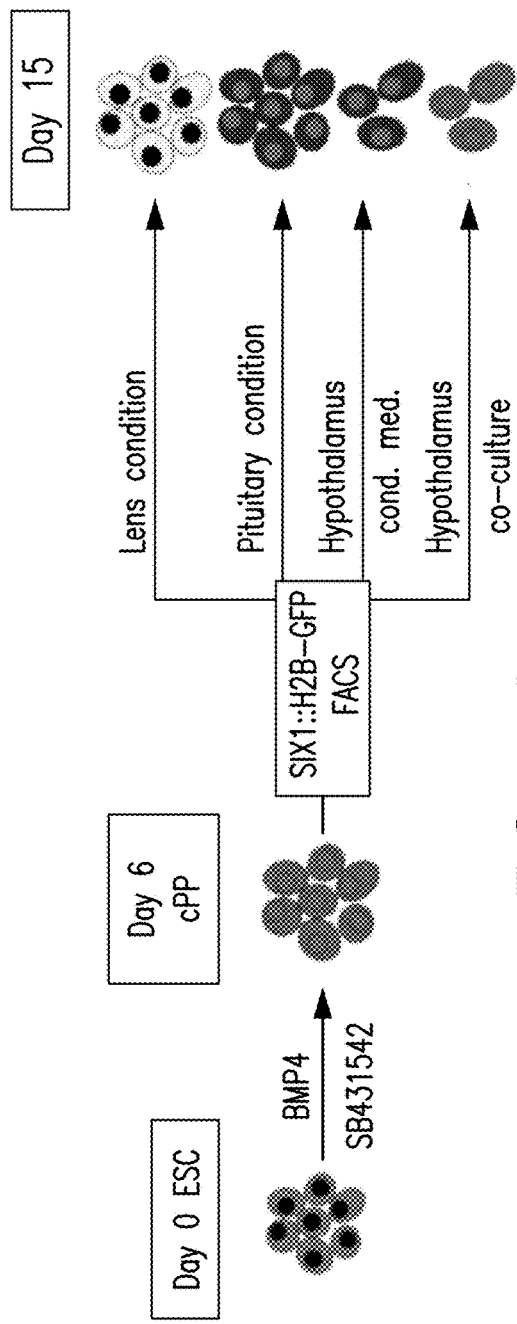
Figure 17B:
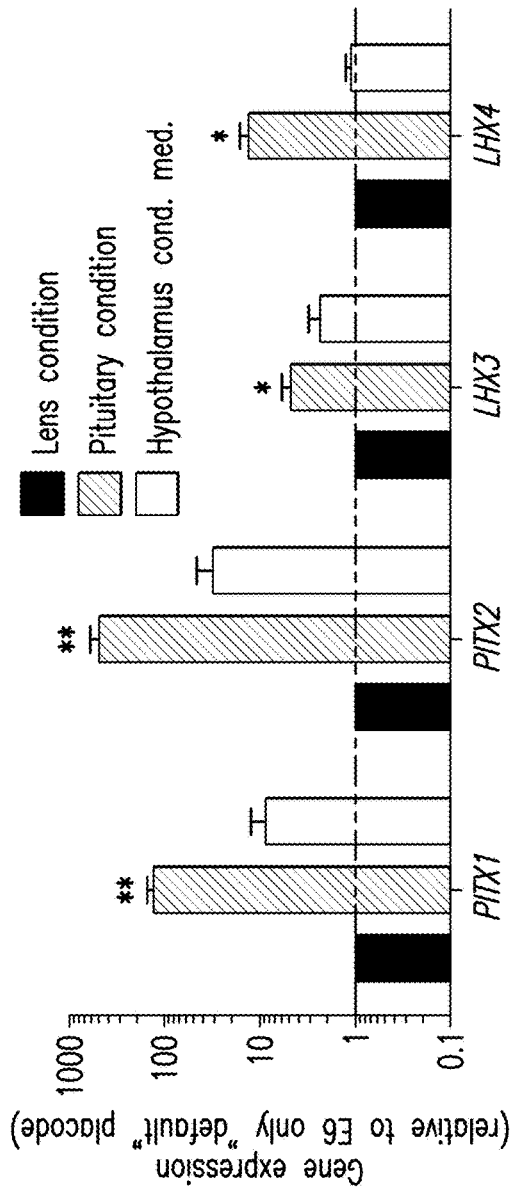
Figure 17C:
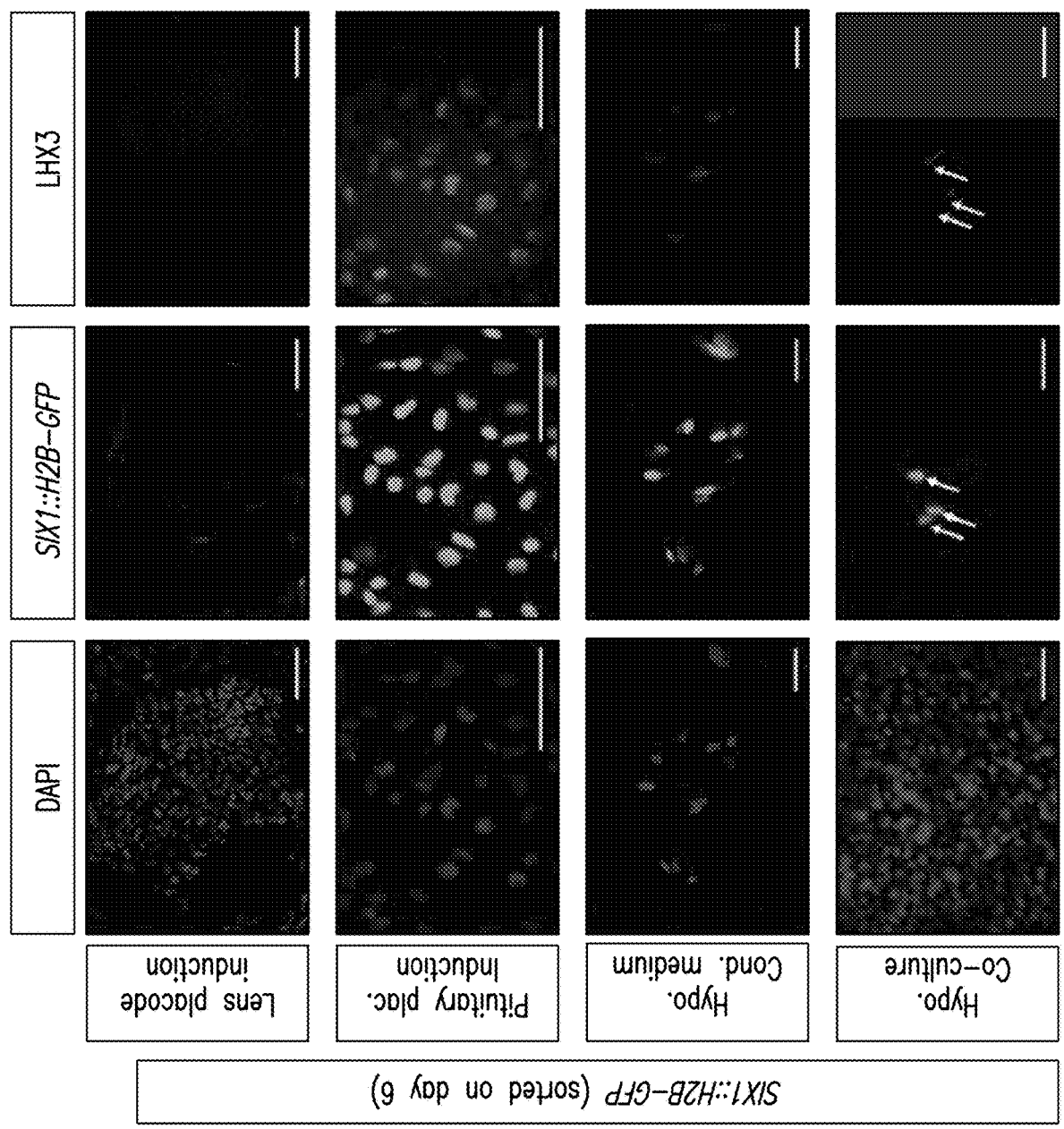

FIGS. 17A-17C Shows pituitary placode induction from unpatterned SIX1 purified cells. (A) Schematic representation of the experimental outline. hESC were differentiated under default conditions for 6 days. Unpatterned SIX1+ cells were FACS purified and cultured for additional 9 days in various conditions. Cells were analyzed on day 15. (B) Gene expression analysis of key pituitary genes in cells grown in 3 conditions described in A. Values are normalized to GAPDH and gene expression on day 15 of lens differentiation (E6 only) and plotted as mean±SEM of at least 4 independent experiments. *: $p<0.05$, **: $p<0.01$ compared to E6 only condition on day 15. (C) Immunofluorescence analysis of SIX1 sorted cells after 9 days of differentiation in respective medium condition. Arrows indicated absence of LHX3 expression in SIX1+ cells in co-culture condition. Scale bars: 50 μm.

FIGS. 18A-18E Shows functional characterization of anterior pituitary cells. (A) Immunofluorescence analysis of anterior pituitary cells after 30 days of differentiation. On day 30 the culture contains corticotrophs (ACTH), somatotrophs (GH) and gonadotrophs (FSH, LH). Scale bar: 50 μm. (B) In vitro basal hormone release on day 30 of differentiation as assessed by ELISA. Data is plotted as mean±SEM of 3 independent experiments. *: $p<0.05$, *: $p<0.001$, **: $p<0.0001$ compared to no cells (differentiation medium only). (C-E) Quantification of hormone levels after 24 h of in vitro stimulation using compounds triggering hormone release. ACTH release was specifically induced by CRF, Stressin or Urocortin and not by Somatocrinin or Ghrelin (C), GH release was induced by Somatocrinin but not CRF (D) and FSH release was induced by Nafarelin (E). Data is plotted as mean±SEM of 3 independent experiments. *: $p<0.05$ compared to the solvent control.

FIGS. 19A-19E Shows temporal single cell qRT-PCR analysis of anterior pituitary development in vitro. (A,B) Principal component analysis of single cells on day 30 (black) and day 60 (gray) of differentiation reveals two distinct populations of cells. (C) Unsupervised hierarchical clustering of day 30 and day 60 cells using 34 different primer pairs identifies 2 clusters of cells with very few leading cells (day 30 cells resembling day 60 cells) and cells lacking behind (day 60 cells still more closely resembling day 30). (D) Quantification of hormone expressing cells on day 30 and day 60 as well as percentage of cells expressing more than 1 hormonal transcript per cell. (E) Expression of individual hormones per single cell on day 30 and day 60 respectively.

FIGS. 20A-20E Shows specification of hormonal cells of the pituitary in vitro. (A) Bulk qRT-PCR analysis of day 60 cells patterned with FGF8, FGF8/BMP2 or BMP2 for 30 days. Patterning with BMP2 induced a more ventral cell identity (PIT1, GATA2, GH1, FSHB and LHB) while FGF8 suppressed dorsal cell types (FSHB). Data is plotted as mean±SEM of 2-4 independent experiments. *: $p<0.05$, : $p<0.01$, *: $p<0.001$ compared to the "default" pituitary differentiation on day 60. (B) Unsupervised hierarchical clustering of FGF8, FGF8/BMP2 and BMP2 patterned cells using 34 primer pairs identified 3 larger clusters of cells with cluster 2 mainly comprised of cells patterned by FGF8 (or FGF8/BMP2) and cluster 3 mainly comprised of cells patterned by BMP2 (or FGF8/BMP2). (C) Quantification of hormonal transcripts per cell in different patterning conditions. Data is plotted as percentage of cells expressing the respective transcript (ct<35 cycles in combination with a proper melting curve). (D) Immunofluorescence analysis (representative images) of hormone expression in cells patterned with FGF8, FGF8/BMP2 or BMP2 on day 60 of differentiation. Scale bars: 50 μm. (E) Quantification of hormone expressing cells (per subtype) in different patterning conditions on day 60 of differentiation. High levels of FGF8 induced dorsal fate (ACTH) while intermediate levels of FGF8 and BMP2 induced dorsal/ventral fates (PRL and GH) compared to the default condition (E6 only). Data is plotted as mean±SEM of 2 independent experiments. *: $p<0.05$, **: $p<0.01$ compared to the "default" (E6 only) pituitary differentiation on day 60.

FIGS. 21A-21G Shows in vivo survival and function of hPSC-derived anterior pituitary cells. (A) Schematic representation of experimental layout. After surgical removal of the pituitary gland and confirmation of hypopituitarism, cells embedded in Matrigel were transplanted subcutaneously. (B-E) ACTH (B), GH (C), LH (D) and corticosterone (E) levels were quantified in serum for up to 7 weeks after transplantation of the cells using ELISA. Data is plotted as mean±SEM with each dot representing an individual animal. *: $p<0.05$, **: $p<0.01$ compared to the corresponding sham control. (F) Immunohistological analysis of grafts 7 weeks after transplantation. Cells for each of the 6 hormonal lineages of the anterior pituitary gland were detectable within the graft. Scale bars: 50 μm. (G) Quantification of cells expressing ACTH and the corresponding graft volume 7 weeks after transplantation. Data is plotted as mean±SEM with each dot representing an individual animal (3 animals total).

Figure 22A:
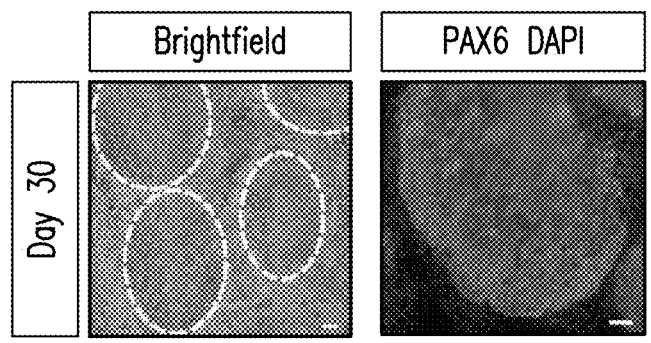
Figure 22B:
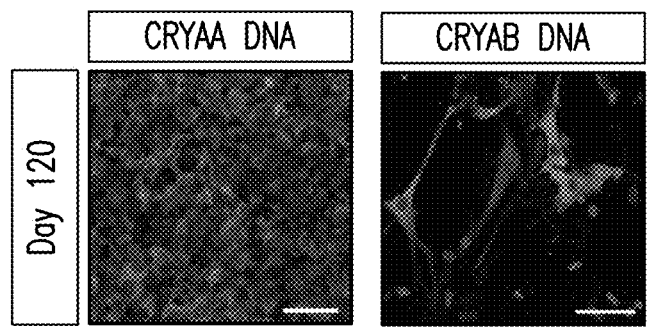
Figure 22C:
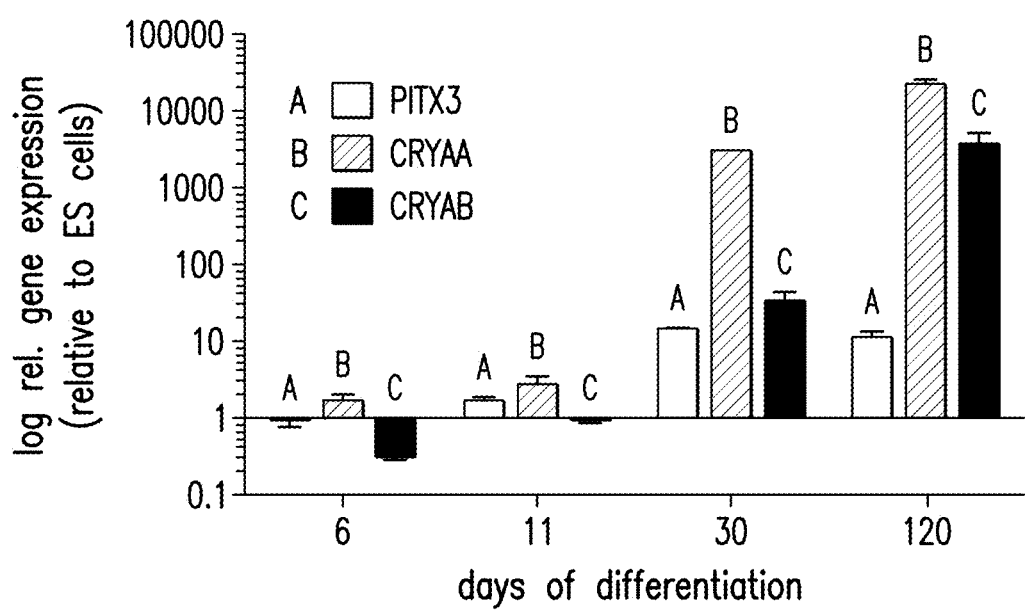

FIGS. 22A-22C Shows "default" conditions in chemically defined media result in lens placode specification. (A) After 30 days of differentiation under "default" conditions (E6 only) lentoid bodies (circled structures in brightfield image) staining positive for the lens marker PAX6 are clearly identifiable. Scale bars: 50 μm. (B) After an additional 90 days of differentiation (day 120) the majority of the cells is expressing crystallin the predominant structural proteins in the lens. Scale bars: 50 μm. (C) qRT-PCR gene expression time course during lens differentiation. Cells differentiated for 120 days express the lens characteristic transcripts PITX3, CRYAA and CRYAB. Values have been normalized to GAPDH and expression in undifferentiated ES cells and are plotted as means+/−SEM of 4 independent consecutive experiments.

Figure 23A:
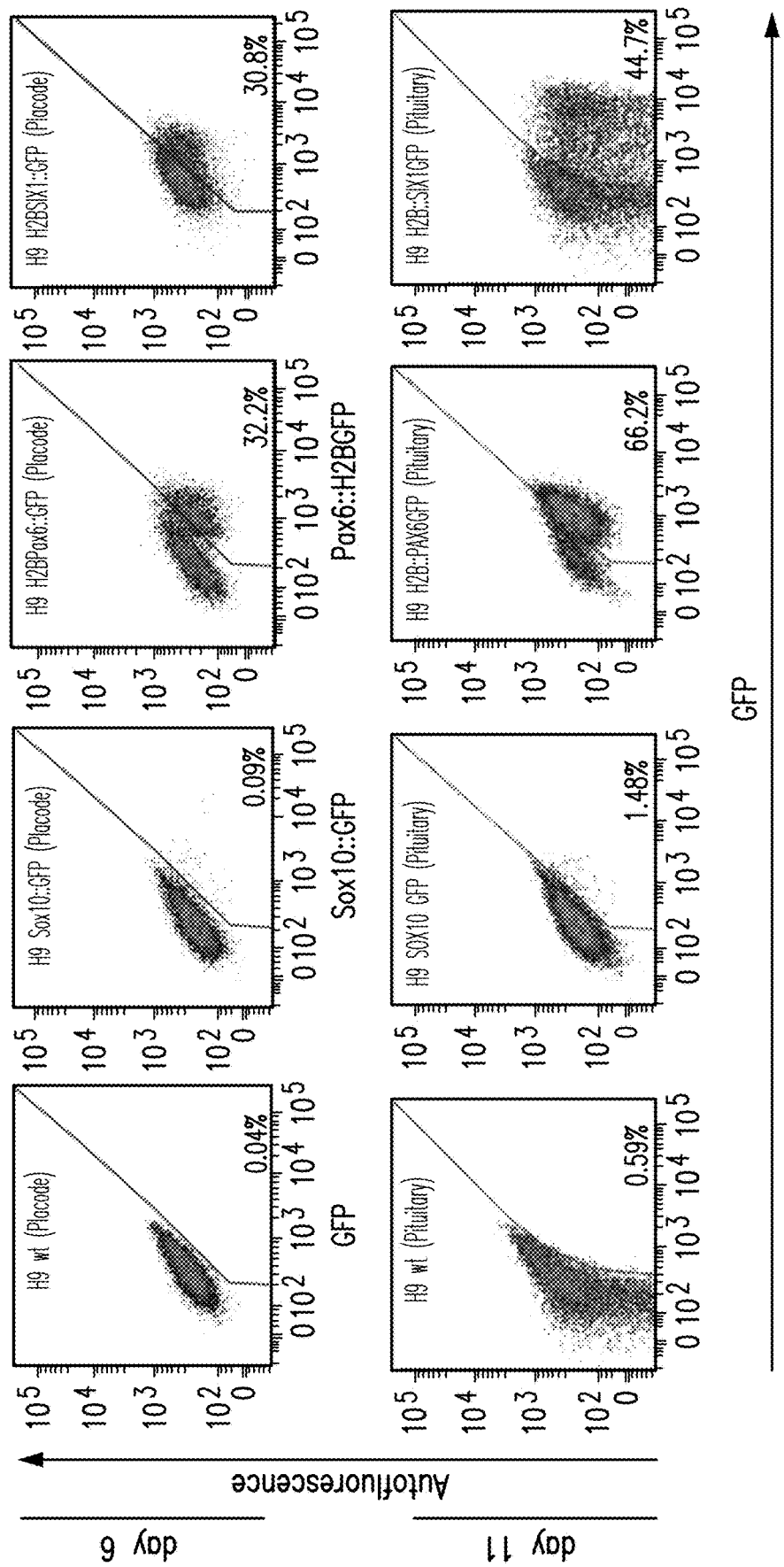
Figure 23B:
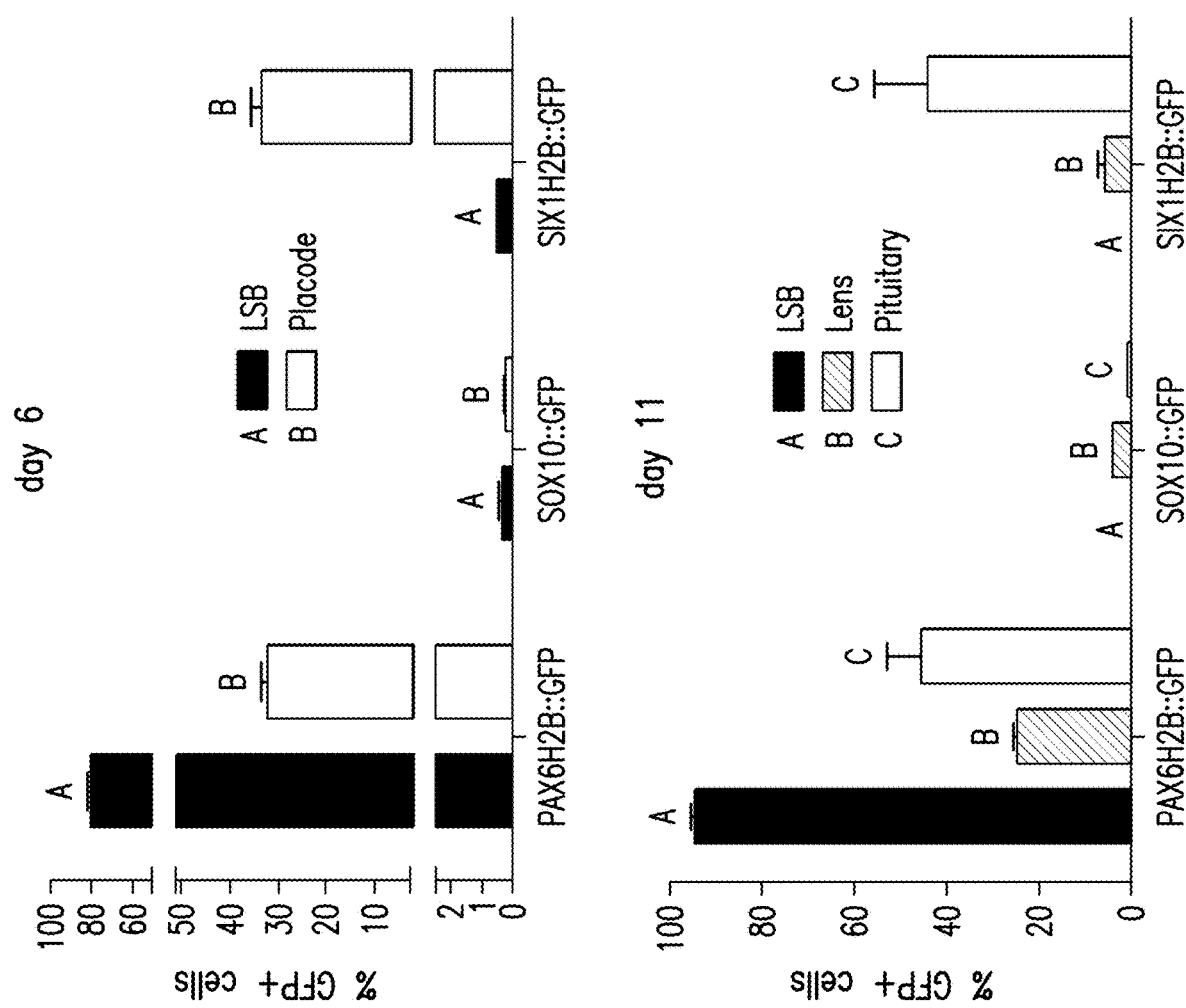

FIGS. 23A-23B Shows quantification of ectodermal subtypes within the pituitary differentiation using reporter cell lines. (A) Cells (different reporter cell lines) differentiated for 6 and 11 days under either default placode or pituitary conditions were analyzed using Flow Cytometry for SOX10, PAX6 or SIX1 expression. Representative Flow Cytometry plots with percentages are shown. (B) Quantification of data form (A) reveals very few contaminating neural crest cells (SOX10+) while confirming the anterior cranial placode character of the cells (SIX1+, PAX6+). Data is plotted as mean±SEM of 2-8 independent experiments.

Figure 24A:
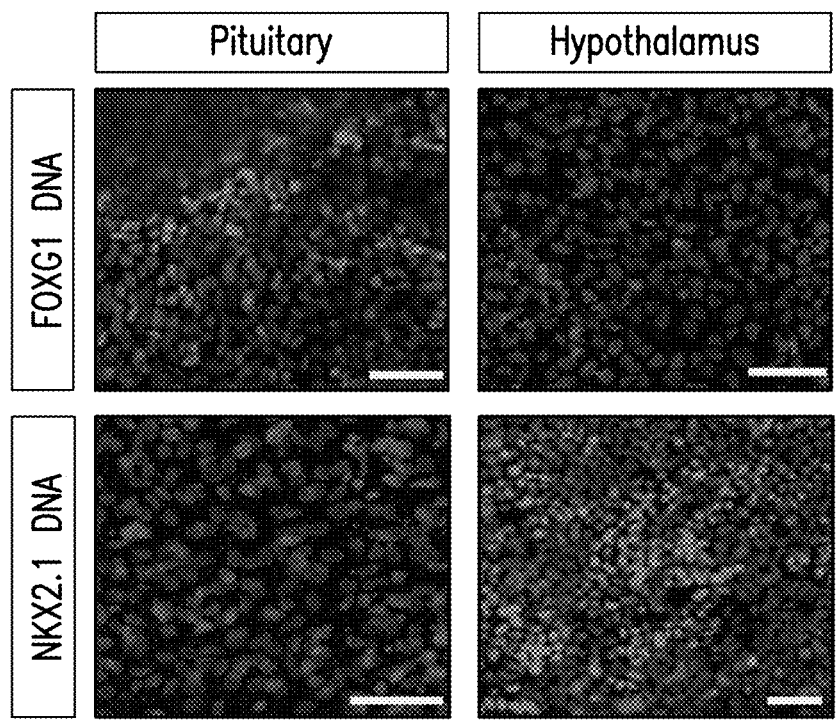
Figure 24B:
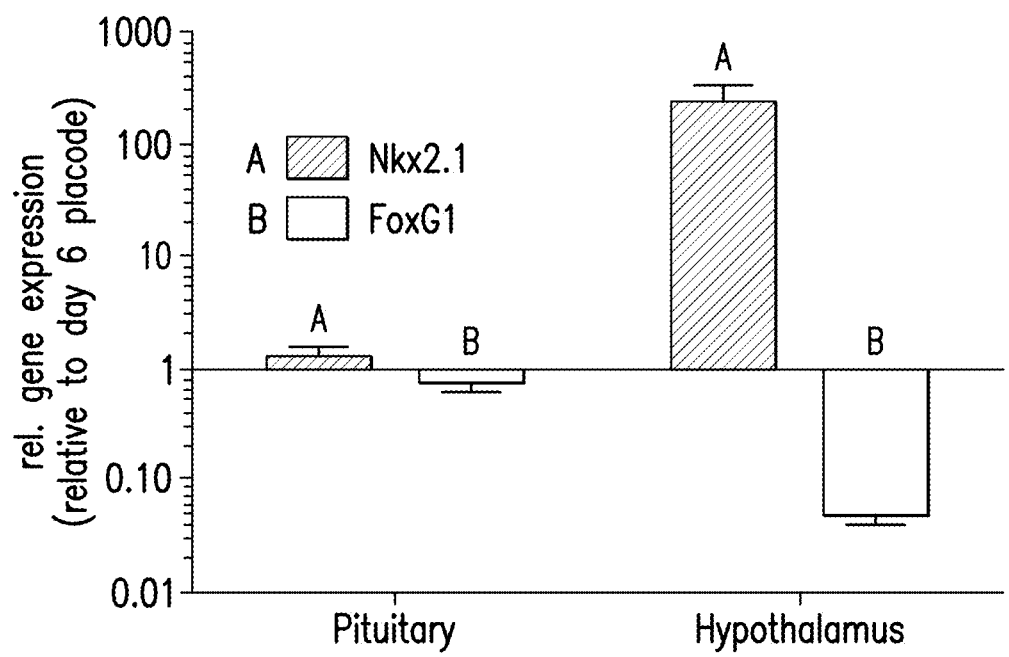

FIGS. 24A-24B Shows differentiation of hESCs into hypothalamic ectoderm. (A) Immunofluorescence comparison of cells differentiated for 15 days under either pituitary or hypothalamus condition. Cells were stained for either FOXG1 (Pituitary) or NKX2.1 (Hypothalamus). Scale bars: 50 μm. (B) qRT-PCR analysis of day 15 cells differentiated under pituitary or hypothalamic ectoderm condition probing for NKX2.1 and FOXG1. Values have been normalized to GAPDH and expression in day 6 placode cells and are plotted as means+/−SEM of 2-4 independent experiments.

Figure 25A:
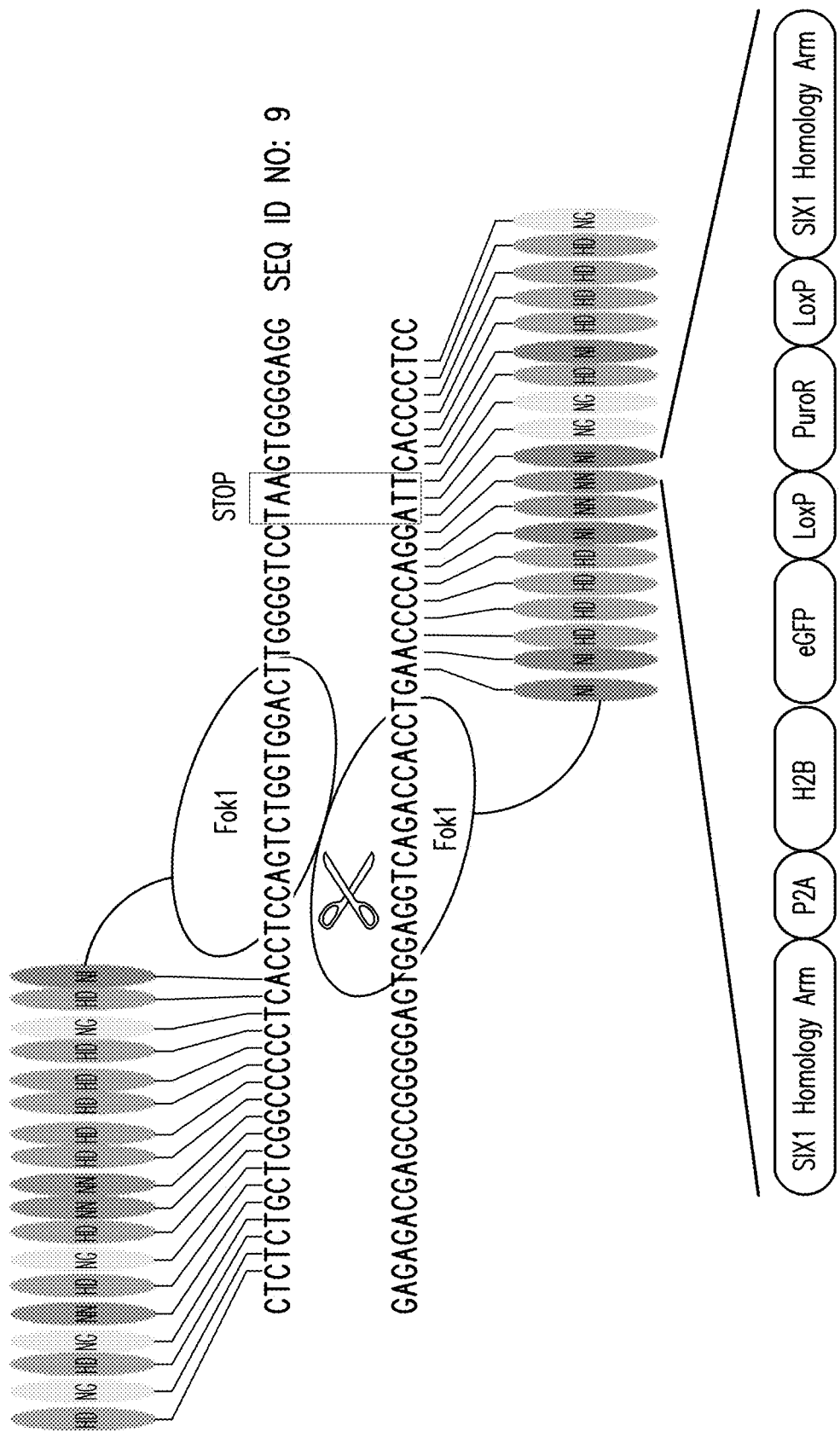
Figure 25C:
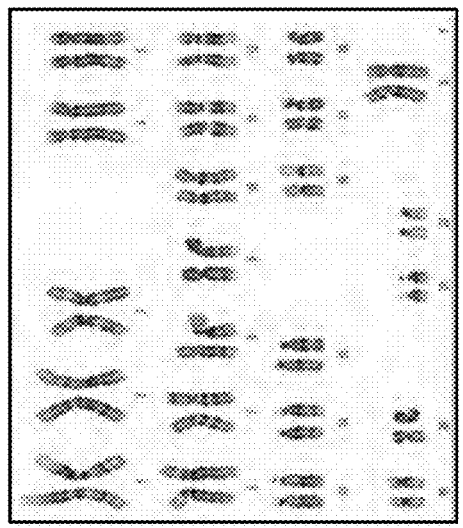
Figure 25E:
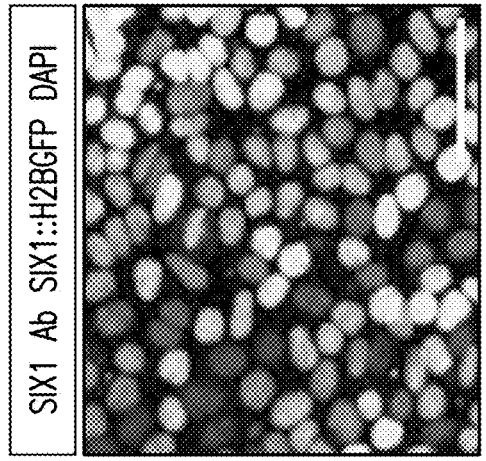
Figure 25B:
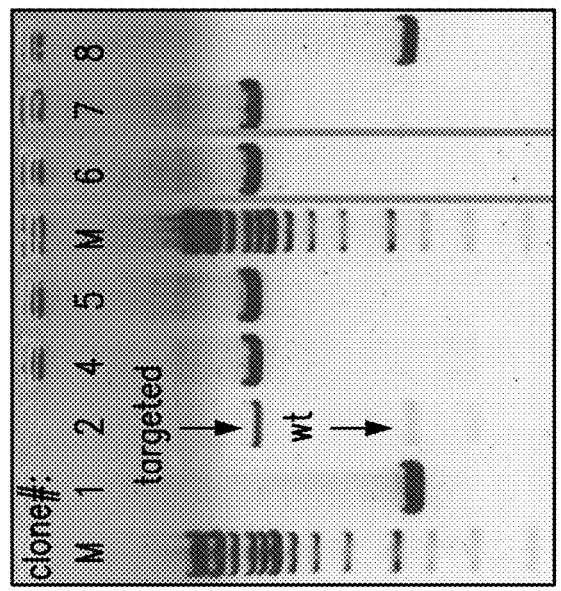
Figure 25D:
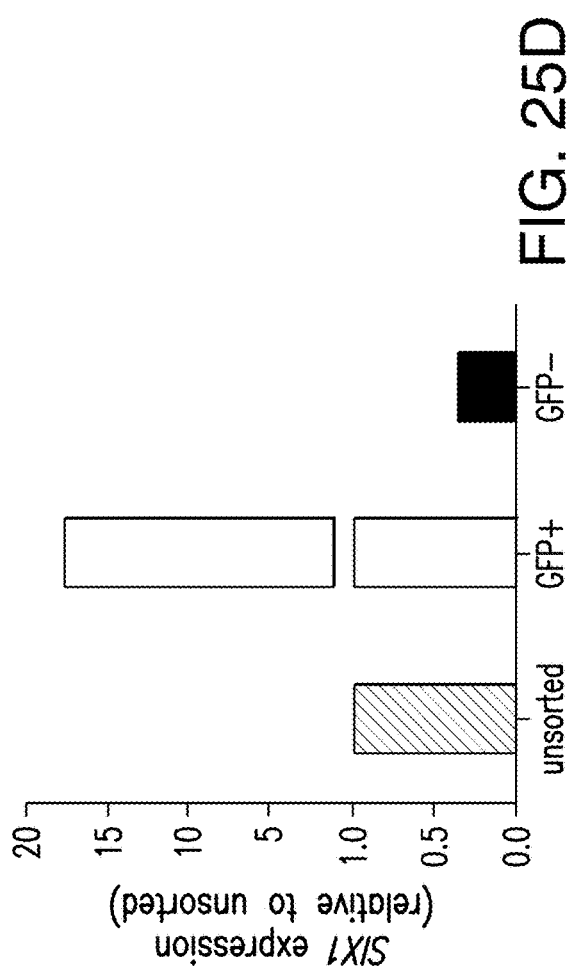

FIGS. 25A-25E Shows generation of the SIX1 knock-in reporter line. (A) Schematic representation of the TALEN-based targeting of the endogenous SIX1 Stop codon using an eGFP containing reporter cassette. FIG. 25A discloses SEQ ID NO: 9. (B) PCR screening of targeted clones using primers annealing to the genomic region just outside the SIX1 homology arms. Clone #6 was selected and used in the study. (C) Karyogram of H9 SIX1H2B::GFP clone #6 showing a normal female (XX) karyotype. (D) qRT-PCR analysis of SIX/expression in SIX1H2B::GFP cells differentiated for 6 days under placode conditions sorted positively and negatively for GFP. Values are normalized to GAPDH and unsorted cells from the same experiment and are plotted as means+/−SEM of a single experiment with 2 technical replicates. (E) Immunofluorescence analysis of day 11 pituitary cells staining for endogenous SIX1 (red) and GFP under the control of the endogenous SIX1 promoter (green). Scale bar: 50 μm.

Figure 26:
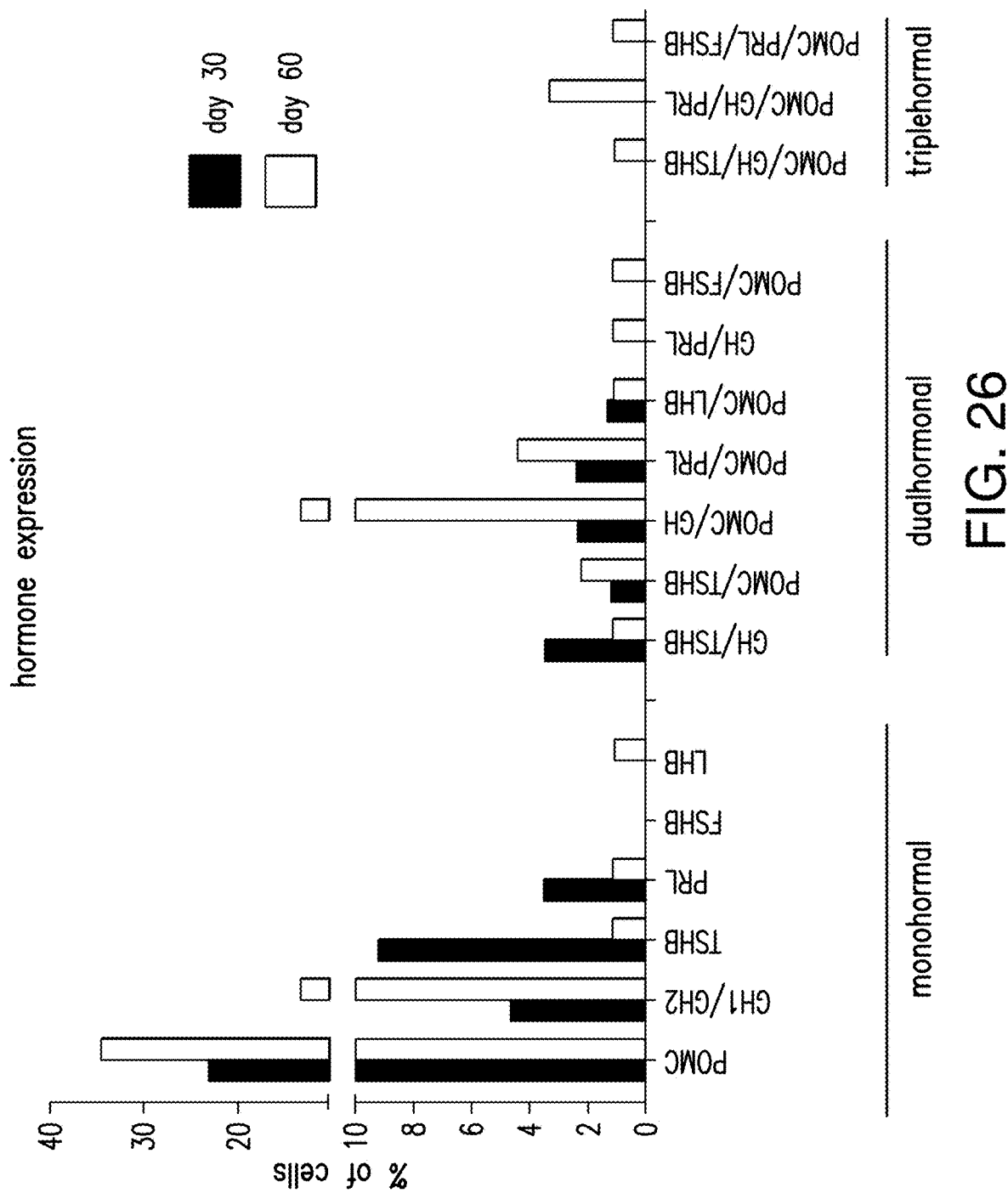

FIG. 26 Shows quantification of hormonal transcripts in single cells using single cell qRT-PCR. Single cell PCR data from day 30 and day 60 of the "default" pituitary differentiation protocol were mined for cells expressing at least one hormonal transcript. Data is plotted as percentage of cells expressing the respective transcript(s) (ct<35 cycles in combination with a proper melting curve).

FIG. 27 Shows the list of primers used in the single cell qRT-PCR experiments of Example 2. FIG. 27 discloses "FP" sequences as SEQ ID NOS 10-43 and "RP" sequences as SEQ ID NOS 44-77, all respectively, in order of appearance.

FIG. 28 Shows the list of antibodies used in Example 2.

Figure 29A:
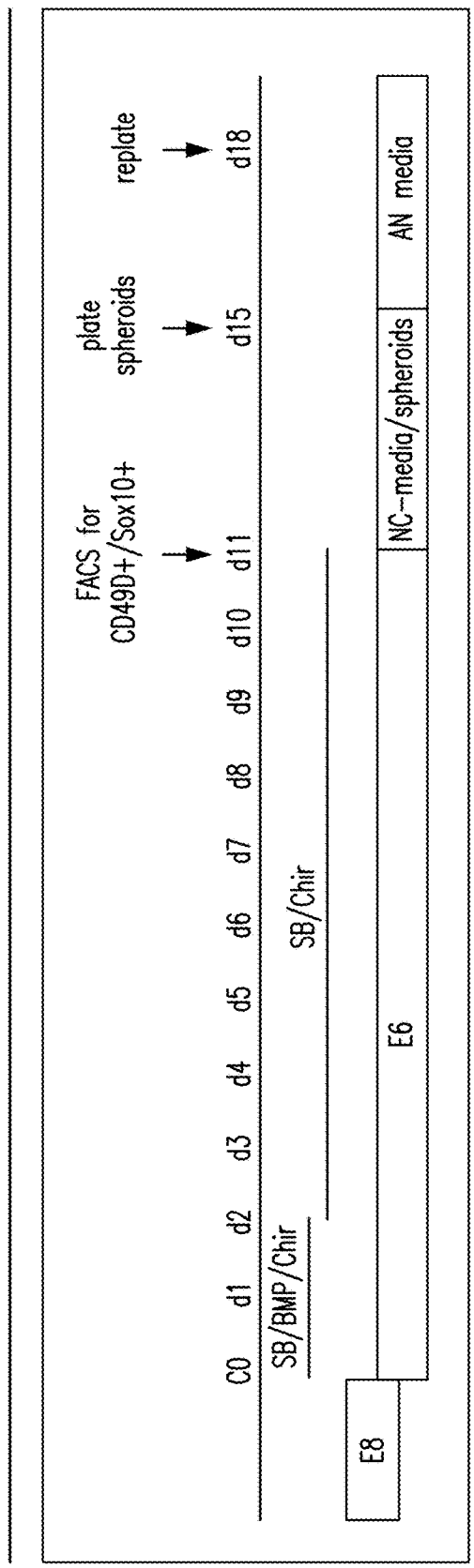
Figure 29B:
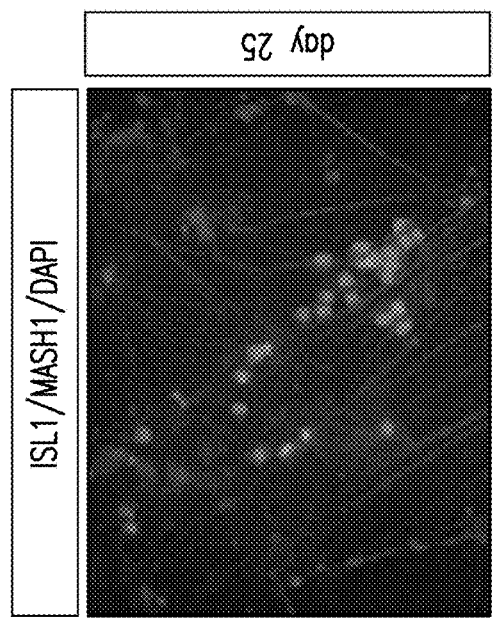

FIGS. 29A-29B Shows differentiation of pluripotent cells into neural crest derived cells. (A) Pluripotent cells were cultured in E6 media supplemented with SB431542, BMP4 and CHIR99021 for two days (i.e., from d0 to d2 of culture in E6 media), and in E6 media supplemented with SB431542 and CHIR from d2 to d11, to differentiate into neural crest progenitor cells. (B) The neural crest progenitors spontaneously differentiated into cells expressing MASH1 and ISL1 at d25.

Figure 30A:
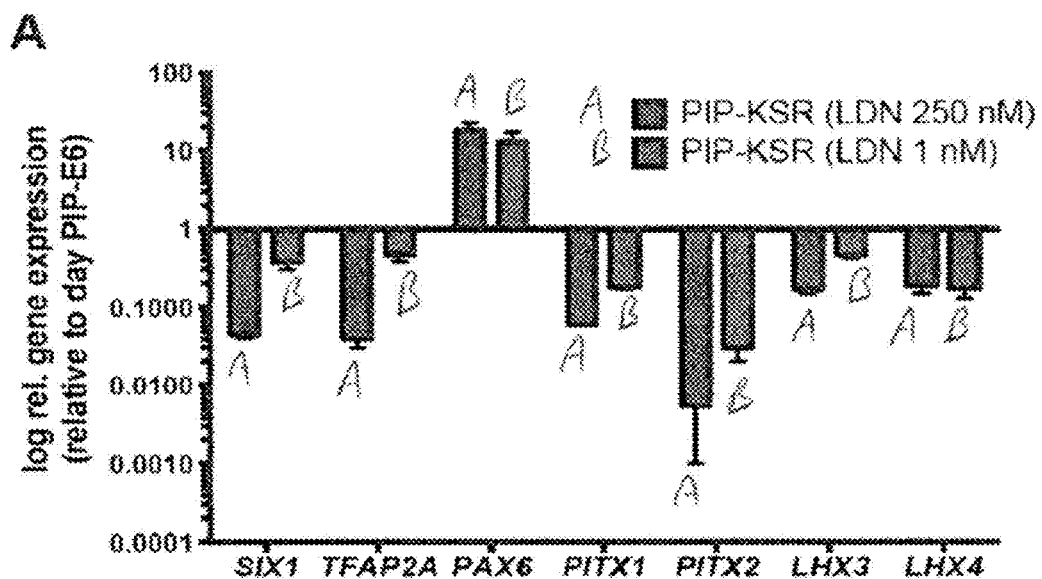
Figure 30B:
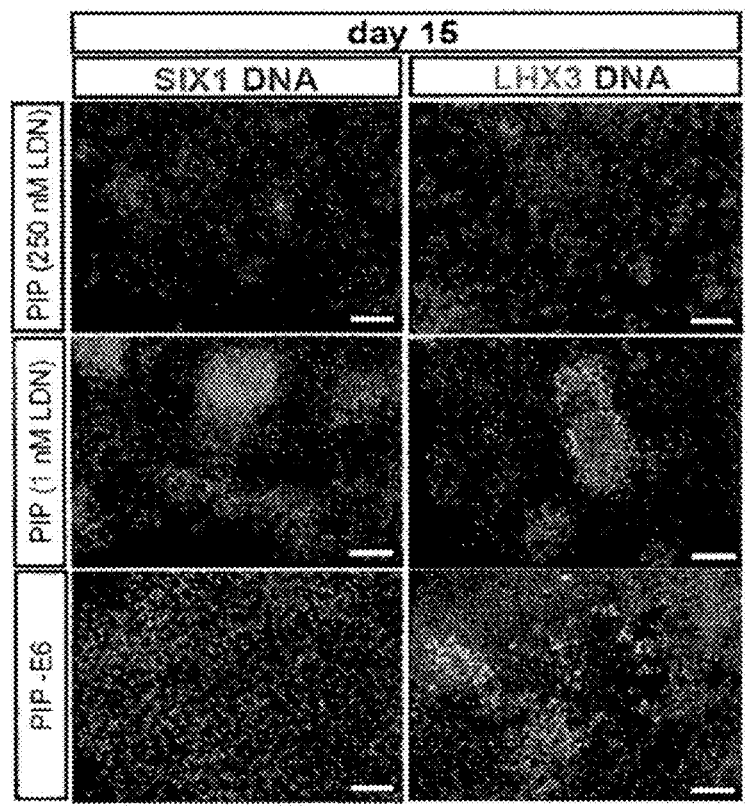

FIGS. 30A-30B Shows comparison of the traditional KSR-based pituitary induction with the new cGMP-ready induction. Cells grown on feeders in KSR-based medium were differentiated using the old Dincer et. al. protocol (PIP-KSR). To compensate for KSR lot-to-lot variation 2 concentrations of LDN-193189 were used. Cells grown under feeder-free Essential8 conditions using the PIP-E6 protocol were differentiated in parallel. (A) qRT-PCR analysis of day 15 cells differentiated under PIP-KSR and PIP-E6 condition probing for SIX1, TFAP2A, PAX6, PITX1, PITX2, PITX3 and PITX4. Values have been normalized to GAPDH and expression in day 15 PIP-E6 cells and are plotted as means+/−SEM of 2 independent experiments. (B) Immunofluorescence comparison of cells differentiated for 15 days under either PIP-KSR or PIP-E6 condition. Cells were stained for either SIX1 (pan placode) or LHX3 (pan pituitary). Scale bars: 50 μm.

FIGS. 31A-31E Shows cell line comparison of pituitary induction protocol in E8/E6 and replacing recombinant SHH with small molecule smoothened agonists. Four different hESC lines (including the H9 SIX1::H2B-GFP clone #6) and 1 hiPSC cell line were differentiated in parallel using the cGMP-ready pituitary induction protocol. (A) qRT-PCR analysis of day 15 cells differentiated under pituitary condition probing for the pan placodal marker SIX1 as well as the pan anterior pituitary genes PITX1, PITX2, LHX3 and LHX4. Values have been normalized to GAPDH and expression in day 30 wt H9 cells and are plotted as means+/−SEM of 2-4 independent experiments. (B) qRT-PCR analysis of day 30 cells differentiated under pituitary condition without sorting on day 15 probing for 2 anterior pituitary hormone transcripts POMC and GH1 Values have been normalized to GAPDH and expression in day 30 wt H9 cells and are plotted as means+/−SEM of 3 independent experiments. (C) Immunofluorescence analysis comparing protein expression on day 15 of pituitary placode induction across different hPSC lines. Scale bars: 50 μm. To investigate whether SHH can be replaced by small molecules, cells were differentiated using the cGMP-ready pituitary placode induction protocol using either recombinant SHH or one of the small molecule agonists purmorphamine or SAG in combination with FGF8 and FGF10. Lens placode differentiation was performed in parallel and served as a negative control. (D) qRT-PCR analysis of day 15 cells, differentiated under pituitary conditions using either SHH, purmorphamine or SAG from day 4 on, probing for the pan pituitary genes PITX1, PITX2, LHX3, LHX4, HESX1 as well as the hormone transcript POMC1 as well as the lens marker PITX3. Values have been normalized to GAPDH and expression in day 15 lens placode and are plotted as means+/−SEM of 3 independent experiments. (E) Immunofluorescence analysis comparing protein expression on day 15 of pituitary placode and lens induction using SHH and the small molecule alternatives purmorphamine and SAG. Early lentoid bodies (circled structures) start to downregulate expression of the pan placodal marker SIX1 while pituitary placode retains high SIX1 expression in combination with expression of LHX3. Scale bars: 50 μm.

Figure 32:
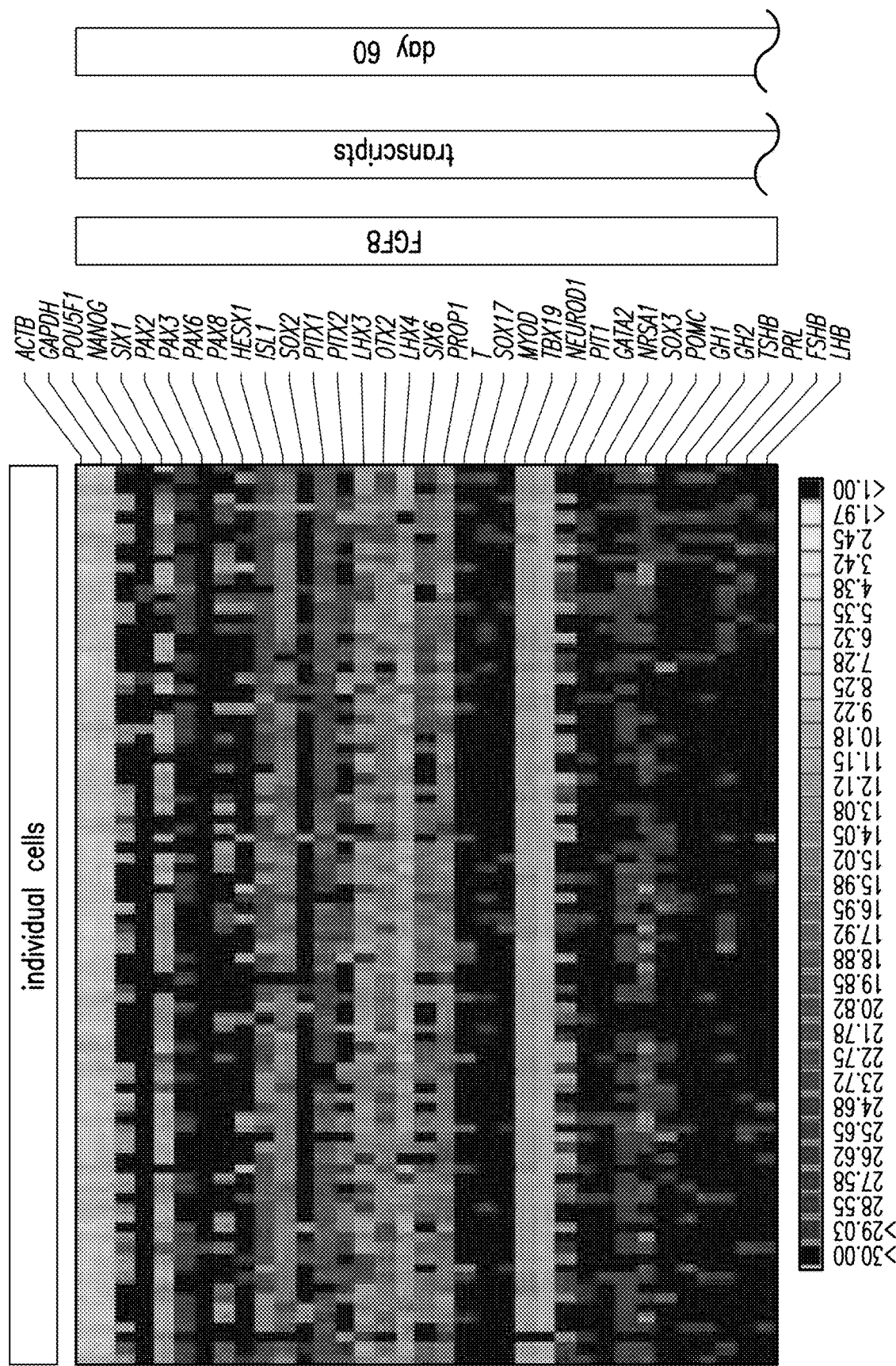
Figure 32:
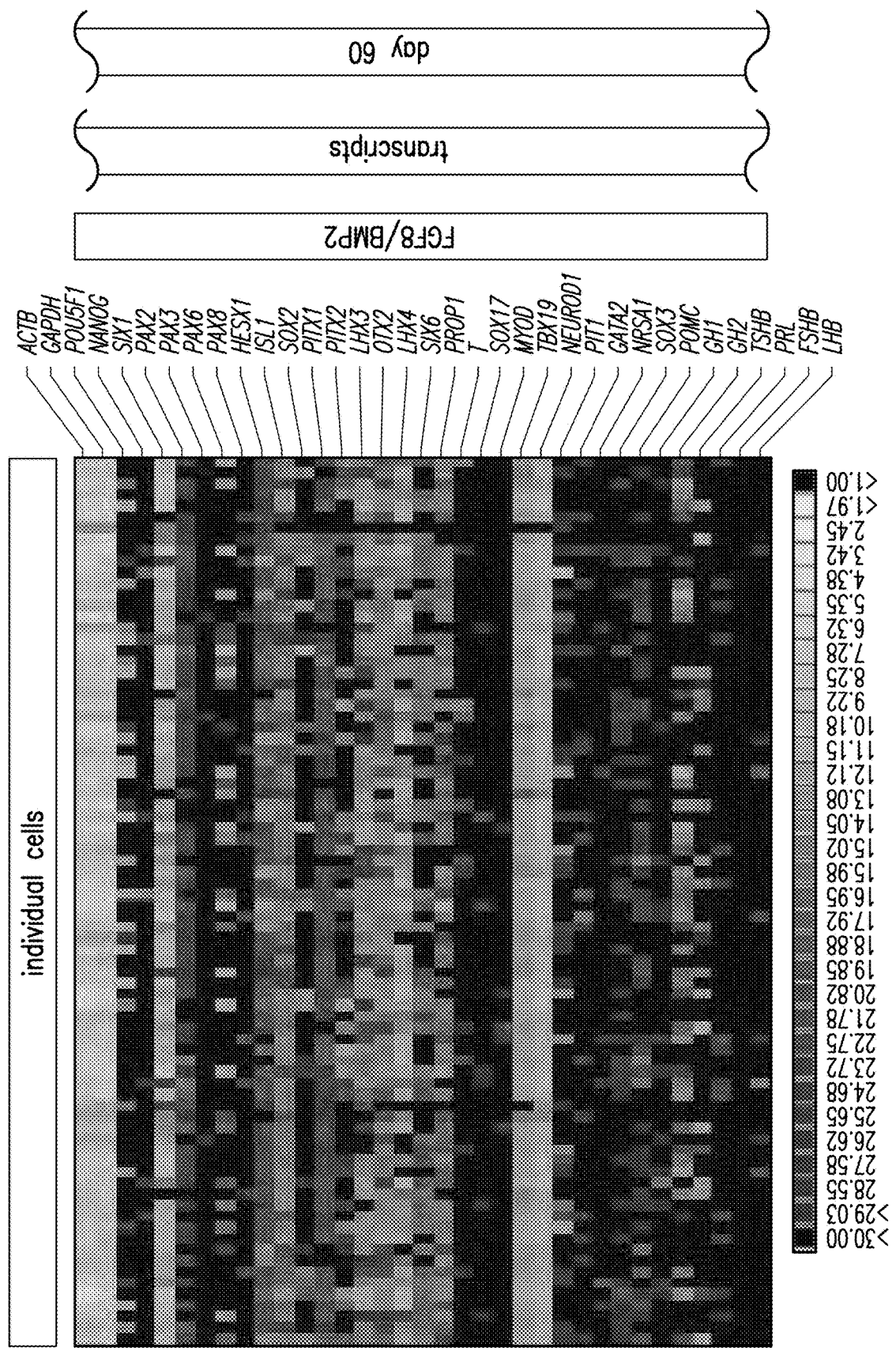
Figure 32:
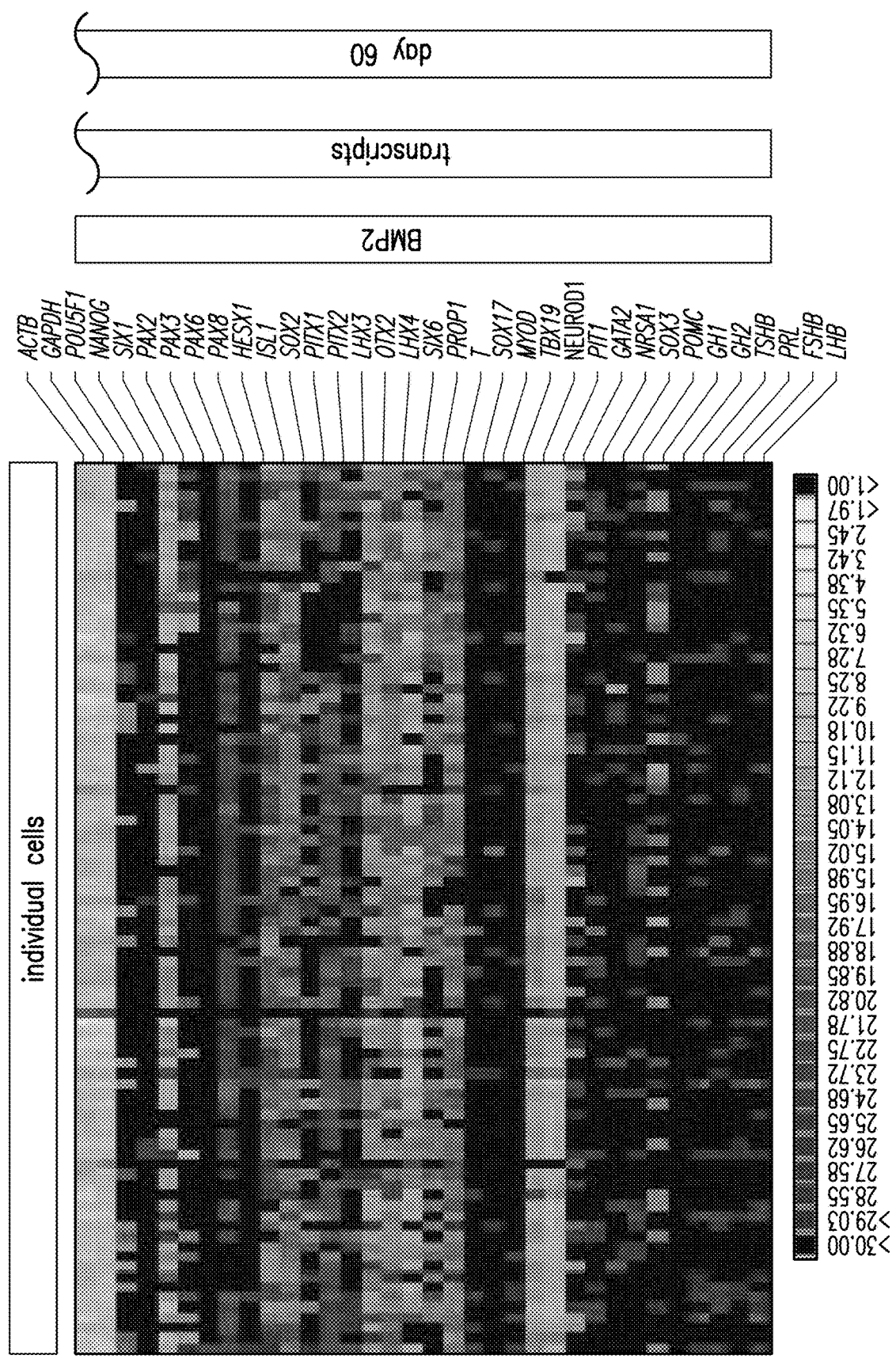
Figure 32:
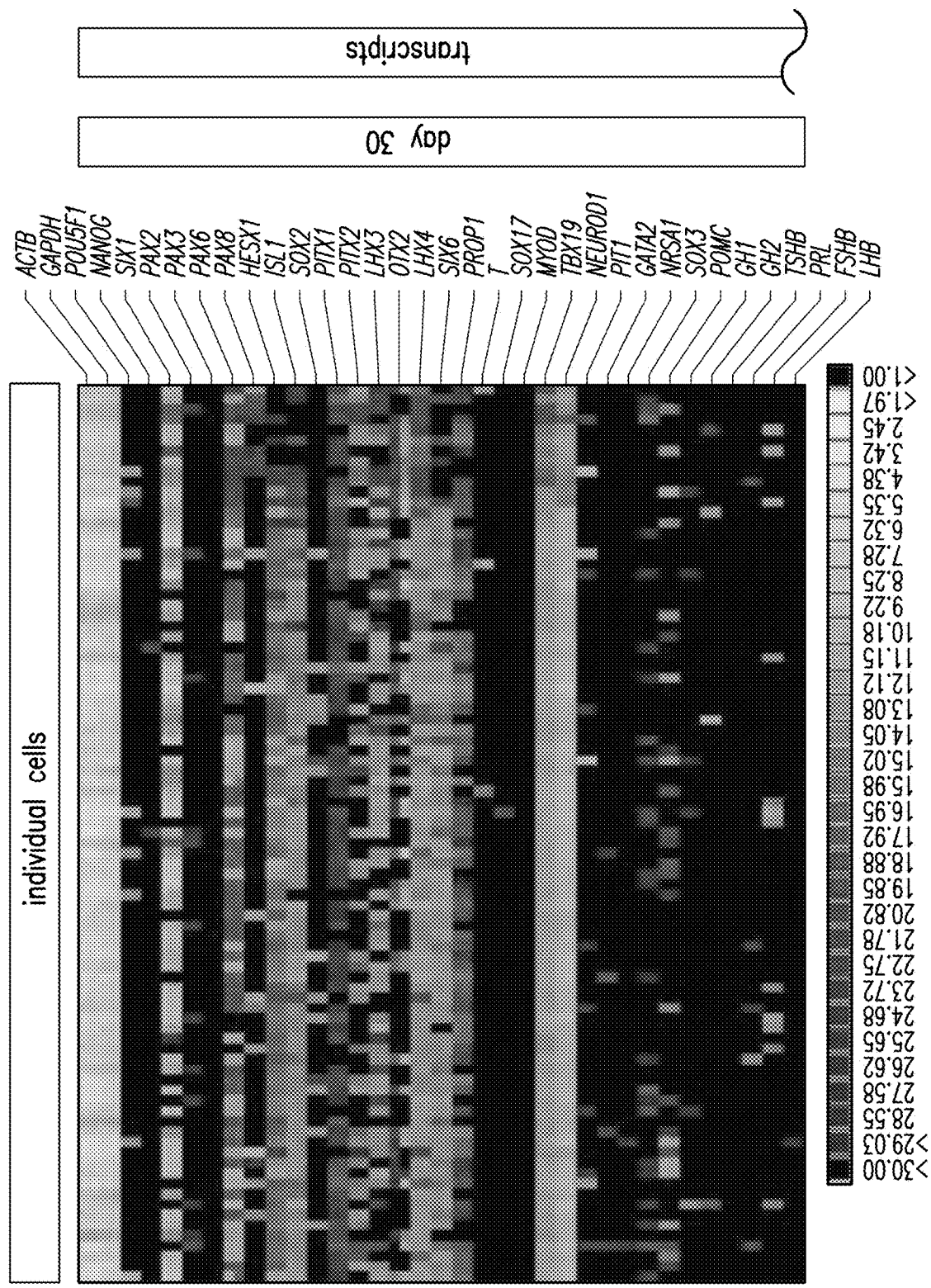
Figure 32:
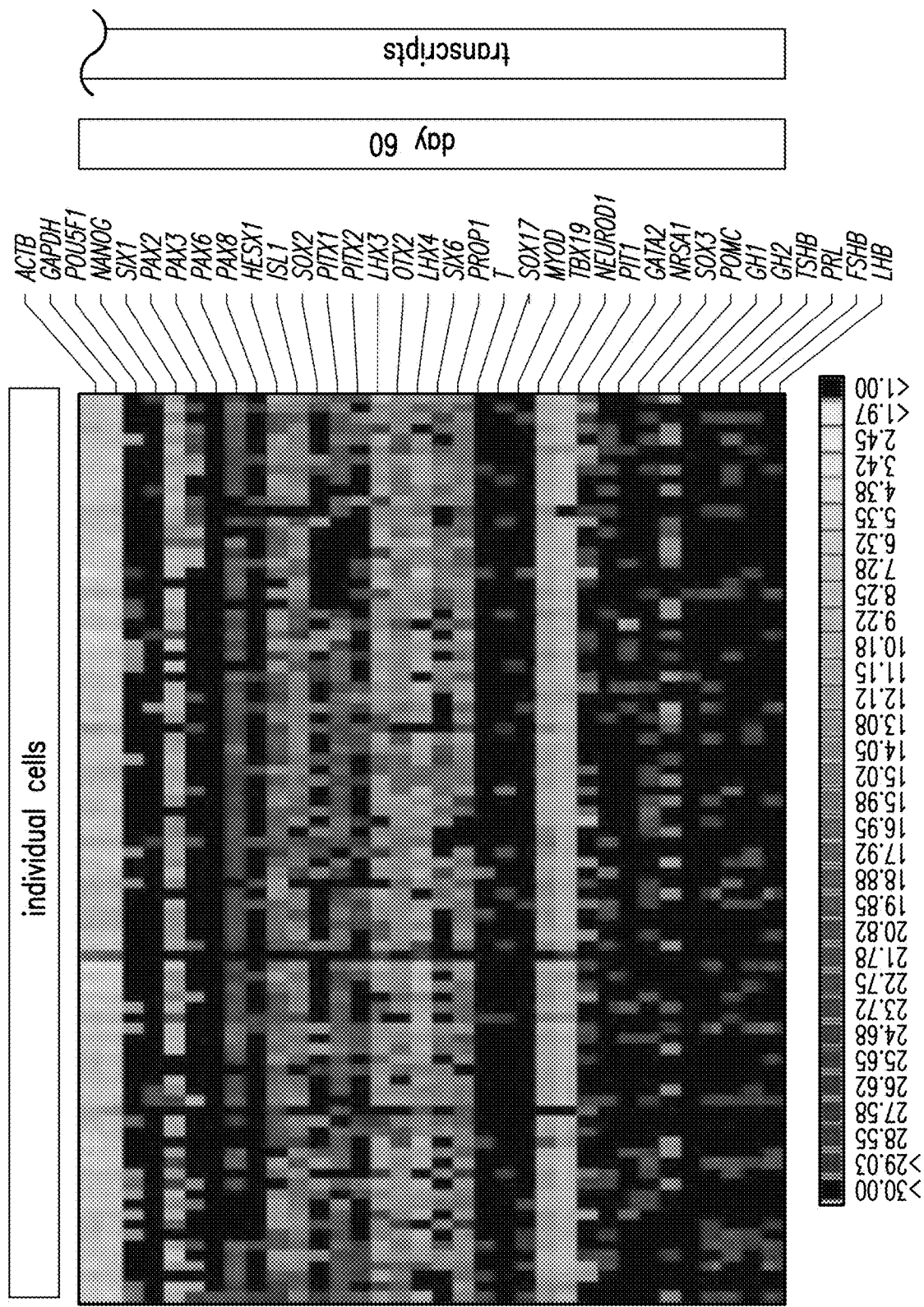

FIG. 32 Shows heatmaps of raw ct values for each cell and gene obtained by single cell q-RT PCR. Raw ct values for every cell and gene obtained for every single cell PCR run are displayed as unprocessed heat maps.

Figure 33A:
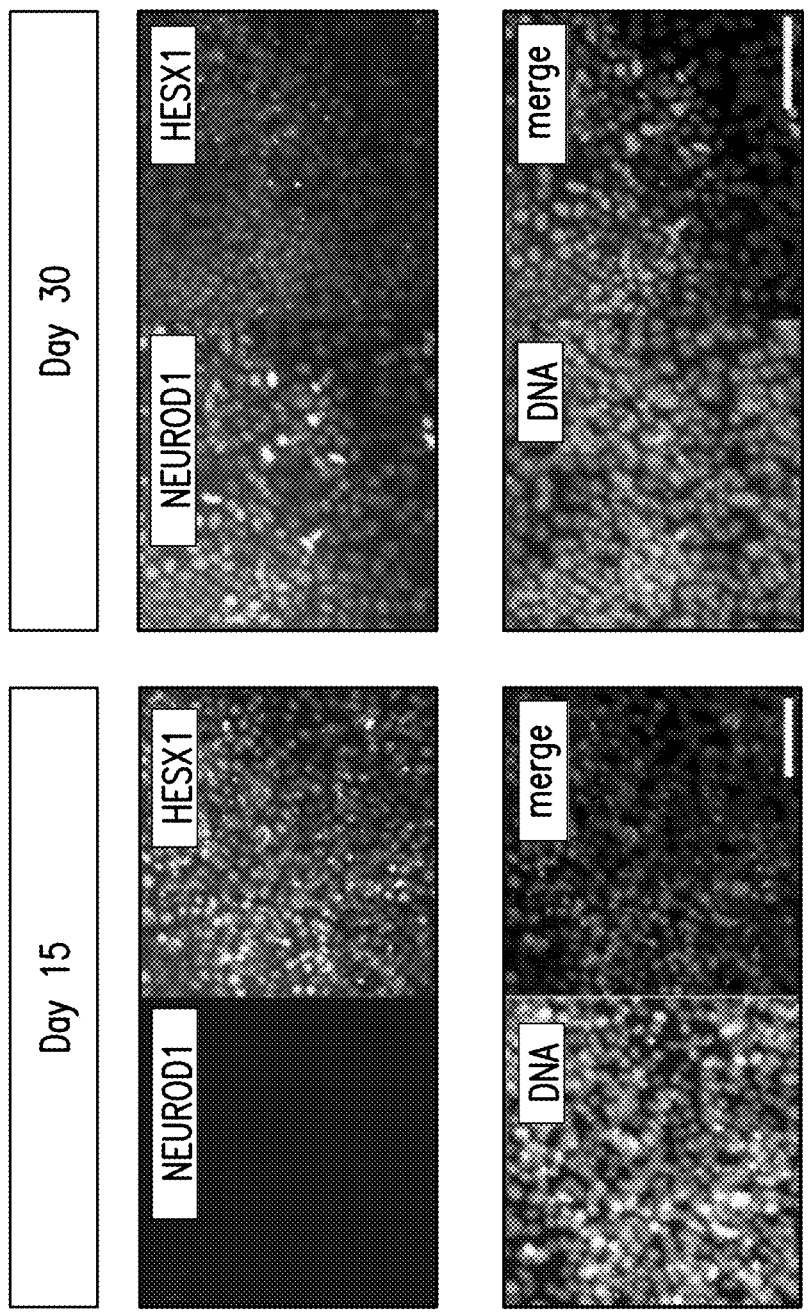

FIG. 33A Shows immunofluorescence validation of single cell q-RT PCR results and quantification of hormonal transcripts in single cells using single cell qRT-PCR. Immunofluorescence analysis of day 15 and day 30 cells differentiated under pituitary conditions. Cells were co-stained for the progenitor marker HESX1 and the transient cortiocotroph marker NEUROD1. Scale bars: 50 μm.

Figure 34A:
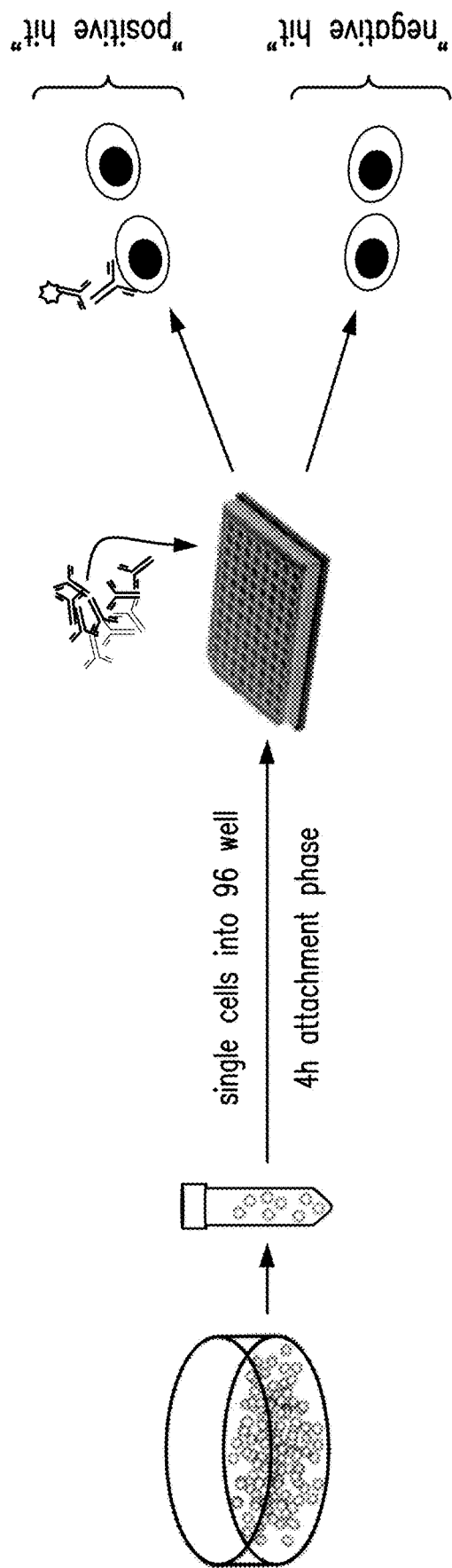
Figure 34B:

FIGS. 34A-34B Shows surface marker screen to identify hormonal subclass specific markers. (A) Schematic representation of experimental procedure. (B) Heatmap of screen results. Percentage indicates cells staining positive for respective marker.

Figure 35:
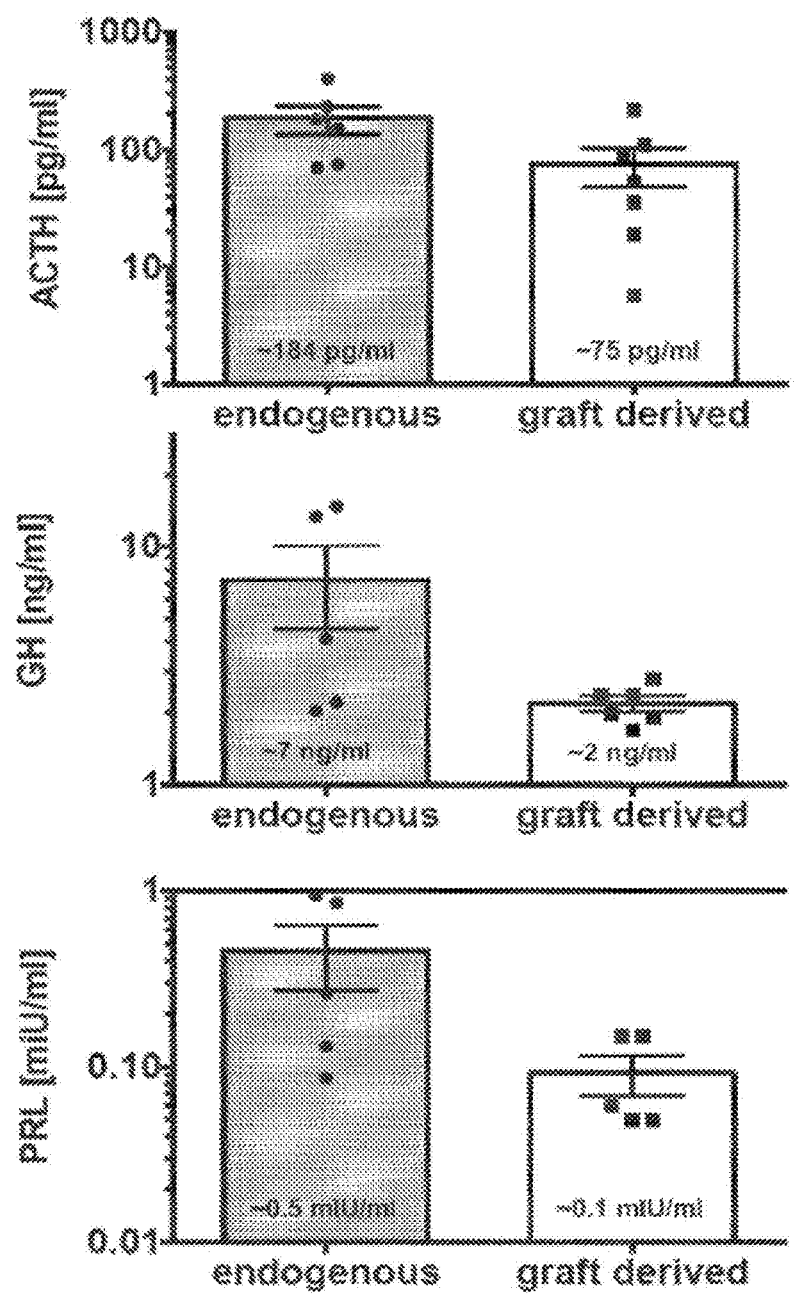

FIG. 35 Shows comparison of endogenous rat hormones in unlesioned animals and graft derived human hormones in lesioned animals. Graft-derived hormone levels shown in FIGS. 21A-21G (week 5) are compared to endogenous hormone levels in unlesioned rats.

5. DETAILED DESCRIPTION OF THE INVENTION

The presently disclosed subject matter relates to in vitro methods for inducing differentiation of human stem cells to cells that express one or more neuroectoderm, neural crest, cranial placode, or non-neural ectoderm lineage marker, and cells produced by such methods, and compositions comprising such cells. Also provided are uses of such cells for treating neurodegenerative disorders.

For purposes of clarity of disclosure and not by way of limitation, the detailed description is divided into the following subsections:

5.1. Definitions;
5.2. Method of Differentiating Stem Cells;
5.3 Compositions Comprising Differentiated Cell Populations;
5.4. Method of Treating Neurodegenerative and Pituitary Disorders;
5.5. Kits;
5.6 Methods of Screening Therapeutic Compounds; and
5.7 Methods of Screening for Compounds that Increase NE, NC, CP or NNE fate.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "signaling" in reference to a "signal transduction protein" refers to a protein that is activated or otherwise affected by ligand binding to a membrane receptor protein or some other stimulus. Examples of signal transduction protein include, but are not limited to, a SMAD, a wingless (Wnt) complex protein, including beta-catenin, NOTCH, transforming growth factor beta (TGFβ), Activin, Nodal, glycogen synthase kinase 3β (GSK3β) proteins, bone morphogenetic proteins (BMP) and fibroblast growth factors (FGF). For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., transforming growth factor-beta (TFGβ), Activin, Nodal, bone morphogenic proteins (BMPs), etc.

"Inhibitor" as used herein, refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of s molecule or pathway. An inhibitor can be any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein). For example, an inhibitor of SMAD signaling can function, for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g., within the extracellular domain). Examples of a SMAD signaling inhibitor molecules and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFβ signaling molecules. Other SMAD inhibitors include dorsomorphin. Antibodies that block activins, nodal, TGFβ, and BMPs are contemplated for use to neutralize extracellular activators of SMAD signaling, and the like. Although the foregoing example relates to SMAD signaling inhibition, similar or analogous mechanisms can be used to inhibit other signaling molecules. Examples of inhibitors include, but are not limited to: LDN193189 (LDN) and SB431542 (SB) (LSB) for SMAD signaling inhibition, XAV939 (X) for Wnt inhibition, and SU5402 (S) for FGF signaling inhibition.

Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

"Activators," as used herein, refer to compounds that increase, induce, stimulate, activate, facilitate, or enhance activation the signaling function of the molecule or pathway, e.g., Wnt signaling, BMP signaling, FGF signaling, etc.

As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells, at least about 5,000 cells or at least about 10,000 cells or at least about 100,000 cells or at least about 1,000,000 cells. The population may be a pure population comprising one cell type, such as a population of NE, CP, NC or NNE precursors, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells. A human stem cell refers to a stem cell that is from a human.

As used herein, the term "embryonic stem cell" and "ESC" refer to a primitive (undifferentiated) cell that is derived from preimplantation-stage embryo, capable of dividing without differentiating for a prolonged period in culture, and are known to develop into cells and tissues of the three primary germ layers. A human embryonic stem cell refers to an embryonic stem cell that is from a human. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell, similar to an embryonic stem cell, formed by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples, CI 4, C72, and the like.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self renewal (in the laboratory) and differentiation. Such cells vary in their differentiation capacity, but it is usually limited to cell types in the organ of origin.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as neural, neural crest, cranial placode, and non-neural ectoderm precursors.

As used herein, the term "directed differentiation" in reference to a stem cell refers to the use of small molecules, growth factor proteins, and other growth conditions to promote the transition of a stem cell from the pluripotent state into a more mature or specialized cell fate.

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., human stem cell) to divide into progeny cells with characteristics that are different from the stem cell, such as genotype (e.g., change in gene expression as determined by genetic analysis such as a microarray) and/or phenotype (e.g., change in expression of a protein, such as SOX1, PAX6, SOX10, SIX1, PITX3, and TFAP2A).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" cells with a compound (e.g., one or more inhibitor, activator, and/or inducer) refers to exposing cells to a compound, for example, placing the compound in a location that will allow it to touch the cell. The contacting may be accomplished using any suitable methods. For example, contacting can be accomplished by adding the compound to a tube of cells. Contacting may also be accomplished by adding the compound to a culture medium comprising the cells. Each of the compounds (e.g., the inhibitors and activators disclosed herein) can be added to a culture medium comprising the cells as a solution (e.g., a concentrated solution). Alternatively or additionally, the compounds (e.g., the inhibitors and activators disclosed herein) as well as the cells can be present in a formulated cell culture medium.

An effective amount is an amount that produces a desired effect.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, culture in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

5.2 Method of Differentiating Stem Cells

The presently disclosed subject matter provides for in vitro methods for inducing differentiation of stem cells (e.g., human stem cells). Non-limiting examples of human stem cells include human embryonic stem cells (hESC), human pluripotent stem cell (hPSC), human induced pluripotent stem cells (hiPSC), human parthenogenetic stem cells, primordial germ cell-like pluripotent stem cells, epiblast stem cells, F-class pluripotent stem cells, somatic stem cells, cancer stem cells, or any other cell capable of lineage specific differentiation. In certain embodiments, the human stem cell is a human embryonic stem cell (hESC). In certain embodiments, the human stem cell is a human induced pluripotent stem cell (hiPSC).

The presently disclosed subject matter is based at least in part on the discovery that the non-CNS ectodermal lineages of the neural crest (NC), cranial placode (CP) and non-neural ectoderm (NNE) can be differentiated from human stem cells by inhibition of SMAD signaling along with activation of BMP signaling, wherein BMP signaling is activated for at least 2 days after initial contact of the cells to effective amounts of one or more SMAD inhibitor and BMP activator, and wherein the cells are further contacted with effective amounts of one or more NC, CP or NNE lineage specific activators and inhibitors. For example, the stem cells can be differentiated to NC by further contacting the cells with effective amounts of one or more Wnt activator; CP can be differentiated from the stem cells by further contacting the stem cells with effective amounts of one or more activator of FGF; and NNE can be differentiated from the stem cells by further contacting the stem cells with effective amounts of one or more inhibitor of FGF.

In certain embodiments, a presently disclosed differentiation method comprises contacting a population of human stem cells with effective amounts of one or more inhibitor of transforming growth factor beta (TGFβ)/Activin-Nodal signaling, which results in inhibition of Small Mothers Against Decapentaplegic (SMAD) signaling. In certain embodiments, the inhibitor of TGFβ/Activin-Nodal signaling neutralizes the ligands including TGFβs, bone morphogenetic proteins (BMPs), Nodal, and activins, or blocking their signal pathways through blocking the receptors and downstream effectors.

Non-limiting examples of inhibitors of TGFβ/Activin-Nodal signaling are disclosed in WO/2010/096496, WO/2011/149762, WO/2013/067362, WO/2014/176606, WO/2015/077648, Chambers et al., Nature Biotechnology 27, 275-280 (2009), and Chambers et al., Nature biotechnology 30, 715-720 (2012), which are incorporated by reference in their entireties herein for all purposes. In certain embodiments, the one or more inhibitor of TGFβ/Activin-Nodal signaling is a small molecule selected from the group consisting of SB431542, derivatives thereof, and mixtures thereof. "SB431542" refers to a molecule with a number CAS 301836-41-9, a molecular formula of $C_{22}H_8N_4O_3$, and a name of 4-[4-(1,3-benzodioxol-5-yl)-5-(2-pyridinyl)-1H-imidazol-2-yl]-benzamide, for example, see structure below:

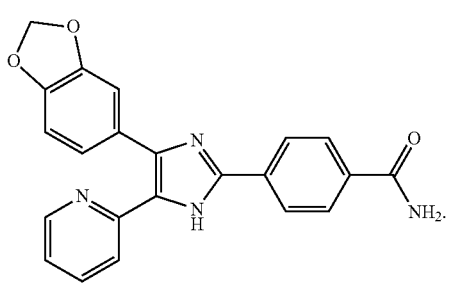 [SMILES: NC(=O)c1ccc(-c2nc(-c3ccc4c(c3)OCO4)c(-c3ccccn3)[nH]2)cc1]

5.2.1 Method of Differentiating Neural Crest (NC) Precursors

In certain embodiments, the presently disclosed subject matter provides for in vitro methods for inducing differentiation of human stem cells into non-CNS precursors, wherein the non-CNS precursors are neural crest (NC) precursors. In certain embodiments, the method comprises contacting a population of human stem cells with effective amounts of one or more inhibitor of TGFβ/Activin-Nodal signaling, effective amounts of one or more activator of BMP signaling (for example, at a concentration of about 1 ng/mL), and effective amounts of one or more activator of wingless (Wnt) signaling.

In certain embodiments, the BMP activator is contacted to the cells for at least 2 days, at least 3 days, at least 4 days, or at least 5 days, or for up to about 2 days, up to about 3 days, up to about 4 days, up to about 5 days or more. In a specific embodiment, the BMP active agent is contacted to the cells for at least about 2 days.

In certain embodiments, the activator of Wnt signaling and inhibitor of TGFβ/Activin-Nodal signaling are contacted to the cells concurrently. In certain embodiments, the activator of Wnt signaling and inhibitor of TGFβ/Activin-Nodal signaling are contacted to the cells for at least 6 days, at least 7 days, at least 8 days, at least 9 days, at least 10 days, at least 11 days, at least 12 days, or more. In certain embodiments, the activator of Wnt signaling and inhibitor of TGFβ/Activin-Nodal signaling are contacted to the cells for or up to about 6 days, up to about 7 days, up to about 8 days, up to about 9, days, up to about 10 days, up to about 11 days, up to about 12 days, or more. In a specific embodiment, the cells are contacted with the Wnt activator and inhibitor of TGFβ/Activin-Nodal signaling for about 12 days or more.

In certain embodiments, the concentration of Wnt activator is increased after about 2, or about 3, or about 4 days after the cells are initially contacted with the Wnt signaling activator. In certain embodiments, the concentration of the Wnt signaling activator is increased by about 50%, 60%, 70%, 80%, 90%, or 100%. In a specific embodiment the concentration of Wnt is increased by about 50% after 2 days of contacting the cells to the Wnt activator.

In certain embodiments, the cells express detectable levels of SOX10, for example, after about 12 days after initially contacted with the inhibitor of TGFβ/Activin-Nodal signaling. In certain embodiments, the cells are contacted with effective amounts of the foregoing agents for a period of time such that at least 10%, 20%, 30%, 40%, 50% or 60% or more of the cells express detectable levels of SOX10.

In certain embodiments, the cells are contacted with an inhibitor of transforming growth factor beta (TGFβ)/Activin-Nodal signaling at a concentration of between about 1 and 20 nM, between about 2 and 18 nM, between about 4 and 16 nM, between about 6 and 14 nM, or between about 8 and 12 nM. In a specific embodiment, the cells are contacted with an inhibitor of transforming growth factor beta (TGFβ)/Activin-Nodal signaling at a concentration of about 10 nM.

In certain embodiments, said activator of BMP signaling is selected from the group consisting of BMP2, BMP4, BMP6, BMP7, derivatives thereof, and mixtures thereof. In certain embodiments, the activator of BMP signaling is contacted to the cells at a concentration of between about 0.01 and 5 ng/ml, between about 0.1 and 2 ng/mL, or between about 1 and 1.5 ng/mL. In a specific embodiment the activator of BMP signaling is contacted to the cells at a concentration of about 1 ng/mL.

In certain embodiments, the cells are contacted with an activator of Wnt signaling at a concentration of between about 50 nM and 2 μM, between about 100 nM and 1.5 μM, between about 150 nM and 1 μM, between about 200 and 950 nM, between about 250 and 900 nM, between about 300 and 850 nM, between about 350 and 800 nM, between about 400 and 750 nM, between about 450 and 700 nM, between about 500 and 650 nM, or between about 550 and 600 nM. In a specific embodiment, the cells are contacted with an activator of Wnt signaling at a concentration of about 600 nM or about 1.5 μM.

In a specific embodiment, the non-CNS NC precursors are differentiated from the human stem cells by contacting the cells with one or more inhibitor of TGFβ/Activin-Nodal signaling (10 nM) for up to 12 days or more, one or more activator of BMP signaling (1 ng/mL) for up to 2 days, and one or more activator of wingless (Wnt) signaling (600 nM for days 0-2, and 1.5 μM from day 2 onward) for up to 12 days or more, wherein the inhibitor of TGFβ/Activin-Nodal signaling, activator of BMP signaling, and activator of Wnt signaling are concurrently contacted to the cells.

In certain embodiments, the one or more activator of Wnt signaling lowers glycogen synthase kinase 3β (GSK3β) for activation of Wnt signaling. Thus, the activator of Wnt signaling can be a GSK3β inhibitor. A GSK3P inhibitor is capable of activating a WNT signaling pathway, see e.g., Cadigan, et al., J Cell Sci. 2006; 119:395-402; Kikuchi, et al., Cell Signaling. 2007; 19:659-671, which are incorporated by reference herein in their entireties. As used herein, the term "glycogen synthase kinase 3β inhibitor" refers to a compound that inhibits a glycogen synthase kinase 3β enzyme, for example, see, Doble, et al., J Cell Sci. 2003; 116:1175-1186, which is incorporated by reference herein in its entirety.

Non-limiting examples of activators of Wnt signaling or GSK3β inhibitors are disclosed in WO2011/149762, Chambers (2012), and Calder et al., J Neurosci. 2015 Aug. 19; 35(33):11462-81, which are incorporated by reference in their entireties. In certain embodiments, the one or more activator of Wnt signaling is a small molecule selected from the group consisting of CHIR99021, derivatives thereof, and mixtures thereof. "CHIR99021" (also known as "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl) pyrimidin-2-ylamino) ethylamino)nicotinonitrile with the following formula.

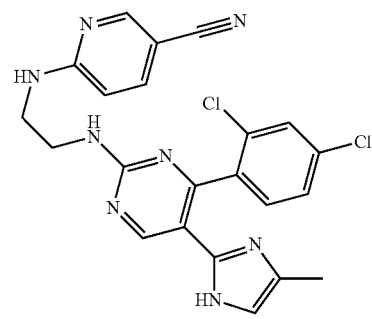 [SMILES: Cc1c[nH]c(-c2cnc(NCCNc3ccc(C#N)cn3)nc2-c2ccc(Cl)cc2Cl)n1]

CHIR99021 is highly selective, showing nearly thousand-fold selectivity against a panel of related and unrelated kinases, with an IC50=6.7 nM against human GSK3β and nanomolar IC50 values against rodent GSK3β homologs.

5.2.2 Method of Differentiating Cranial Placode (CP) Precursors

In certain embodiments, the presently disclosed subject matter provides for in vitro methods for inducing differentiation of human stem cells into non-CNS precursors, wherein the non-CNS precursors are cranial placode (CP) precursors. In certain embodiments, the method comprises contacting a population of human stem cells with effective concentrations of one or more inhibitor of TGFβ/Activin-Nodal signaling, effective concentrations of one or more activator of BMP signaling (for example, at a concentration of about 5 ng/mL), and effective concentrations of one or more activator of fibroblast growth factors (FGF) signaling. In certain embodiments, the BMP activator is contacted to the cells for at least 2 days, at least 3 days, at least 4 days, or at least 5 days, or for up to about 2 days, up to about 3 days, up to about 4 days, up to about 5 days or more. In a specific embodiment, the BMP active agent is contacted to the cells for at least about 2 days.

In certain embodiments, the inhibitor of TGFβ/Activin-Nodal signaling is contacted to the cells for at least 6 days, at least 7 days, at least 8 days, at least 9 days, at least 10 days, at least 11 days, at least 12 days, or more. In certain embodiments, the inhibitor of TGFβ/Activin-Nodal signaling is contacted to the cells for or up to about 6 days, up to about 7 days, up to about 8 days, up to about 9, days, up to about 10 days, up to about 11 days, up to about 12 days, or more. In a specific embodiment, the cells are contacted with the inhibitor of TGFβ/Activin-Nodal signaling for about 12 days or more.

In certain embodiments, the activator of FGF signaling is contacted to the cells at least 1, 2, 3, 4 or 5 days after the cells are contacted the inhibitor of TGFβ/Activin-Nodal signaling.

In certain embodiments, the activator of FGF signaling is contacted to the cells for at least 6 days, at least 7 days, at least 8 days, at least 9 days, at least 10 days, at least 11 days, at least 12 days, or more. In certain embodiments, the activator of FGF signaling is contacted to the cells for up to about 6 days, up to about 7 days, up to about 8 days, up to about 9, days, up to about 10 days, up to about 11 days, up to about 12 days, or more.

In a specific embodiment, the cells are contacted to the activator of FGF signaling about 2 days after the cells are contacted to the inhibitor of TGFβ/Activin-Nodal signaling, wherein the cells are contacted to the FGF activator for about 10 days or more.

In certain embodiment, the cells express detectable levels of SIX1 and/or ELAVL4, for example, after about 12 days after initially contacted with the inhibitor of TGFβ/Activin-Nodal signaling. In certain embodiments, the cells express detectable levels of PAX6, PITX3, Crystallin alpha A, and/or Crystallin alpha B, wherein the cells are lens placode precursors. In certain embodiments, said activators of FGF signaling are selected from the group consisting of FGF2, derivatives thereof, and mixtures thereof.

In certain embodiments, the cells are further contacted with an activator of Wnt signaling for at least 2 days, at least 3 days, at least 4 days, or at least 5 days or more. In certain embodiments, the activator of Wnt signaling is contacted to the cells for up to about 2 days, up to about 3 days, up to about 4 days, up to about 5 days, or more. In certain embodiments, then cells are contacted with the activator of Wnt signaling at least 1, 2, 3, 4 or 5 days after the cells are contacted the inhibitor of TGFβ/Activin-Nodal signaling. In a specific embodiment, the cells are contacted with the activator of Wnt signaling about 2 days after the cells are contacted with the inhibitor of TGFβ/Activin-Nodal signaling, wherein the cells are contacted with the Wnt activator for about 2 days. In certain embodiments, the cells are not contacted with an activator of FGF signaling. In certain embodiments the CP precursor cells express detectable levels of PAX3 and are trigeminal placode precursors.

In certain embodiments, the cells are contacted with effective amounts of the foregoing agents for a period of time such that at least 10%, 20%, 30%, 40%, 50% or 60% or more of the cells express detectable levels of the foregoing markers.

In certain embodiments, the cells are contacted with an inhibitor of transforming growth factor beta (TGFβ)/Activin-Nodal signaling at a concentration of between about 1 and 20 nM, between about 2 and 18 nM, between about 4 and 16 nM, between about 6 and 14 nM, or between about 8 and 12 nM, or abut 10 nM. In a specific embodiment, the cells are contacted with an inhibitor of transforming growth factor beta (TGFβ)/Activin-Nodal signaling at a concentration of about 10 nM.

In certain embodiments, said activator of BMP signaling is selected from the group consisting of BMP2, BMP4, BMP6, BMP7, derivatives thereof, and mixtures thereof. In certain embodiments, the activator of BMP signaling is contacted to the cells at a concentration of between about 0.01 and 10 ng/ml, between about 0.1 and 8 ng/mL, between about 1 and 6 ng/mL, or between about 2 and 5 ng/mL. In a specific embodiment the activator of BMP signaling is contacted to the cells at a concentration of about 5 ng/mL.

In certain embodiments, said activator of FGF signaling is selected from the group consisting of FGF2, FGF4, FGF7, FGF8 and FGF10, derivatives thereof, and mixtures thereof. In certain embodiments, the cells are contacted with the activator of FGF signaling at a concentration of between about 10 and 200 nM, between about 20 and 150 nM, between about 30 and 100 nm, or between about 40 and 75 nM. In a specific embodiment the activator of FGF signaling is contacted to the cells at a concentration of about 100 ng/mL.

In certain embodiments, the cells are contacted with the activator of Wnt signaling at a concentration of between 50 nM and 2 between about 100 nM and 1.5 between about 150 nM and 1 between about 200 and 950 nM, between about 250 and 900 nM, between about 300 and 850 nM, between about 350 and 800 nM, between about 400 and 750 nM, between about 450 and 700 nM, between about 500 and 650 nM, or between about 550 and 600 nM. In a specific embodiment, the cells are contacted with an activator of Wnt signaling at a concentration of between about 600 nM and 1.5 μM.

In a specific embodiment, the non-CNS CP precursors are differentiated from the human stem cells by contacting the cells with one or more inhibitor of TGFβ/Activin-Nodal signaling (10 nM) for up to 12 days or more, one or more activator of BMP signaling (5 ng/mL) for up to 2 days, one or more activator of FGF signaling (100 ng/mL) for up to 10 days or more, wherein the inhibitor of TGFβ/Activin-Nodal signaling and activator of BMP signaling are concurrently contacted to the cells, and wherein the FGF activator is contacted to the cells 2 days after initial contact of the cells to the inhibitor of TGFβ/Activin-Nodal signaling and activator of BMP signaling.

When a Wnt activator is further contacted to the cells to differentiate trigeminal placode precursors, the Wnt activator is contacted to the cells for up to 2 days or more, wherein the Wnt activator is contacted to the cells 2 days after initial contact of the cells to the inhibitor of TGFβ/Activin-Nodal signaling and activator of BMP signaling. In certain embodiments, cells that are contacted to the activator of Wnt signaling are not contacted to an activator of FGF signaling during or after contact of the cells with the activator of Wnt signaling.

5.2.2.1 Method of Differentiating Pituitary Cell Precursors

In certain embodiments, the presently disclosed subject matter provides for in vitro methods for inducing differentiation of human stem cells into non-CNS precursors, wherein the non-CNS precursors are pituitary placode precursors or pituitary cells.

In certain embodiments, the stem cells are differentiated into pituitary cells, or pituitary placode precursors, wherein the human stem cells are contacted with effective amounts of one or more inhibitor of TGFβ/Activin-Nodal signaling, effective amounts of one or more activator of BMP signaling, effective amounts of one or more activator of Sonic Hedgehog (SHH) signaling, and effective amounts of one, two or more activators of FGF signaling. In certain embodiments, the activators of FGF signaling activate FGF8 and FGF10 signaling. In certain embodiments, the inhibitor of TGFβ/Activin-Nodal signaling is contacted to the cells for at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days or more. In certain embodiments, the inhibitor of TGFβ/Activin-Nodal signaling are contacted to the cells for or up to about 6 days, up to about 7 days, up to about 8 days, up to about 9, days, up to about 10 days, up to about 11 days, up to about 12 days, up to about 13 days, up to about 14 days, up to about 15 days, up to about 16 days, up to about 17 days, up to about 18 days, up to about 19 days, up to about 20 days or more. In a specific embodiment, the cells are contacted with the inhibitor of TGFβ/Activin-Nodal signaling for about 15 days or more.

In certain embodiments, the BMP activator is contacted to the cells for at least 2 days, at least 3 days, at least 4 days, or at least 5 days, or for up to about 2 days, up to about 3 days, up to about 4 days, up to about 5 days or more. In a specific embodiment, the BMP active agent is contacted to the cells for at least about 3 days.

In certain embodiments, the one or more activator of SHH signaling and two or more activators of FGF signaling are contacted to the cells for at least 20, 21, 22, 23, 24, 25, 26, 27, 28, 29, 30, 31, 32, 33, 34, 35, 36, 37, 38, 39, 40 days or more; or for up to 20, 21, 22, 23, 24, 25, 26, 27, 28, 29, 30, 31, 32, 33, 34, 35, 36, 37, 38, 39, 40 days or more. In a specific embodiment, the one or more activator of SHH signaling and two or more activators of FGF signaling are contacted to the cells for at least 26 days or more.

In certain embodiments, the one or more activator of SHH and two or more activators of FGF are contacted to the cells at least 2, 3, 4, 5, or 6 days after the cells are contacted to the one or more inhibitor of TGFβ/Activin-Nodal signaling. In a specific embodiment, one or more activator of SHH and two or more activators of FGF are contacted to the cells at least 4 days after the cells are contacted to the one or more inhibitor of TGFβ/Activin-Nodal signaling.

In certain embodiments, the cells are contacted with an inhibitor of transforming growth factor beta (TGFβ)/Activin-Nodal signaling at a concentration of between about 1 and 20 nM, between about 2 and 18 nM, between about 4 and 16 nM, between about 6 and 14 nM, or between about 8 and 12 nM. In a specific embodiment, the cells are contacted with an inhibitor of transforming growth factor beta (TGFβ)/Activin-Nodal signaling at a concentration of about 10 nM.

In certain embodiments, said activator of BMP signaling is selected from the group consisting of BMP2, BMP4, BMP6, BMP7, derivatives thereof, and mixtures thereof. In certain embodiments, the activator of BMP signaling is contacted to the cells at a concentration of between about 0.01 and 10 ng/ml, between about 0.1 and 8 ng/mL, between about 1 and 6 ng/mL, or between about 2 and 5 ng/mL. In a specific embodiment the activator of BMP signaling is contacted to the cells at a concentration of about 5 ng/mL.

In certain embodiments, the cells are contacted with the two or more activators of FGF signaling, each at a concentration of between about 10 and 200 ng/mL, between about 20 and 150 ng/mL, between about 30 and 100 ng/mL, or between about 40 and 75 ng/mL, In a specific embodiment, the cells are contacted with the one or more activator of FGF signaling at a concentration of about 50 ng/mL, or about 100 ng/mL.

In certain embodiments, the cells are contacted with the one or more activator of SHH signaling at a concentration of between about 10 and 400 ng/mL, between about 50 and 350 ng/mL, between about 100 and 300 ng/mL, or between about 150 and 250 ng/mL. In a specific embodiment, the cells are contacted with the one or more activator of SHH signaling at a concentration of about 200 ng/mL.

In certain embodiments, the activator of SHH signaling is selected from the group consisting of Sonic hedgehog (SHH), C25II and smoothened (SMO) receptor small molecule agonists such as purmorphamine, SAG (for example, as disclosed in Stanton et al, Mol Biosyst. 2010 January; 6(1):44-54), derivatives thereof, and mixtures thereof.

In certain embodiments, the cells express detectable levels of PITX1, PITX2, LUX, LHX4, HESX1, SIX6, TBX19, and/or PAX6, for example, at least 9, 15, 30 or 60 days after the cells are contacted with the inhibitor of TGFβ/Activin-Nodal signaling. In certain embodiments, greater than 10%, 20%, 30%, 40%, 50%, 60%, 70%, 80%, or 90% of the population of cells expresses detectable levels of said markers.

In certain embodiments, the cells express detectable levels of one or more hormone, for example, adrenocorticotropic hormone (ACTH), growth hormone (GH), prolactin (PRL), follicle-stimulating hormone (FSH), and/or luteinizing hormone (LH), for example, about 30 to 60 days after the cells are contacted with the inhibitor of TGFβ/Activin-Nodal signaling. In certain embodiments, the cells express ACTH upon contact with CRF or stressin; the cells express GH upon contact with somatocrinin; and/or the cells express FSH upon contact with nafarelin. In certain embodiments, greater than 30%, 40%, 50%, 60%, 70%, 80%, or 90% of the population of cells expresses detectable levels of said hormones. In certain embodiments, at least 5%, 10%, 15%, 20%, 25%, 30%, 35%, 40%, 45% or 50% of the cells express more than one hormone.

In certain embodiments, the cells are further contacted with a dorsalizing agent, a ventralizing agent, or a combination thereof. In certain embodiments, the dorsalizing agent comprises an activator of FGF, for example FGF8. In certain embodiments, the ventralizing agent comprises an activator of BMP, for example, BMP2. In certain embodiments, the cells are contacted with the dorsalizing agent, ventralizing agent, or combination thereof, at least 20, 25, 30, 35, 40 or more days after the cells are contacted with the inhibitor of TGFβ/Activin-Nodal signaling. In certain embodiments, the cells are contacted with the dorsalizing agent, ventralizing agent, or combination thereof, for at least 15, 20, 25, 30, 35, 40, 45 or more days, or for up to 15, 20, 25, 30, 35, 40, 45 or more days. In a specific embodiment, the cells are contacted with the dorsalizing agent, ventralizing agent, or combination thereof for at least 30 days.

In certain embodiments, the cells are contacted with the dorsalizing agent at a concentration of between about 10 and 200 ng/mL, between about 20 and 150 ng/mL, between about 30 and 100 ng/mL, or between about 40 and 75 ng/mL. In a specific embodiment, the cells are contacted with the dorsalizing agent at a concentration of about 50 ng/mL, or about 100 ng/mL.

In certain embodiments, the cells are contacted with the ventralizing agent at a concentration of between about 1 and 30 ng/mL, between about 5 and 25 ng/mL, or between about 10 and 20 ng/mL. In a specific embodiment, the cells are contacted with the ventralizing agent at a concentration of about 10 ng/mL, or about 20 ng/mL.

In certain embodiments, the cells contacted with the dorsalizing agent express detectable levels of pro-opiomelanocortin (POMC).

In certain embodiments, the cells contacted with the ventralizing agent express detectable levels of FSH and/or LH.

In certain embodiments, the cells contacted with a mixture of the dorsalizing and ventralizing agents express detectable levels of GH and/or TSHB.

In a specific embodiment, the stem cells are differentiated into pituitary cells, or pituitary placode precursors, wherein the human stem cells are contacted with one or more inhibitor of TGFβ/Activin-Nodal signaling (10 nM), one or more activator of BMP signaling (5 ng/mL) for about 3 days, one or more activator of Sonic Hedgehog (SHH) signaling (200 ng/mL), and two or more activators of FGF signaling (e.g., 100 ng/mL FGF8 and 50 ng/mL FGF10). In certain embodiments, the activators of SHH and FGF signaling are contacted to the cells about 4 days after the cells are contacted to the one or more inhibitor of TGFβ/Activin-Nodal signaling, wherein the cells are contacted to the SHH and FGF signal activators for at least about 26 days.

5.2.3 Method of Differentiation of Non-Neural Ectoderm (NNE) Precursors

In certain embodiments, the presently disclosed subject matter provides for in vitro methods for inducing differentiation of human stem cells into non-CNS precursors, wherein the non-CNS precursors are non-neural ectoderm (NNE) precursors. In certain embodiments, the method comprises contacting a population of human stem cells with effective amounts of one or more inhibitor of TGFβ/Activin-Nodal signaling, effective amounts of one or more activator of BMP signaling (for example, at a concentration of about 20 ng/mL), and effective amounts of one or more inhibitor if FGF signaling.

Non-limiting examples of inhibitors of FGF signaling include SU5402 (Sun et al., Journal of medicinal chemistry 42, 5120-5130 (1999); Paterson et al. Br. J. Haematol. 124 595 (2004); Tanaka et al., Nature 435:172 (2005)), PD 173074 (N-[2-[[4-(Diethylamino)butyl]amino]-6-(3,5-dimethoxyphenyl)pyrido[2,3-d]pyrimidin-7-yl]-N'-(1,1-dimethylethyl)urea; Bansal et al., J. Neurosci. Res., 2003; 74:486), FIIN 1 hydrochloride (N-(3-((3-(2,6-dichloro-3,5-dimethoxyphenyl)-7-(4-(diethylamino)butylamino)-2-oxo-3,4-dihydropyrimido[4,5-d]pyrimidin-1(2H)-yl)methyl)phenyl)acrylamide; Zhou, Chem. Biol., 2010; 17:285), SU6668 (5-[1,2-Dihydro-2-oxo-3H-indol-3-ylidene)methyl]-2,4-dimethyl-1H-pyrrole-3-propanoic acid; Yamamoto et al., Cancer Res. 2008 Dec. 1; 68(23):9754-62), PD 166285 dihydrochloride (6-(2,6-Dichlorophenyl)-2-[[4-[2-(diethylamino)ethoxy]phenyl]amino]-8-methylpyrido[2,3-d]pyrimidin-7(8H)-one dihydrochloride; Panek et al., J Pharmacol Exp Ther. 1997 December; 283(3):1433-44), PD 161570 (N-[6-(2,6-Dichlorophenyl)-2-[[4-(diethylamino)butyl] amino]pyrido[2,3-d]pyrimidin-7-yl]-N'-(1,1-dimethylethyl)urea; Hamby et al., J Med Chem. 1997 Jul. 18; 40(15):2296-303), AP 24534 (3-(2-Imidazo[1,2-b] pyridazin-3-ylethynyl)-4-methyl-N-[4-[(4-methyl-1-piperazinyl)methyl]-3-(trifluoromethyl)phenyl]-benzamide; Huang et al., J. Med. Chem., 2010; 53:4701), or derivatives thereof.

In certain embodiments, the term "SU5402" refers to a small molecule with a chemical formula of $C_{17}H_{16}N_2O_3$ and chemical name:
2-[(1,2-Dihydro-2-oxo-3H-indol-3-ylidene)methyl]-4-methyl-1H-pyrrole-3-pr-opanoic acid. In certain embodiments, SU5402 has the following structure:

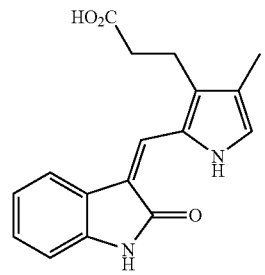 [SMILES: Cc1c[nH]c(/C=C2\C(=O)Nc3ccccc32)c1CCC(=O)O]

In certain embodiments, the inhibitor of TGFβ/Activin-Nodal signaling, activator of BMP signaling, and inhibitor if FGF signaling are contacted to the cells for at least 6 days, at least 7 days, at least 8 days, at least 9 days, at least 10 days, at least 11 days, at least 12 days, or more. In certain embodiments, the inhibitor of TGFβ/Activin-Nodal signaling, activator of BMP signaling, and inhibitor if FGF signaling are contacted to the cells for or up to about 6 days, up to about 7 days, up to about 8 days, up to about 9, days, up to about 10 days, up to about 11 days, up to about 12 days, or more. In a specific embodiment, the cells are contacted with the inhibitor of TGFβ/Activin-Nodal signaling, activator of BMP signaling, and inhibitor if FGF signaling for about 12 days or more.

In certain embodiment, the cells express detectable levels of TFAP2A, and do not express detectable levels of SIX1 and/or SOX10, for example, after about 12 days after initially contacted with the inhibitor of TGFβ/Activin-Nodal signaling.

In certain embodiments, the cells are contacted with effective amounts of the foregoing agents for a period of time such that at least 10%, 20%, 30%, 40%, 50% or 60% or more of the cells express detectable levels of TFAP2A.

In certain embodiments, the inhibitor of FGF signaling comprises SU5402 (Sun et al., Journal of medicinal chemistry 42, 5120-5130 (1999)), derivatives thereof, or mixtures thereof.

In certain embodiments, the cells are contacted with an inhibitor of transforming growth factor beta (TGFβ)/Activin-Nodal signaling at a concentration of between about 1 and 20 nM, between about 2 and 18 nM, between about 4 and 16 nM, between about 6 and 14 nM, or between about 8 and 12 nM. In a specific embodiment, the cells are contacted with an inhibitor of transforming growth factor beta (TGFβ)/Activin-Nodal signaling at a concentration of about 10 nM.

In certain embodiments, said activator of BMP signaling is selected from the group consisting of BMP2, BMP4, BMP6, BMP7, derivatives thereof, and mixtures thereof. In certain embodiments, the activator of BMP signaling is contacted to the cells at a concentration of between about 0.01 and 30 ng/ml, between about 1 and 25 ng/mL, between about 5 and 20 ng/mL, or between about 10 and 15 ng/mL. In a specific embodiment the activator of BMP signaling is contacted to the cells at a concentration of about 20 ng/mL.

In certain embodiments, the cells are contacted with an inhibitor of FGF signaling at a concentration of between about 1 and 20 nM, between about 2 and 18 nM, between about 4 and 16 nM, between about 6 and 14 nM, or between about 8 and 12 nM. In a specific embodiment, the cells are contacted with an inhibitor of FGF signaling at a concentration of about 10 nM.

In a specific embodiment, the non-CNS NNE precursors are differentiated from the human stem cells by contacting the cells with one or more inhibitor of TGFβ/Activin-Nodal signaling (10 nM) for up to 12 days, one or more activator of BMP signaling (20 ng/mL) for up to 12 days, and one or more inhibitor of FGF signaling (10 nM) for up to 12 days, wherein the inhibitor of TGFβ/Activin-Nodal signaling, activator of BMP signaling and inhibitor of FGF signaling are concurrently contacted to the cells.

In certain embodiments, the above-described inhibitors, activators and molecules are added to a cell culture medium comprising the stem cells. Suitable cell culture media include, but are not limited to, Essential 8®/Essential 6® ("E8/E6") medium. E8/E6 medium is commercially available.

E8/E6 medium is a feeder-free and xeno-free medium that supports the growth and expansion of human pluripotent stem cells. E8/E6 medium has been proven to support somatic cell reprogramming. In addition, E8/E6 medium can be used as a base for the formulation of custom media for the culture of PSCs. One example E8/E6 medium is described in Chen et al., Nat Methods. 2011 May; 8(5):424-9, which is incorporated by reference in its entirety. One example E8/E6 medium is disclosed in WO15/077648, which is incorporated by reference in its entirety. In certain embodiments, an E8/E6 cell culture medium comprises DMEM/F12, ascorbic acid, selenum, insulin, NaHCO$_3$, transferrin, FGF2 and TGFβ. In certain embodiments, the E6 media does not include FGF2 and TGFβ. The E8/E6 medium differs from a KSR medium in that E8/E6 medium does not include an active BMP or Wnt ingredient.

The differentiated cells can further express one or more reporter. Non-limiting examples of reporters include fluorescent proteins (such as green fluorescent protein (GFP), blue fluorescent protein (EBFP, EBFP2, Azurite, mKalamal), cyan fluorescent protein (ECFP, Cerulean, CyPet, mTurquoise2), and yellow fluorescent protein derivatives (YFP, Citrine, Venus, YPet, EYFP)), β-galactosidase (LacZ), chloramphenicol acetyltransferase (cat), neomycin phosphotransferase (neo), enzymes (such as oxidases and peroxidases), and antigenic molecules. As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene). In certain embodiments, the reporter can be driven by a recombinant promotor of a NE lineage marker gene, a recombinant promotor of a NC lineage marker gene, a recombinant promotor of a CP lineage marker gene, or a recombinant promotor of a NNE lineage marker gene.

The differentiated cells can be purified after differentiation, e.g., in a cell culture medium. As used herein, the terms "purified," "purify," "purification," "isolated," "isolate," and "isolation" refer to the reduction in the amount of at least one contaminant from a sample. For example, a desired cell type is purified by at least 10%, by at least 30%, by at least 50%, by at least 75%, and by at least 90%, with a corresponding reduction in the amount of undesirable cell types. The term "purify" can refer to the removal of certain cells (e.g., undesirable cells) from a sample.

The presently disclosed subject matter also provides a population of in vitro differentiated cells expressing one or more NC, CP or NNE lineage marker produced by the methods described herein, and compositions comprising such in vitro differentiated cells.

5.3 Compositions Comprising Differentiated Cell Populations

The present disclosure provides for a population of in vitro differentiated cells expressing one or more neural crest lineage marker, or precursor cells thereof, prepared according to the methods described herein. In certain embodiments, at least about 10%, 20%, 30%, or 40% (e.g., at least about 45%, at least about 50%, at least about 55%, at least about 60%, at least about 65%, at least about 70%, at least about 75%, at least about 80%, at least about 85%, at least about 90%, at least about 95%, or at least about 99%, or at least about 99.5%, or at least 99.9%) of the population of cells express one or more neural crest lineage marker, for example, SOX10.

The present disclosure provides for a population of in vitro differentiated cells expressing one or more cranial lens placode lineage marker, or precursor cells thereof, prepared according to the methods described herein. In certain embodiments, at least about 10%, 20%, 30%, or 40% (e.g., at least about 45%, at least about 50%, at least about 55%, at least about 60%, at least about 65%, at least about 70%, at least about 75%, at least about 80%, at least about 85%, at least about 90%, at least about 95%, or at least about 99%, or at least about 99.5%, or at least 99.9%) of the population of cells express one or more cranial lens placode lineage marker, for example, SIX1, PAX6, PITX3, Crystallin alpha A, crystallin alpha B, or combinations thereof.

The present disclosure provides for a population of in vitro differentiated cells expressing one or more cranial trigeminal placode lineage marker, or precursor cells thereof, prepared according to the methods described herein. In certain embodiments, at least about 10%, 20%, 30%, or 40% (e.g., at least about 45%, at least about 50%, at least about 55%, at least about 60%, at least about 65%, at least about 70%, at least about 75%, at least about 80%, at least about 85%, at least about 90%, at least about 95%, or at least about 99%, or at least about 99.5%, or at least 99.9%) of the population of cells express one or more cranial trigeminal placode lineage marker, for example, SIX1, PAX3, or combinations thereof.

The present disclosure provides for a population of in vitro differentiated cells expressing one or more non-neural ectoderm lineage marker, or precursor cells thereof, prepared according to the methods described herein. In certain embodiments, at least about 10%, 20%, 30%, or 40% (e.g., at least about 45%, at least about 50%, at least about 55%, at least about 60%, at least about 65%, at least about 70%, at least about 75%, at least about 80%, at least about 85%, at least about 90%, at least about 95%, or at least about 99%, or at least about 99.5%, or at least 99.9%) of the population of cells express one or more non-neural ectoderm lineage marker, for example, TFAP2A, and less than about 15% (e.g., less than about 10%, less than about 5%, less than about 4%, less than about 3%, less than about 2%, less than about 1%, less than about 0.5%, or less than about 0.1%) of the population of cells express one of more markers selected from the group consisting of SIX1, SOX10 and combinations thereof.

The present disclosure provides for a population of in vitro differentiated cells expressing one or more pituitary cell marker, or pituitary placode precursors, prepared according to the methods described herein. In certain embodiments, at least about 10%, 20%, or 30% (e.g., at least about 35%, at least about 40%, at least about 45%, at least about 45%, at least about 50%, at least about 55%, at least about 60%, at least about 65%, at least about 70%, at least about 75%, at least about 80%, at least about 85%, at least about 90%, at least about 95%, or at least about 99%, or at least about 99.5%, or at least 99.9%) of the population of cells express one or more pituitary cell marker, for example, PITX1, PITX2, LUX, LHX4, HESX1, SIX6, TBX19, PAX6, or combinations thereof.

In certain embodiments, the differentiated cell population is derived from a population of human stem cells. The presently disclosed subject matter further provides for compositions comprising such differentiated cell population.

In certain embodiments, the composition comprises a population of from about $1\times10^4$ to about $1\times10^{10}$, from about $1\times10^4$ to about $1\times10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ of the presently disclosed stem-cell-derived cells.

In certain non-limiting embodiments, the composition further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

In certain embodiments, the composition is a pharmaceutical composition that comprises a pharmaceutically acceptable carrier, excipient, diluent or a combination thereof. The compositions can be used for preventing and/or treating neurodegenerative and pituitary disorders, as described herein.

5.4 Method of Treating Neurodegenerative and Pituitary Disorders

The in vitro differentiated cells that express one or more NC, CP or NNE lineage marker (also referred to as "stem-cell-derived NC, CP or NNE precursors") can be used for treating a neurodegenerative disorder or pituitary disorders. The presently disclosed subject matter provides for methods of treating a neurodegenerative disorder or pituitary disorders comprising administering an effective amount of the presently disclosed stem-cell-derived precursors into a subject suffering from a neurodegenerative disorder or pituitary disorders.

Non-limiting examples of a neurodegenerative disorders include Friedrich's Ataxia.

Non-limiting examples of pituitary disorders include hypopituitary disorders.

The presently disclosed stem-cell-derived precursors can be administered or provided systemically or directly to a subject for treating or preventing a neurodegenerative disorder or pituitary disorder. In certain embodiments, the presently disclosed stem-cell-derived precursors are directly injected into an organ of interest (e.g., the central nervous system (CNS) or peripheral nervous system (PNS)).

The presently disclosed stem-cell-derived precursors can be administered in any physiologically acceptable vehicle. Pharmaceutical compositions comprising the presently disclosed stem-cell-derived precursors and a pharmaceutically acceptable vehicle are also provided. The presently disclosed stem-cell-derived precursors and the pharmaceutical compositions comprising said cells can be administered via localized injection, orthotopic (OT) injection, systemic injection, intravenous injection, or parenteral administration. In certain embodiments, the presently disclosed stem-cell-derived precursors are administered to a subject suffering from a neurodegenerative disorder or pituitary disorder via orthotopic (OT) injection.

The presently disclosed stem-cell-derived precursors and the pharmaceutical compositions comprising said cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed stem-cell-derived precursors, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the presently disclosed stem-cell-derived precursors.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the presently disclosed stem-cell-derived precursors. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the presently disclosed stem-cell-derived precursors is the quantity of cells necessary to achieve an optimal effect. An optimal effect includes, but is not limited to, repopulation of CNS and/or PNS regions of a subject suffering from a neurodegenerative disorder, and/or improved function of the subject's CNS and/or PNS.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the neurodegenerative disorder or pituitary disorder, or otherwise reduce the pathological consequences of the neurodegenerative disorder or pituitary disorder. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

In certain embodiments, an effective amount of the presently disclosed stem-cell-derived precursors is an amount that is sufficient to repopulate CNS and/or PNS regions of a subject suffering from a neurodegenerative disorder or pituitary disorder. In certain embodiments, an effective amount of the presently disclosed stem-cell-derived precursors is an amount that is sufficient to improve the function of the CNS and/or PNS of a subject suffering from a neurodegenerative disorder or pituitary disorder, e.g., the improved function can be about 1%, about 5%, about 10%, about 20%, about 30%, about 40%, about 50%, about 60%, about 70%, about 80%, about 90%, about 95%, about 98%, about 99% or about 100% of the function of a normal person's CNS and/or PNS.

The quantity of cells to be administered will vary for the subject being treated. In certain embodiments, from about $1 \times 10^4$ to about $1 \times 10^{10}$, from about $1 \times 10^4$ to about $1 \times 10^5$, from about $1 \times 10^5$ to about $1 \times 10^9$, from about $1 \times 10^5$ to about $1 \times 10^6$, from about $1 \times 10^5$ to about $1 \times 10^7$, from about $1 \times 10^6$ to about $1 \times 10^7$, from about $1 \times 10^6$ to about $1 \times 10^8$, from about $1 \times 10^7$ to about $1 \times 10^8$, from about $1 \times 10^8$ to about $1 \times 10^9$, from about $1 \times 10^8$ to about $1 \times 10^{10}$, or from about $1 \times 10^9$ to about $1 \times 10^{10}$ of the presently disclosed stem-cell-derived precursors are administered to a subject. In certain embodiments, from about $1 \times 10^5$ to about $1 \times 10^7$ of the presently disclosed stem-cell-derived precursors are administered to a subject suffering from a neurodegenerative disorder or pituitary disorder. In certain embodiments, about $2 \times 10^6$ of the presently disclosed stem-cell-derived precursors are administered to a subject suffering from a neurodegenerative disorder or pituitary disorder. In certain embodiments, from about $1 \times 10^6$ to about $1 \times 10^7$ of the presently disclosed stem-cell-derived precursors are administered to a subject suffering from a neurodegenerative disorder or pituitary disorder. In certain embodiments, from about $1 \times 10^6$ to about $4 \times 10^6$ of the presently disclosed stem-cell-derived precursors are administered to a subject suffering from a neurodegenerative disorder or pituitary disorder. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the cells that are administered to a subject suffering from a neurodegenerative or pituitary disorder for treating a neurodegenerative or pituitary disorder are a population of neurons that are differentiated/maturalized from the presently disclosed stem-cell-derived NC or CP precursors.

5.5 Kits

The presently disclosed subject matter provides for kits for inducing differentiation of stem cells. In certain embodiments, the kit comprises (a) one or more inhibitor of transforming growth factor beta (TGFβ)/Activin-Nodal signaling, (b) one or more activator of BMP signaling (c) one or more activator of Wnt signaling, and (c) instructions for inducing differentiation of the stem cells into a population of differentiated cells that express one or more neural crest lineage marker.

In certain embodiments, the kit comprises (a) one or more inhibitor of transforming growth factor beta (TGFβ)/Activin-Nodal signaling, (b) one or more activator of BMP signaling, (c) one or more activator of FGF signaling, and (d) instructions for inducing differentiation of the stem cells into a population of differentiated cells that express one or more cranial placode lineage marker, In certain embodiments, the kit optionally comprises (e) one or more activator of Wnt signaling.

In certain embodiments, the kit comprises (a) one or more inhibitor of transforming growth factor beta (TGFβ)/Activin-Nodal signaling, (b) one or more activator of BMP signaling, (c) one or more inhibitor of FGF signaling, and (d) instructions for inducing differentiation of the stem cells into a population of differentiated cells that express one or more non-neural ectoderm lineage marker.

In certain embodiments, the kit comprises (a) one or more inhibitor of transforming growth factor beta (TGFβ)/Activin-Nodal signaling, (b) one or more activator of BMP signaling (c) one or more activator of SHH signaling, (d) two or more activators of FGF signaling, and (e) instructions for inducing differentiation of the stem cells into a population of differentiated cells that express one or more pituitary cell or pituitary cell precursor marker.

In certain embodiments, the instructions comprise contacting the stem cells with the inhibitor(s), activator(s) and molecule(s) in a specific sequence. The sequence of contacting the inhibitor(s), activator(s) and molecule(s) can be determined by the cell culture medium used for culturing the stem cells.

In certain embodiments, the instructions comprise contacting the stem cells with the inhibitor(s), activator(s) and molecule(s) as described by the methods of the present disclosure (see, supra, Section 5.2).

In certain embodiments, the present disclosure provides for kits comprising an effective amount of a population of the presently disclosed stem-cell-derived precursors or a composition comprising said precursors in unit dosage form. In certain embodiments, the stem-cell-derived cells are mature differentiated cells. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering a population of the presently disclosed stem-cell-derived precursors or a composition comprising thereof to a subject suffering from a neurodegenerative disorder or pituitary disorder. The instructions can comprise information about the use of the cells or composition for treating or preventing a neurodegenerative disorder. In certain embodiments, the instructions comprise at least one of the following: description of the therapeutic agent; dosage schedule and administration for treating or preventing a neurodegenerative disorder or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

5.6 Methods of Screening Therapeutic Compounds

The presently disclosed stem-cell-derived NC and CP precursors can be used to model neurodegenerative disorders or pituitary disorders, for example Friedrich's Ataxia or hypopituitary disorders, and can also serve as a platform to screen for candidate compounds that can overcome disease cellular phenotypes. The capacity of a candidate compound to alleviate a neurodegenerative disorder or a pituitary disorder can be determined by assaying the candidate compound's ability to rescue a physiological or cellular defect, which causes a neurodegenerative disorder or pituitary disorder.

In certain embodiments, the method comprises: (a) providing (i) a population of the presently disclosed precursors derived from stem cells (e.g., human stem cells) wherein the progenitor cells are prepared from iPSCs from a subject with the neurodegenerative disorder or pituitary disorder, or wherein the progenitor cells express cellular and/or metabolic characteristics of the disorder, and (ii) a test compound; (b) contacting the precursors with the test compound; and (c) measuring functional activity, or gene expression of the precursors. In certain embodiments, the precursors are contacted with the test compound for at least about 24 hours (1 day), about 2 days, about 3 days, about 4 days, about 5 days, about 6 days, about 7 days, about 8 days, about 9 days, or about 10 days. In certain embodiments, the precursors are matured into differentiated neurons prior to contacting with the test compound.

5.7 Methods of Screening for Compounds that Increase NE, NC, CP or NNE Fate

The present disclosure provides for methods of screening (for example, high throughput screening) for compounds that promote NE, NC, CP or NNE progenitor differentiation. In certain embodiments, NE, NC, CP, and NNE can be differentiated according to the methods described herein, wherein the cells are contacted with a test compound to determine if the test compound enhances NE, NC, CP or NNE induction. In certain embodiments, the cells express a reporter construct for determining differentiation of the cells into NE, NC, CP or NNE fates, for example, a detectable reporter such as GFP operably linked to a promoter of a gene specific for NE, CP, NC or NNE progenitors. In certain embodiments, the reporter construct is selected from the group consisting of PAX6::H2B-GFP, SOX10::GFP, SIX1::H2B-GFP, and a combination thereof.

In certain embodiments the screening method comprises culturing human stem cells according to the methods described herein, wherein a test compound is added to the culture media at day 1, or day 2, or day 3, or day 4, or day 5, or day 6, or day 7. In certain embodiments, the screening method comprises determining the level of detectable expression of one or more NE, NC, CP or NNE precursor markers, such as SOX1 and/or PAX6 (NE); SIX1, PAX6, PAX3, PITX3, Crystallin alpha A, crystallin alpha B, and/or TFAP2A (CP); SOX10 and/or TFAP2A (NC); or TFAP2A and lack of expression of detectable SIX1 and SOX10 (NNE), in cells cultured with the test compound, and comparing said levels to the level of expression of the same markers in cells cultured in media without the test compound, wherein an increase in the level of marker expression in the cells cultured with the test compound indicates that the test compound enhances NE, NC, CP or NNE precursor induction.

6. EXAMPLES

The presently disclosed subject matter will be better understood by reference to the following Examples, which are provided as exemplary of the presently disclosed subject matter, and not by way of limitation.

6.1 Example 1: Methods of Preparing Stem Cell-Derived Progenitor Cells of the Neuroectoderm (NE), Neural Crest (NC) Cranial Placode (CP) and Non-Neuro Ectoderm (NNE) Ectodermal Lineages Summary Human pluripotent cells (hPSCs) can give rise to potentially any cell type of the body. A long-term goal is the development of strategies to re-create the complete human lineage tree in vitro. Such an effort depends on establishing modular differentiation platforms that provide access to each of the three germ-layers. Here we present a strategy to derive all four main ectodermal lineages (CNS, neural crest, cranial placode, non-neural ectoderm) in parallel under fully defined conditions. Using genetic reporter lines, we demonstrate a dose- and time-dependent role for BMP signaling in driving non-CNS ectodermal derivatives. We apply gene-editing tools to dissect mechanism of early cell fate decisions and further demonstrate the utility of our platform in a chemical screen for compounds that increase cranial placode fate. Reproducible access to the four ectodermal lineages on demand is a first milestone on the road towards recreating the human ectodermal lineage diversity in vitro.

Figure 1A:
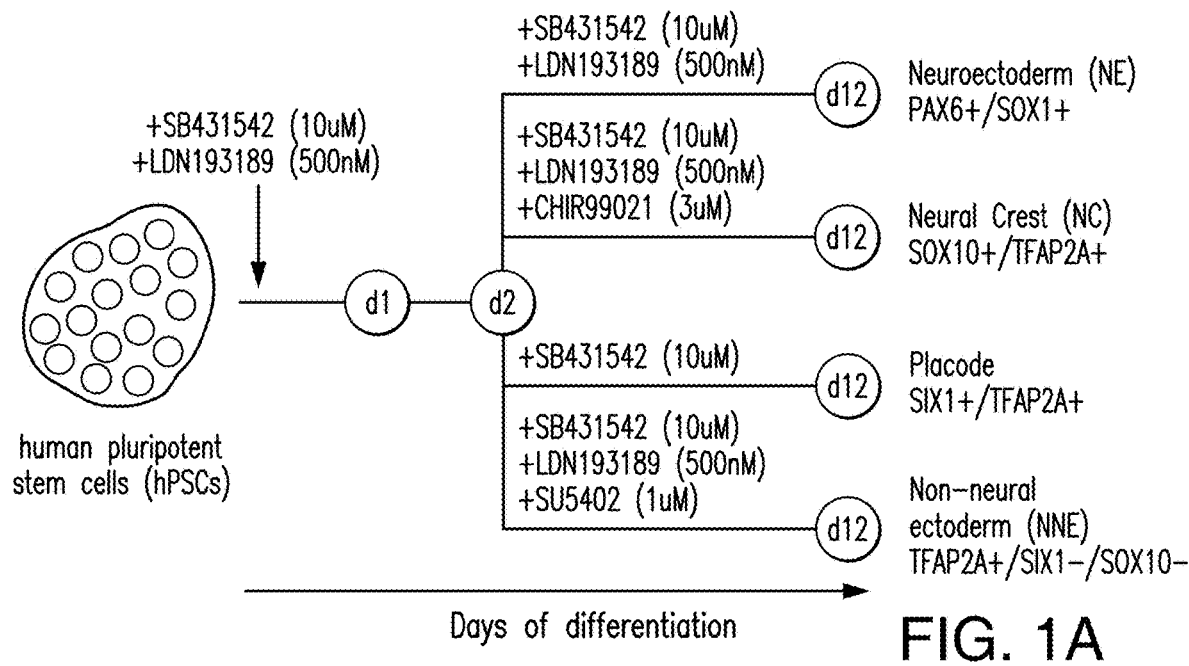
Figure 1B:
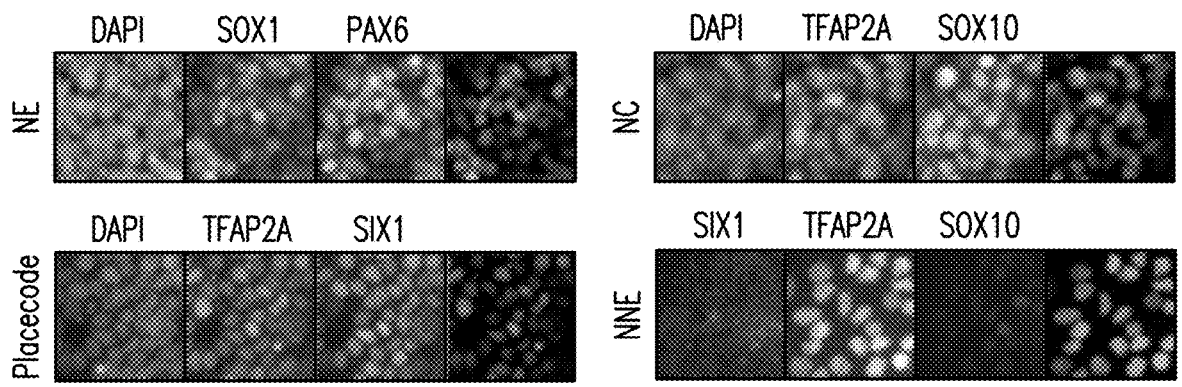

Results dSMADi-Based Differentiation Protocols for Deriving the Four Ectodermal Lineages are Skewed Towards NE Fate Using a Chemically Defined System The four major ectodermal lineages comprise the neuroectoderm (NE), neural crest (NC), cranial Placode (CP) and non-neural ectoderm (NNE). Each of those lineages can be generated by modifying dSMADi conditions using traditional KSR-based protocols as summarized in FIG. 1A. Interestingly, under KSR-conditions, the optimal time point to include or subtract patterning factors is at 48 hours post induction (Dincer et al., 2013; Mica et al., 2013). At this time point, continuation with dSMADi generates anterior NE, activation of Wnt signaling with CHIR99021 generates cranial NC, removal of the BMP inhibitor LDN193189 generates cranial placode, or blocking FGF signaling with SU5402 in combination with LDN193189 removal triggers NNE fates. Defined transcription factors and other lineage-specific markers can be used to uniquely identify each of the early ectodermal lineages. The generation of NE is marked by the expression of the SOX1 and PAX6 and the absence of TFAP2A. The expression of TFAP2A separates the ectoderm from the non-neural ectoderm-derived cell types. In combination with TFAP2A, expression of SOX10 versus SIX1 specifically mark NC versus placode identity, respectively. It remains unclear if there is a specific transcription factor for NNE, however the expression of TFAP2A in the absence of both SOX10 and SIX1 appears to reliably identify NNE under those culture conditions (FIG. 1B).

Figure 1C:
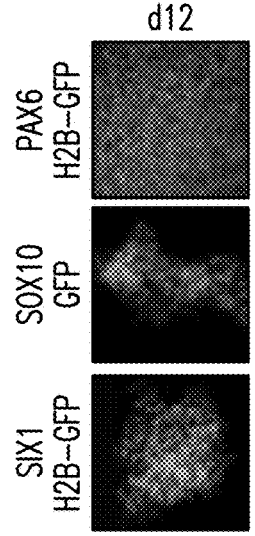
Figure 1D:
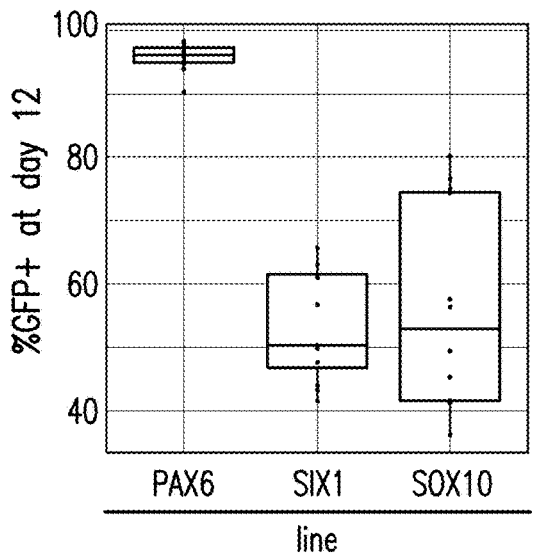
Figure 8A:
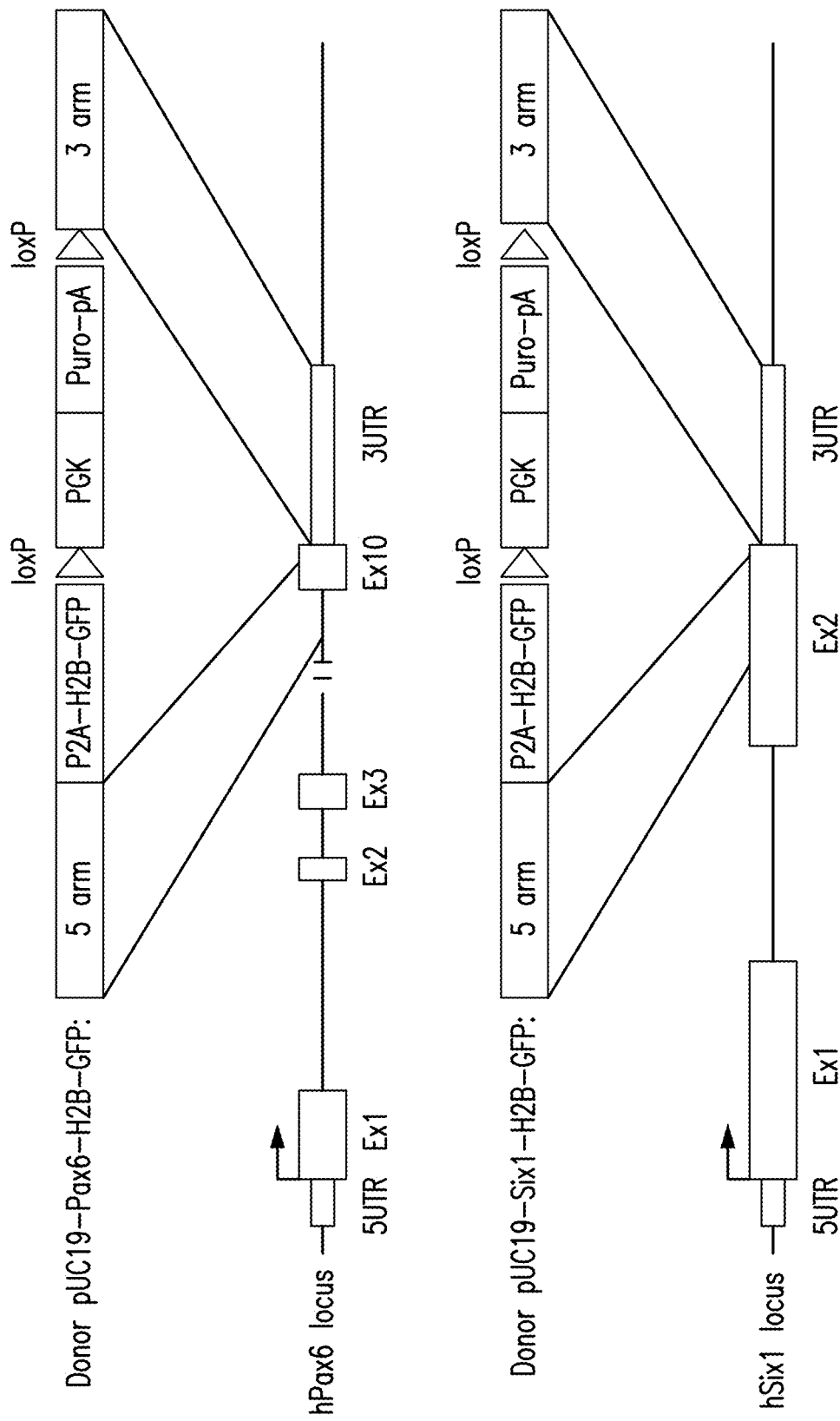

To monitor the acquisition of those various ectodermal lineage markers under defined differentiation media, we used three GFP reporter lines, PAX6::H2B-GFP (FIGS. 8A, B, C and D) SOX10::GFP (Chambers et al., 2012; Mica et al., 2013) and SIX::H2B-GFP (FIGS. 8A, B, E and F). Differentiation of the lines into specific cell types produced an average of 95%, 50% and 58% of NE, Placode and NC, respectively (FIGS. 1C and 1D). Although overall differentiation efficiencies were quite high, the yield of Placode and NC cells was variable across repeat differentiations suggesting that certain factors in the differentiation media may vary and thereby affecting yield.

Figure 1E:
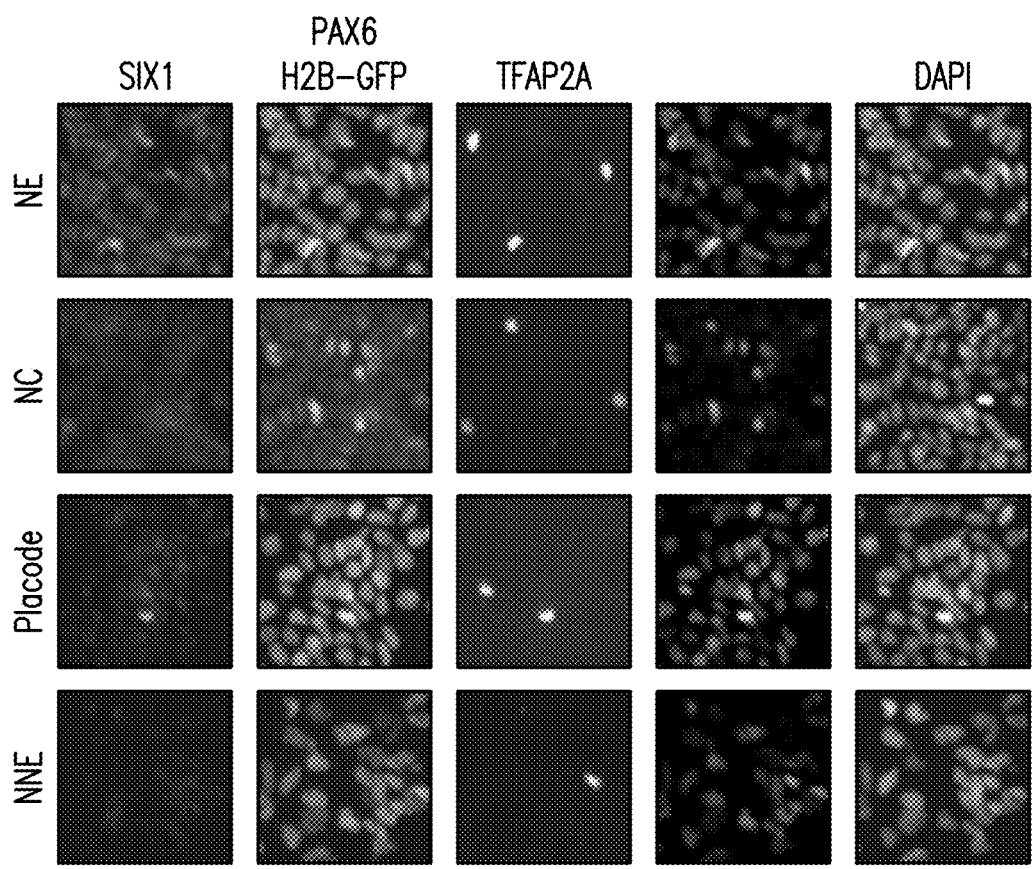
Figure 1F:
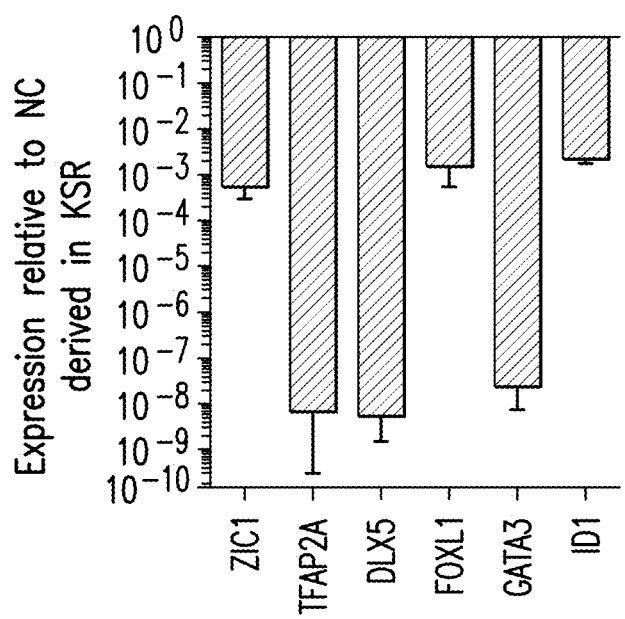

To transition these protocols into the more defined E6 media, we adapted hPSCs in E8 for multiple passages and simply replaced the KSR-based medium with an E6 based differentiation while maintaining factors and concentrations as described previously to trigger the 4 major ectodermal lineages (FIG. 9A). We found that the original concentration for some of the small molecules, namely CHIR99021 and SU5402, effectively killed the cells during differentiation and had to be re-titrated. After determining an optimal non-toxic concentration for each of the small molecules we observed that NE formation under E6 conditions was equivalent to that obtained with KSR-based conditions. The formation of NE in the absence of small molecules under E6 conditions was demonstrated previously (Lippmann et al., 2014). We compared the efficiency of generating PAX6 positive cells using either no small molecules, using dSMADi or using the single TGFβ inhibitor SB431542 (SB). We found robust PAX6 expression in the absence of dSMADi (~40% of total cells on day 12 post induction). However, the percentage of cells expressing PAX6 was further improved upon addition of SB or dSMADi to nearly 90% and 80%, respectively (FIGS. 1E and 9B). PAX6+NE efficiently differentiated further into Tbr1 positive cortical neurons (FIG. 9E) indicating that these cells can progress through the early stages of cortical development. Surprisingly, high percentages of PAX6+ cells were observed in nearly all the treatment groups including in cells maintained under CP or NNE. Although CP cells can express PAX6, these cells did not co-express Six1 suggesting they are not of CP origin (FIG. 1E). Additionally, NC induction did not generate either PAX6 nor SOX10 positive cells, indicating that Wnt activation may alter the regional identity of differentiating cells rather than inducing NC (FIG. 9C, D). Finally, a comparative gene expression analysis of hPSCs differentiated towards NC under KSR versus E6 conditions revealed a lack of non-neural marker expression under E6 (FIG. 1F). Overall, the data suggest that E6 lacked factors to induce non-neural fates under the small molecule conditions developed for KSR based differentiations.

BMP Signaling Through TFAP2A is Necessary to Generate Non-CNS Fates

In order to understand why most ectodermal lineage protocols defaulted to PAX6 positive NE, we investigated the induction of Transcription Factor AP2α (TFAP2A). TFAP2A is highly expressed in NC, CP and NNE and is upregulated within two days of differentiation preceding the expression of other lineage-restricted markers such as SOX10 and SIX1 for NC and CP, respectively (Dincer et al., 2013). Many signaling molecules have been reported to induce the expression of TFAP2A such as retinoids and activators of WNT and BMP signaling (Luo et al., 2003; Xie et al., 1998). Interestingly, under KSR conditions, none of those signaling factors were added during induction of the non-CNS fates despite robust TFAP2A expression (Dincer et al., 2013). Therefore, we postulated that KSR-based media can trigger endogenous signals sufficient for the induction of TFAP2A, while E6 lacked those factors. Accordingly, we attempted to restore TFAP2A expression by directly adding relevant signaling molecules.

Generation of Placode and Non-Neural Ectoderm

BMP signaling has been shown to be important for the formation of NNE and Placode in the developing chick embryo (FIG. 2A) (Groves and LaBonne, 2014). We sought to induce the expression of TFAP2A and suppress PAX6+ NE by extrinsic stimulation of BMP signaling. We observed that TFAP2A expression is rapidly upregulated within three days of treatment in a dose dependent manner (FIGS. 2B and C). At a high concentration (20 ng/ml) cells become TFAP2A positive and lack the expression of SOX10 and SIX1 implying that NNE is triggered by strong BMP signaling activation (FIG. 2D). Additional inhibition of the FGF pathway further blocks CP induction and thereby increases the efficiency of NNE induction. When subjecting NNE to terminal differentiation towards keratinocytes using defined conditions, we were able to attain both immature (K14 positive) and mature epidermal cells (K18 positive) (FIG. 2E).

Figure 2F:
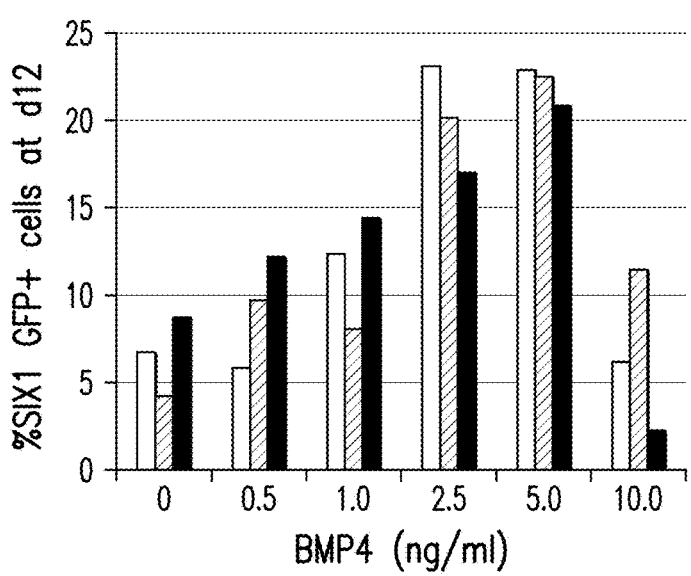
Figure 2G:
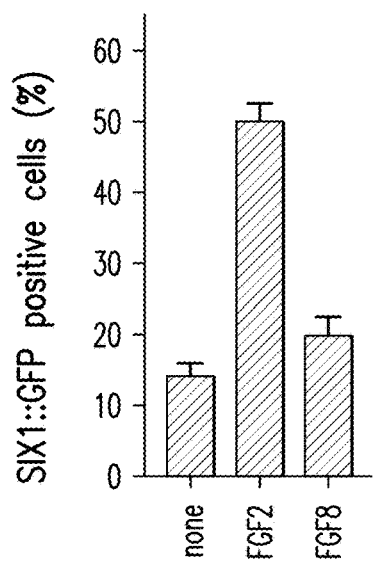

We next asked whether a three-day pulse of BMP signaling was sufficient to generate SIX1 positive placode. Indeed, the addition of BMPs triggered placode induction, but at low efficiencies (FIGS. 2F and 10). Dose-response studies showed that moderate concentrations of BMP4 (around 5 ng/ml) are optimal for CP induction. Intriguingly, the majority of the cells during placode differentiation resembled NNE indicating that the direct addition of FGF agonists may be necessary to boost the efficiency of placode generation at the expense of NNE. Indeed, the addition of FGF2, but not FGF8, during the differentiation enhanced the formation of SIX1 positive cells to nearly 50% (FIG. 2G).

Figure 2H:
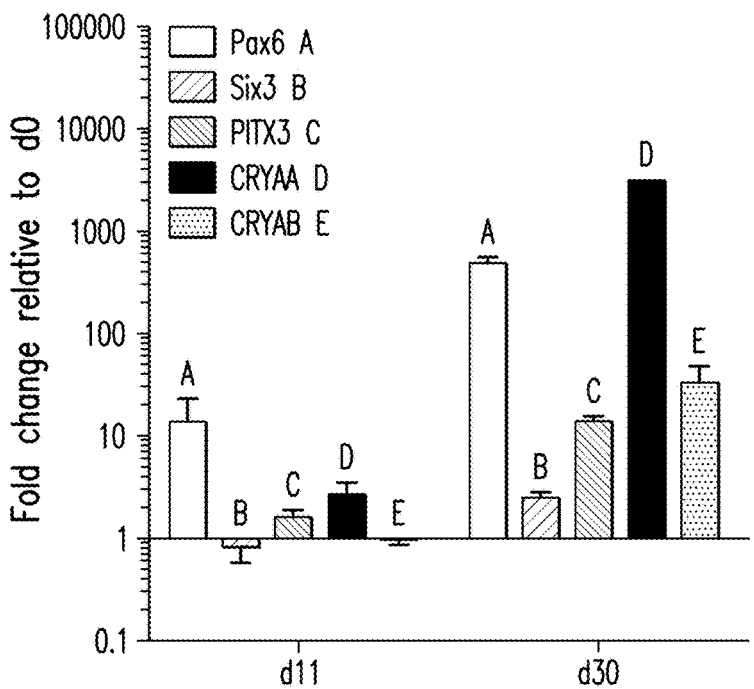
Figure 2I:
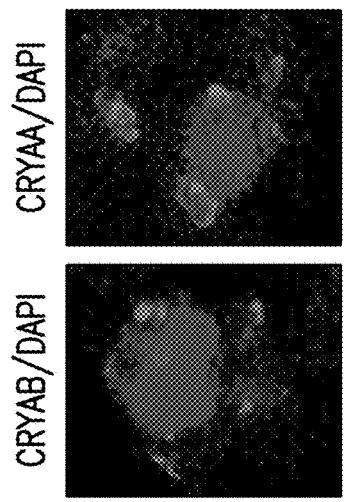

It has previously been shown that the trigeminal placode is the default placode fate derived from hPSCs (Dincer et al., 2013). We terminally differentiated the Six1 positive CP and observed expression of the anterior placode marker PAX6 rather than posterior markers such as PAX3 (FIG. 2H). Expression of PAX6 in placode cells is compatible with lens, pituitary or olfactory identity. Further differentiation of these cells demonstrated expression of lens specific factors such as PITX3, Crystallin Alpha A and B confirming their fate as primarily lens rather than trigeminal placode (FIGS. 2H and I).

Figure 2J:
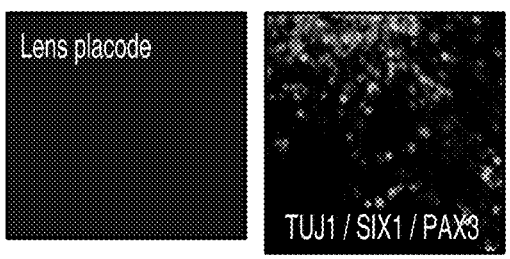

We next sought to identify factors that promote the derivation of trigeminal placodes at the expense of lens placode since these factors are likely in the KSR and not in E6. During development, trigeminal placodes are induced posterior to the PAX6+ lens, pituitary and olfactory placode. Therefore, we tested whether activation of canonical WNT signaling, known to trigger posterior cell identity during development may be sufficient to shift patterning towards the trigeminal lineage. Exposure to an additional pulse of CHIR99021 during the early stages of differentiation, after the placode-inducing BMP pulse, was capable of triggering PAX3 expression in SIX1 placode cells indicative of trigeminal placode (FIG. 2J). These data show that under minimal media conditions, we were able to closely recapitulate in vivo cell fate choices and regional specification during in vitro placode induction.

Generation of Neural Crest

Figure 3A:
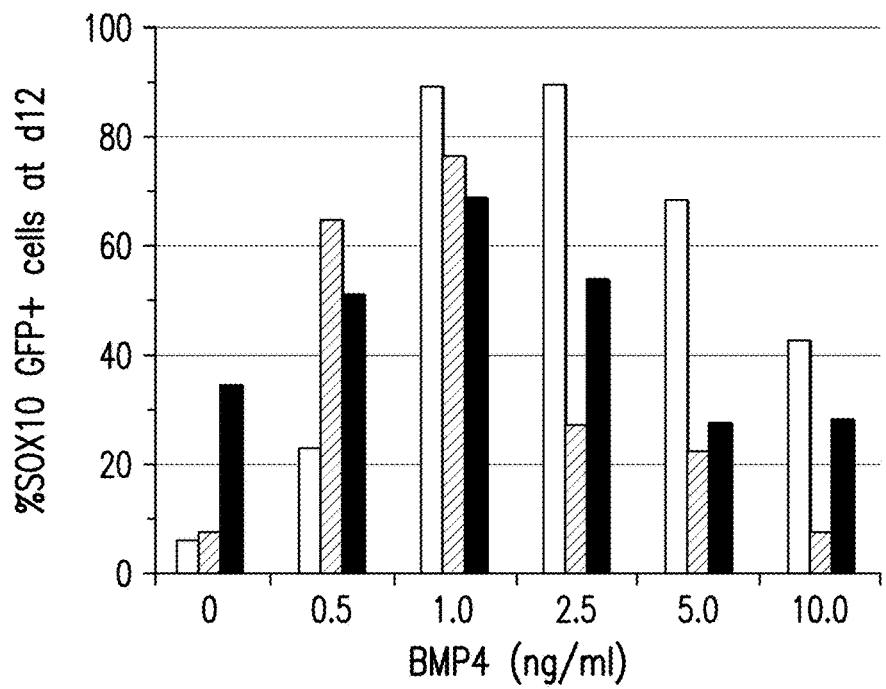
Figure 3B:
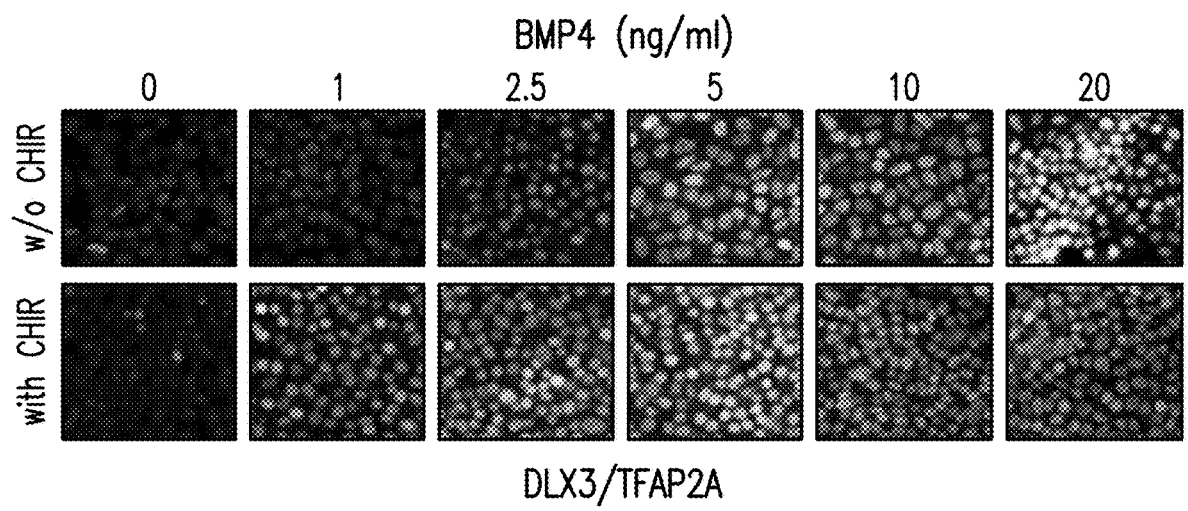
Figure 3C:
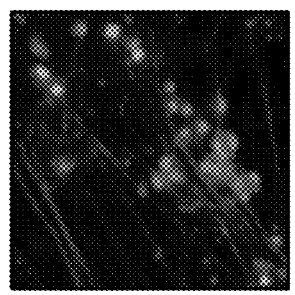

We observed that activation of WNT signaling in combination with a short pulse of BMP4 (1 ng/ml) was capable to generate a nearly homogenous SOX10 positive NC population (FIG. 3A and FIG. 11). Interestingly, at such low concentrations of BMP4, TFAP2A is induced only weakly (FIG. 2F) suggesting that NC may initially arise from early precursor cells expressing no or low levels of TFAP2A. However, the addition of both WNT and BMP act synergistically to activate TFAP2A as well as DLX3, another marker of the non-neural ectodermal fates (FIG. 3B). Furthermore, the differentiation of the NCs can give rise to autonomic and sensory neurons marked by Isl1 and Mash1 staining respectively (FIG. 3C). The data presented here demonstrate that an early, dose-dependent induction of BMP signaling allows for the formation of the non-CNS ectoderm fates including NC with greater efficiencies and lower variability than previously reported.

Expression Analysis of Purified Cell Types from the Ectoderm

Since we generated reporter lines specific for the ectoderm, we wanted to determine the transcriptional expression signatures of all 4 human ectodermal lineages. With the exception to the NNE lineage, we sorted GFP positive cells using the respective reporter lines (all lines were derived from WA-09 hESCs) and performed RNA sequencing in those purified cells. Unbiased clustering algorithms showed that NE clustered closely with hESCs while NNE clustered the furthest apart from all other ectodermal lineages. Interestingly, based on principle component analysis, NC and CP clustered closely to each other suggesting that these cells have similar transcriptional profiles yet are divergent in their expression of SOX10 and SIX1, respectively (FIGS. 4A and B). Differentially expressed genes were then grouped into those with shared and unique expression profiles (FIG. 4C). Such expression patterns were then subjected to gene ontology analysis (Edgar et al., 2013) (FIG. 4D). Genes associated with extracellular matrix reorganization were significantly enriched in all non-CNS derived cell types. This implies that the early BMP signal during the differentiation may act in part through ECM or at least induces cell types enriched for ECM related transcripts. Conversely, ontologies associated with NE involve synaptic transmission and nervous system development. Individual ontologies specific for NC include cell adhesion and calcium binding while CP was enriched for synaptic transmission and ion membrane transport. Taken together, the transcriptional expression profiles for the four ectodermal lineages are globally distinct and capture functions associated with each of the specific lineages represented.

Given the paucity of early human ectodermal lineage data, we next asked whether we could identify more specific markers for each of the ectodermal lineages. Transcripts with significant differential expression among ectodermal lineages as well as uniquely upregulated genes were subjected to further validation. Genes specifically upregulated during ectoderm differentiation that are shared between the CNS and non-CNS fates include ANXA1, LGI1, NR2F2 and ZNF503. Additionally, factors that delineate the CNS versus non-CNS are NEUROG1, HAND1, TFAP2A and TFAP2B (FIG. 4E). In the NE, factors such as Sox1 and Hes5 exclusively identify cells of the CNS while low-level Pax6 transcripts could be found in all other lineages (FIG. 4F). Interestingly, we observed high expression of an uncharacterized zinc finger protein ZNF229 specifically in the NC lineage. As for other lineages, we identified ELAVL4 and SMYD1 to be preferentially expressed in placode and NNE, respectively. This analysis provides a subset of both known and novel genes for the identification of each of the major lineages during ectoderm formation.

Loss of TFAP2A Impacts the Derivation of Non-CNS Derivatives

The novel conditions presented here to derive the 4 major ectodermal lineages are robust and efficient. Therefore, we want to perform perturbation studies to identify key players during ectodermal lineage specification. One prime candidate in our study for commitment to non-CNS fates was TFAP2A as it is highly expressed early during dSMADi. To address whether non-CNS lineages are dependent on TFAP2A expression, we generated TFAP2A knockout hESC lines using the CRISPR/Cas9 system. Two guide RNAs were used to induce frame shift deletions and positive clones were sequenced to determine the extent and the nature of the deletion (FIGS. 12A and 12B). Ablation of TFAP2A expression was confirmed using a short 3-day induction in the presence of high BMPs (FIGS. 5A and 12C). Further comparative studies of TFAP2A versus wild-type hESCs showed robust upregulation of E-cadherin at day 6 of differentiation in wild type but not TFAP2A knockout cells under CP or NNE conditions (FIG. 5B). These data suggest that TFAP2A promotes expression of E-cadherin which may protect cells from an EMT-like transition toward NC or CP fates.

Given the E-cadherin data, we postulated that the TFAP2A knockout cells would not be able to transition towards non-CNS lineages and default towards CNS NE. In agreement with this hypothesis, the derivation of the NE was not impacted upon loss of TFAP2A (FIG. 5C). CNS-enriched transcription factors such as Sox1 and Pax6 were abundant with little contamination from the other lineages. Furthermore, NC and placode protocols resulted in increased levels of SOX1 and PAX6 expression (FIGS. 5C and D) in TFAP2A knockout versus wild type cells. Unexpectedly, however, during the derivation of the TFAP2A KO cells towards NC or CP, SOX10 and SIX1 positive cells could be found, albeit at lower numbers compared to wild type, respectively. This indicates that abolishing TFAP2A expression is not sufficient to suppress non-CNS cell types. Another surprising result was that disruption of TFAP2A did not affect the expression of other NNE related genes such as Smyd1. Those data suggest that the formation of NNE does not solely rely on TFAP2A expression. In fact, previous studies have shown that expression of TFAP2C (AP2α) is predominant in NNE (Li and Cornell, 2007).

Our novel platform for deriving the human ectodermal lineages has demonstrated an important role for BMP signaling during ectodermal lineage specification that mimics developmental programs in vivo. Additionally, we present a proof-of-concept that the system can be genetically manipulated to uncover the role of defined developmental factors involved in determining fate choice such as TFAP2A.

Small Molecule Screen for Factors to Enhance Placode Formation

Converting to a chemically defined system yields a modular differentiation platform with excellent yield for most major ectodermal lineages. However, the derivation of the CP fate remained relatively low (~40%). To further enhance the efficiency of CP induction and to demonstrate the suitability of our platform in HTS assays, we performed a small molecule screen using the Library of Pharmacologically Active Compounds (LOPAC) on the Six1::H2B-GFP reporter line (FIG. 6A). We identified three potential candidates that increased expression of Six1 above the levels observed in control differentiations. BRL-5443 a serotonin receptor agonist; Parthenolide, a plant hormone that has the capacity to inhibit NF-kB and STAT mediated confirmation transcription; and Phenantroline, a metalloprotease inhibitor. Upon further validation of the primary hits, Phenantroline was confirmed to reliably enhance the percentage of cells expressing Six1 (FIGS. 6C, 13A, 13B).

Although there was no obvious link between the compound and CP development, we next determined how Phenantroline may act on specifically enriching placode fate. Differentiation towards CP showed a five-fold increase in Six1 expression over controls without inducing the expression of other lineage markers such as Sox10, T, MyoD or Sox17 (FIG. 6D). We next assessed whether addition of Phenantroline improved the efficiency of CP induction in an additive or selective manner. Interestingly, there is a nearly 4-fold increase (69% versus 18%) of Six1 positive cells upon addition of Phenantroline in the absence of FGF2 (FIG. 6E). After the addition of FGF2 or FGF2 plus Phenantroline, the enrichment of Six1 positive cells was decreased to, 34% and 46%, respectively. These results suggest that Phenantroline may selectively enrich for Six1 positive CP cells at the expense of other ectodermal lineages that may not be able to survive in the presence of the compound. In conclusion, the small molecule screen demonstrates the feasibility of using our ectodermal lineage platform to identify novel factors that can further improve the efficiency of hPSC differentiation toward lineages of choice.

Figure 7A:
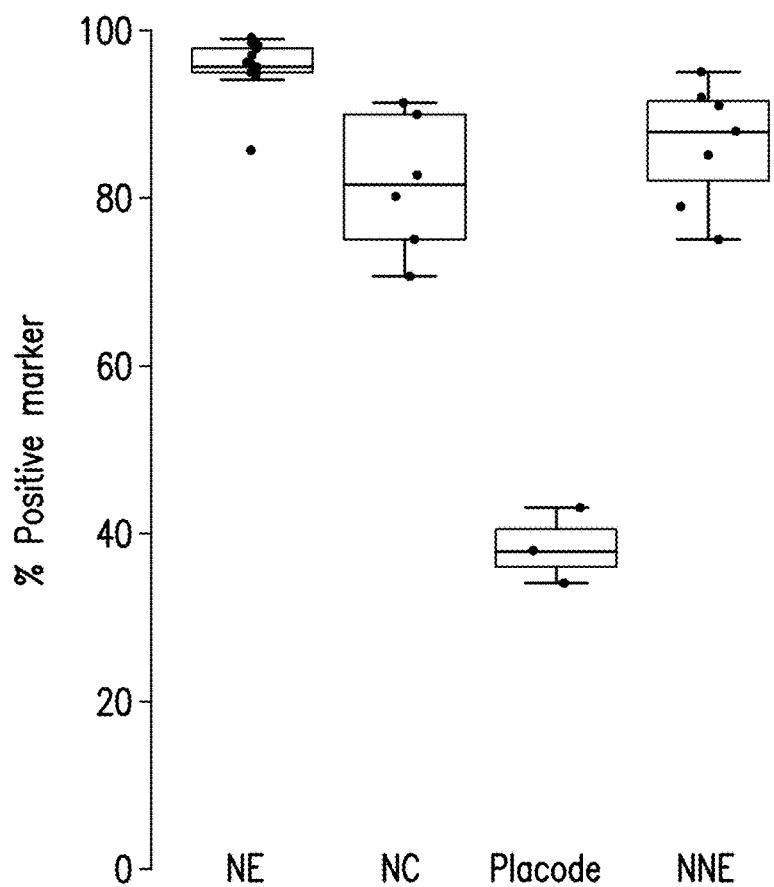
FIGS. 7A-7B Shows the culture protocols for the modular generation of NE, NC, CP and NNE progenitors which comprises dose-dependent BMP exposure in E6 media. (A) The generation of NE was robust in both KSR and E6 systems without modifications. (B) An initial BMP pulse increased differentiation of NC, CP and NNE fates.
Figure 7B:
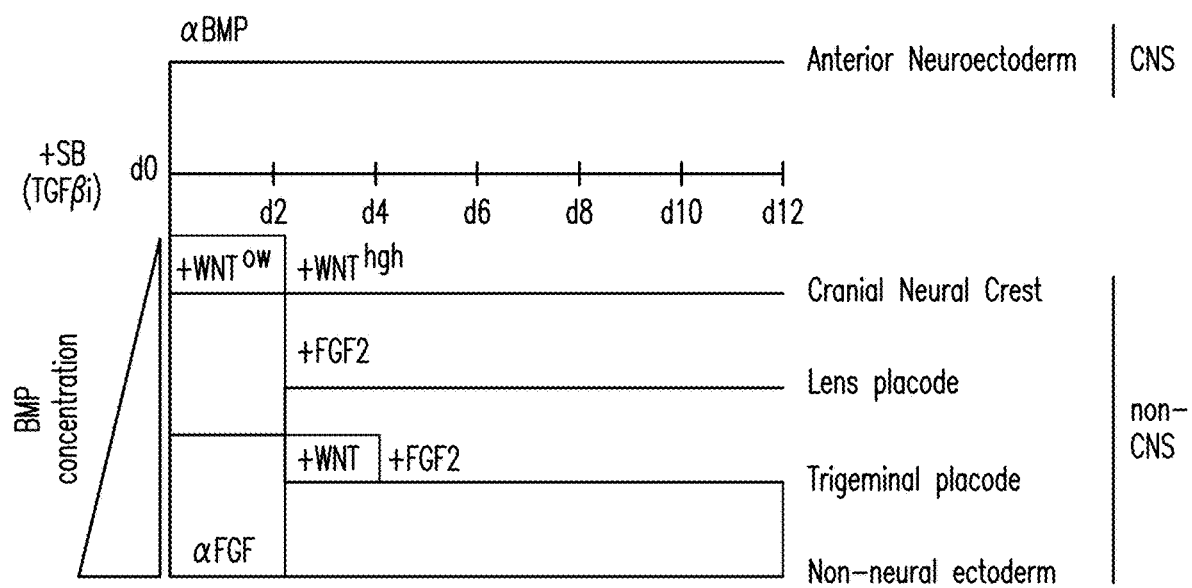

Our modified approach for the modular generation of the NC, CP and NNE relied on a dose-dependent BMP signaling response whereas the generation of NE was robust in both systems without modification (FIG. 7A). The initial pulse of BMP signaling allowed for the increased efficiencies and reduced variability in the generation of NC and to a lesser extent, CP when compared to non-modular KSR-based differentiation conditions (FIG. 7B versus FIG. 1D).

Our main focus was to establish a highly robust and modular ectodermal differentiation platform that eliminates the variability caused by media-related factors such as KSR. However, there are additional potential sources of variability such as coating substrate and cell density. Matrigel is a commonly used coating substrate composed of thousands of proteins whereas Vitronectin, used in our current study, is a single recombinant protein. To determine whether use of Matrigel instead of Vitronectin could negatively affect robustness of ectodermal lineage specification, we tested eleven batches of Matrigel in comparison to our standard Vitronectin-based protocol. Surprisingly, all but two batches yielded highly robust induction efficiencies (FIG. 14A). Another potential factor known to affect ectodermal lineage choice is cell density. Namely, the generation of PAX6 positive NE versus Sox10 positive NC was shown to depend on the starting hPSC plating density (Chambers et al., 2009). We performed differentiations using 50,000 to 300,000 cells/cm$^2$ using both Matrigel (FIG. 14B) and Vitronectin (FIG. 14C) and found that cell density did not play an obvious role in cell fate determination. Those additional data further confirm the robustness our differentiation platform that shows minimal dependence on coating substrate or cell density for acquisition of the four ectodermal lineages.

Discussion

The goal of deriving a multitude of specific cell types on demand from hPSCs is dependent on the availability of a suitable differentiation platform. Currently available protocols are prone to many inconsistencies in media composition and culture techniques. Here, we present a strategy to derive all four major ectodermal lineages using a chemically defined system. The application of in vivo developmental cues greatly enhances the success of differentiation, and we show that the modulation of four signaling pathways is sufficient to recreate the full diversity of early ectodermal lineage choice. The delineation of CNS versus non-CNS fates relies on the dose-dependent treatment with BMPs. The specific BMP concentration to promote any specific lineage such as NC, CP and NNE is very narrow. BMPs act at least in part via upregulating TFAP2A that can work in concert with WNT activation to generate NC, with FGF activation to generate CP and with FGF inhibition to generate NNE. Our results demonstrate that in a minimal media system, one can recapitulate ectodermal cell fate decision by mimicking in vivo development using a handful of small molecules. The ectodermal differentiation platform is highly robust and amenable for genetic dissection of developmental pathways as well as small molecule screening. The present study also demonstrated that the loss of TFAP2A does not affect the formation of NE or NNE, but greatly affects the derivation of NC and CP fates.

Methods hPSC Culture and Differentiation

H9 ESCs (WA09) and modified reporter lines (passage 40-70) were cultured in the Knockout Serum Replacement (KSR) (Life Technologies) based media (DMEM-F12, 20% KSR, L-glutamate and 10 ng/ml FGF2) on mouse embryonic fibroblast feeders. KSR hPSCs were directly transferred to the E8 media (Life Technologies) coated with Vitronectin and adapted for 4-5 passages before differentiations were performed. KSR based differentiations were performed as previously described, neuroectoderm and neural crest (Mica et al., 2013), and placode and non-neural ectoderm (Dincer et al., 2013).

All differentiations starting from E8 were dissociated into single cells using EDTA and replated at high density in E8 with the ROCK inhibitor (Tocris). Cells were typically seeded at a density of 200,000 cells/cm$^2$ on Matrigel coated dishes. Switching from E8 to E6 triggered differentiations (i.e. d0). Neuroectoderm (NE) formation was generated by culturing the cells in E6 with 10 nM SB and 500 nM LDN until d12. Neural Crest (NC) was first treated with 10 nM SB, 600 nM CHIR and 1 ng/ml BMP4 from d0-d2. At d2, cells were maintained in 10 nM SB with 1.5 uM CHIR until d12. Lens placode was first treated with 10 nM SB and 5 ng/ml BMP4 from d0-d2. At d2, cells were maintained in 10 nM SB with 100 ng/ml FGF2 until d12. Trigeminal placode was first treated with 10 nM SB and 5 ng/ml BMP4 from d0-d2. At d2, CHIR was added to the SB and BMP4 until d4. Finally, non-neural ectoderm (NNE) was treated with 10 nM SB, 10 nM SU5402 and 20 ng/ml BMP4 until d12.

Generation of the Pax6 and Six1 H2B-GFP Knock-in Reporter Lines.

Donor plasmids were constructed and cloned into pUC19 using the Infusion Cloning System (Clontech). TALEN sequences were predicted using the TAL Effector Nucleotide Targeter software (Cermak et al., 2011; Doyle et al., 2012).

Pax6 TALENS and Six1 TALENS:. TALENs were generated using the TALEN Toolbox (Addgene) (Sanjana et al., 2012) and performed as described. The donor plasmid (20 ug) and TALEN pairs (5 ug each) were nucleofected (Lonza Kit V) into H9 hESCs (passage 32-36). Nucleofected cells were seeded onto a MEF feeder layer in KSR media plus ROCK inhibitor. After 48 hours, puromycin (1 ug/ml) was added to select for positive clones. Puromycin resistant colonies were then isolated and genomic DNA was extracted and targeting was confirmed using PCR. Further validation included directed differentiation and co-labeling GFP with either Pax6 or Six1 antibody.

RNA Sequencing and Analysis.

Total RNA (Trizol) was isolated from GFP sorted cells (NE, NC and placode) or in bulk (NNE) at day 12 of differentiation in at least duplicates. Sixty million reads were generated and aligned using Tophat v1.2 (Trapnell et al., 2012). Reads were then counted using HTseq (Anders et al., 2015) and differentially expressed genes were calculated using DESeq (Anders and Huber, 2010). Differentially expressed groups analyzed for their gene ontology classification and signaling pathway enrichment using LifeMap Gene Analytics (Edgar et al., 2013). Resulting RNA sequencing datasets are uploaded to GEO.

TFAP2A Knockout Line Generation.

The CRISPR/Cas9 system was used to generate the knockout hESC lines. Briefly, two guide RNAs were predicted using the CRISPR design tool (Cong et al., 2013) and cloned into the TOPO-Blunt vector (Mali et al., 2013)(Life Technologies). Cas9-GFP (5 ug) and both guideRNAs (1 ug each) were nucleofected into H9 hESCs and replated on a Matrigel coated dish in KSR media with ROCK inhibitor. After 24 hours, the cells were sorted for GFP and seeded on a MEF feeder layer in KSR media with ROCK inhibitor. Colonies were then isolated and the targeted region of TFAP2A was amplified by PCR and cloned into the TOPO TA vector and sequenced to identify frame shift mutants.

REFERENCES

1. Anders, S., and Huber, W. (2010). Differential expression analysis for sequence count data. Genome biology 11, R106.
2. Anders, S., Pyl, P. T., and Huber, W. (2015). HTSeq—a Python framework to work with high-throughput sequencing data. Bioinformatics 31, 166-169.
3. Blauwkamp, T. A., Nigam, S., Ardehali, R., Weissman, I. L., and Nusse, R. (2012). Endogenous Wnt signalling in human embryonic stem cells generates an equilibrium of distinct lineage-specified progenitors. Nature communications 3, 1070.
4. Cermak, T., Doyle, E. L., Christian, M., Wang, L., Zhang, Y., Schmidt, C., Baller, J. A., Somia, N. V., Bogdanove, A. J., and Voytas, D. F. (2011). Efficient design and assembly of custom TALEN and other TAL effector-based constructs for DNA targeting. Nucleic acids research 39, e82.
5. Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nature biotechnology 27, 275-280.
6. Chambers, S. M., Qi, Y., Mica, Y., Lee, G., Zhang, X. J., Niu, L., Bilsland, J., Cao, L., Stevens, E., Whiting, P., et al. (2012). Combined small-molecule inhibition accelerates developmental timing and converts human pluripotent stem cells into nociceptors. Nature biotechnology 30, 715-720.
7. Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Chemically defined conditions for human iPSC derivation and culture. Nature methods 8, 424-429.
8. Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.
9. Dincer, Z., Piao, J., Niu, L., Ganat, Y., Kriks, S., Zimmer, B., Shi, S. H., Tabar, V., and Studer, L. (2013). Specification of functional cranial placode derivatives from human pluripotent stem cells. Cell reports 5, 1387-1402.
10. Doyle, E. L., Booher, N.J., Standage, D. S., Voytas, D. F., Brendel, V. P., Vandyk, J. K., and Bogdanove, A. J. (2012). TAL Effector-Nucleotide Targeter (TALE-NT) 2.0: tools for TAL effector design and target prediction. Nucleic acids research 40, W117-122.
11. Edgar, R., Mazor, Y., Rinon, A., Blumenthal, J., Golan, Y., Buzhor, E., Livnat, I., Ben-Ari, S., Lieder, I., shitrit, A., et al. (2013). LifeMap Discovery: the embryonic development, stem cells, and regenerative medicine research portal. PloS one 8, e66629.
12. Groves, A. K., and LaBonne, C. (2014). Setting appropriate boundaries: fate, patterning and competence at the neural plate border. Developmental biology 389, 2-12.
13. Li, W., and Cornell, R. A. (2007). Redundant activities of Tfap2a and Tfap2c are required for neural crest induction and development of other non-neural ectoderm derivatives in zebrafish embryos. Developmental biology 304, 338-354.

14. Lippmann, E. S., Estevez-Silva, M. C., and Ashton, R. S. (2014). Defined human pluripotent stem cell culture enables highly efficient neuroepithelium derivation without small molecule inhibitors. Stem cells 32, 1032-1042.
15. Luo, T., Lee, Y. H., Saint-Jeannet, J. P., and Sargent, T. D. (2003). Induction of neural crest in Xenopus by transcription factor AP2alpha. Proceedings of the National Academy of Sciences of the United States of America 100, 532-537.
16. Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.
17. Maroof, A. M., Keros, S., Tyson, J. A., Ying, S. W., Ganat, Y. M., Merkle, F. T., Liu, B., Goulburn, A., Stanley, E. G., Elefanty, A. G., et al. (2013). Directed differentiation and functional maturation of cortical interneurons from human embryonic stem cells. Cell stem cell 12, 559-572.
18. Mica, Y., Lee, G., Chambers, S. M., Tomishima, M. J., and Studer, L. (2013). Modeling neural crest induction, melanocyte specification, and disease-related pigmentation defects in hESCs and patient-specific iPSCs. Cell reports 3, 1140-1152.
19. Sanjana, N. E., Cong, L., Zhou, Y., Cunniff, M. M., Feng, G., and Zhang, F. (2012). A transcription activator-like effector toolbox for genome engineering. Nature protocols 7, 171-192.
20. Schorle, H., Meier, P., Buchert, M., Jaenisch, R., and Mitchell, P. J. (1996). Transcription factor AP-2 essential for cranial closure and craniofacial development. Nature 381, 235-238.
21. Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nature protocols 7, 562-578.
22. Xie, W. F., Kondo, S., and Sandell, L. J. (1998). Regulation of the mouse cartilage-derived retinoic acid-sensitive protein gene by the transcription factor AP-2. The Journal of biological chemistry 273, 5026-5032.

6.2 Example 2: Derivation of Diverse Hormone-Releasing Pituitary Cells from Human Pluripotent Stem Cells Summary Human pluripotent stem cells (hPSCs) represent a potentially unlimited cell source for applications in regenerative medicine. Hormone producing cells may be particularly suitable for cell therapy applications, and the treatment of pituitary gland dysfunction may be a potential therapeutic target. Previous studies have demonstrated the derivation of pituitary lineages from mouse ESCs using 3D organoid cultures that mimic the developmental interactions involved in pituitary gland development in vivo.

The present example describes a simple and highly efficient strategy to derive anterior pituitary lineages from hPSCs using chemically defined monolayer culture conditions suitable for cell manufacturing. We demonstrate that purified placode lineage can be induced towards pituitary fate using defined cues in the absence of complex co-culture conditions. Using single cell gene expression analysis we define the diversity of hPSC-derived lineages with >80% pituitary hormone-expressing cells. Finally we demonstrate basal and stimulus-induced hormone release in vitro and engraftment and hormone release in vivo after transplantation into a murine model of pituitary dysfunction.

Here we report the efficient derivation of hormone-producing cells of the anterior pituitary from hPSC under fully defined cGMP-ready monolayer culture conditions. Additionally we present single cell mRNA expression data to address the diversity of anterior pituitary subtypes that can be achieved in vitro. Furthermore, we show that the cells generated are functional in vitro by responding to appropriate stimuli and secrete hormones in an animal model of hypopituitarism in vivo. Our data indicate, in contrast to earlier reports using mESC, that pituitary cell fate can be induced independent of mimicking the complex 3D organization of the developing gland and without direct contact with hypothalamic cells thought to induce anterior pituitary identity. We demonstrate that by providing appropriate signals to purified placode precursor cells pituitary identity can be specified at high efficiency and that further manipulation of morphogen gradients allows controlled changes in the relative composition of hormonal cell types. We provide a robust differentiation platform to access diverse hormone producing cell types suitable for further development towards a cell-based treatment of hypopituitarism.

Results

Derivation of Cranial Placode from hPSC Under Fully Defined Conditions

We have recently reported the generation of cranial placode including the adenohypophysis from hPSCs (Dincer et al., 2013). However our previous protocol was not optimized to generate pituitary lineage cells and contained several ill-defined reagents such as knockout serum replacement (KSR), Matrigel and mouse embryonic fibroblast (iMEF) feeders. Those components are a significant source of variability for the robustness of a given differentiation protocol and complicate the development of cell therapies suitable for human translation. Furthermore, the efficiency of generating anterior pituitary lineage cells from PSCs has been low in all published studies for both mouse and human cells. Finally, it was important to conclusively assess whether direct interaction with hypothalamic cells is required during the induction process as suggested by the 3D culture studies in mouse ESCs (Suga et al., 2011) or whether a limited number of defined signals are sufficient to trigger pituitary fate.

The first step in the protocol is the efficient induction of early cranial placode cells competent to generate anterior pituitary lineages. Our novel cranial placode induction protocol relies on serum-free monolayer-based induction conditions and uses fully defined cGMP-ready components. The specific signals used to trigger placode induction are based on the developmental signals thought to specify placode induction in vivo (FIG. 15A). We observe that exposure to moderate concentrations of BMP4 is required for the efficient induction of cranial placode fate. Furthermore lens appears to be the "default" placode fate under those conditions (FIG. 22) in agreement with studies in the developing chick embryo in vivo that also report a lens default in the absence of FGF signals (Bailey et al., 2006). A detailed temporal expression analysis revealed the rapid loss of pluripotency markers and the robust induction of key placode genes such as SIX1, EYA1 and DLX3/5 by 6 days of differentiation at both mRNA (FIG. 15B) and protein (FIG. 15C) levels. Transcripts marking the presence of contaminating cell types such as SOX10 (neural crest), SOX17 (endoderm), T/Brachyury (Mesoderm) or MYOD (myogenic lineages) were not induced under those conditions (FIG. 15B). Our previous study reported PAX3+ trigeminal placode as the "default" identity of hPSC-derived placode cells (Dincer et al., 2013). Our current protocol, using the defined placode induction conditions, shows PAX6 rather than PAX3 expression (FIG. 15C). To further quantify the yield and selectivity of placode induction and PAX6 expression we used hESC genetic reporter lines for SIX1::H2B-GFP (FIG. 25)., PAX6::H2B-GFP, SOX10-GFP (Chambers et al., 2012; Mica et al., 2013). Flow cytometry at day 6 and day 11 of differentiation confirmed robust induction of PAX6 positive and SIX1 positive anterior cranial placode in the absence of contaminating SOX10 positive neural crest cells (FIG. 23).

Patterning of Anterior Pituitary from hPSC-Derived Cranial Placode

The complex morphogenetic development of the pituitary gland occurs during early embryonic stages (~E1i) in mouse). Both the anterior and intermediate lobes of the gland are derived from oral ectoderm, which corresponds to the pituitary placode while the posterior pituitary gland develops from the neural ectoderm (FIG. 16A). Inductive tissue interactions as well as various defined signaling pathways including FGFs, BMPs and SHH have been shown to be important for pouch invagination, proper gland development and hormonal subtype specifications in vivo (FIG. 16A, upper panel) (for review see (Zhu et al., 2007)). Here we assessed whether modulating those key-signaling pathways directing hPSC differentiation towards placode fates is sufficient to trigger pituitary identity (FIG. 16A, lower panel). Our data show that timed exposure to SHH, FGF8 and FGF10 robustly induces the genes associated with anterior pituitary development including PITX1/2, LHX3/4 as well as HESX1 and SIX6 (FIG. 16B). Expression under the pituitary differentiation condition was also confirmed on the protein level using antibodies against PITX1, LHX3, LHX4 and SIX6 (FIG. 16C).

Figure 31A:
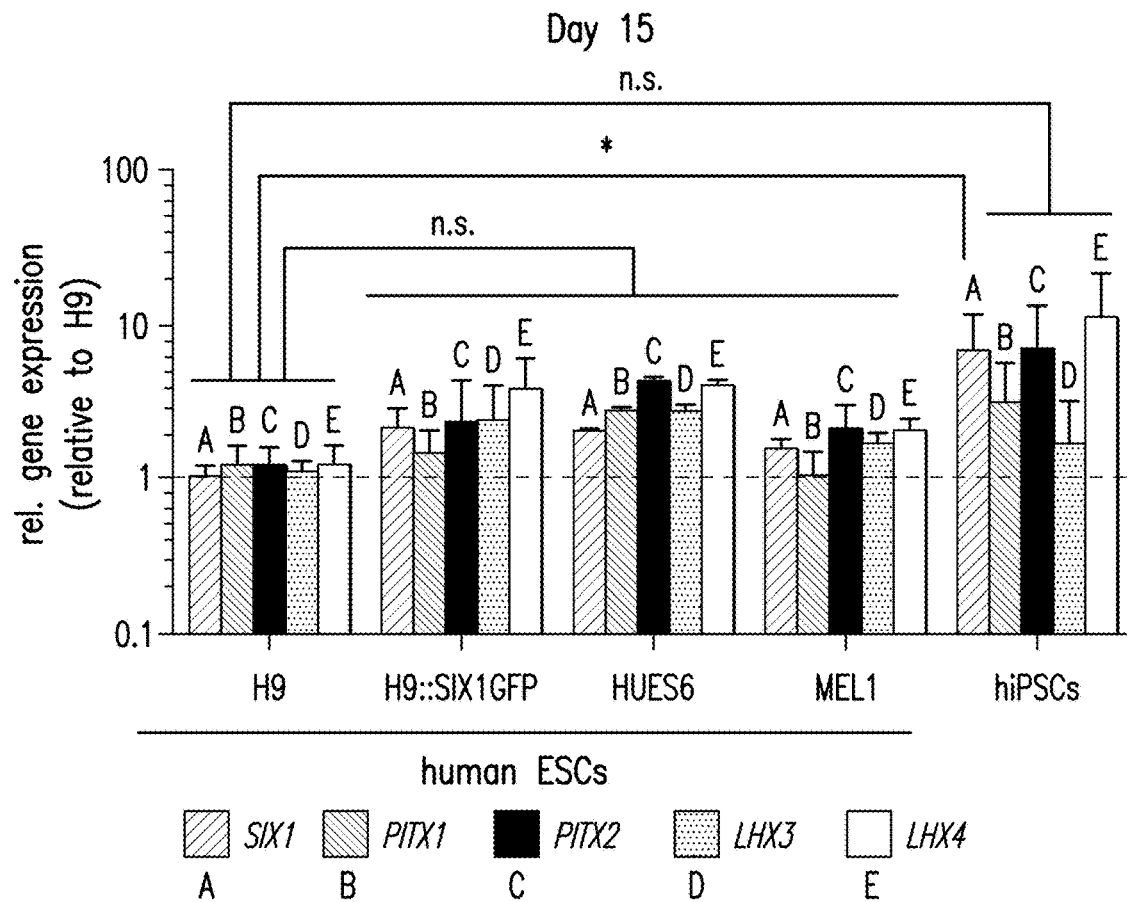
Figure 31B:
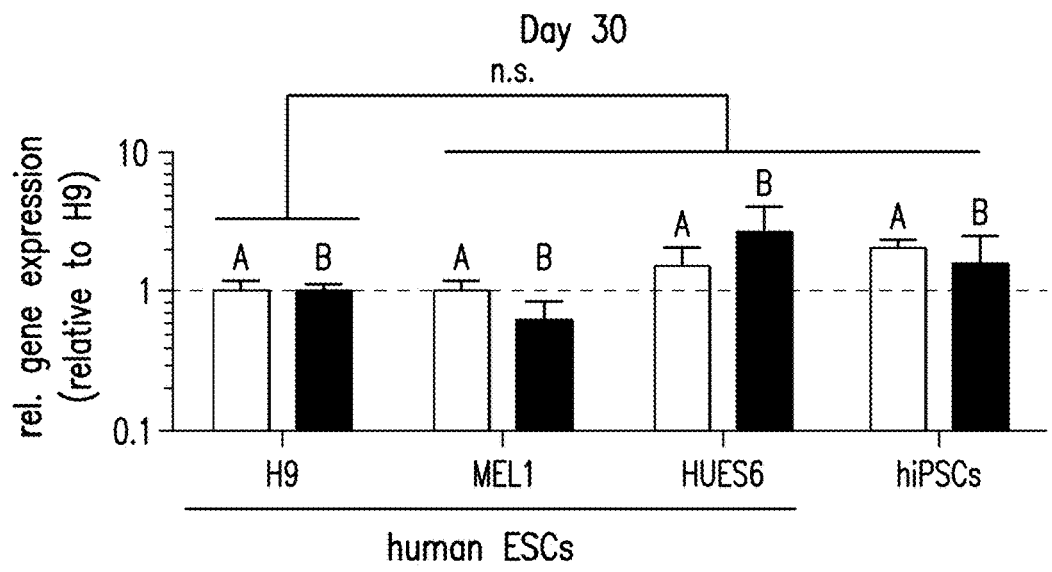
Figure 31C:
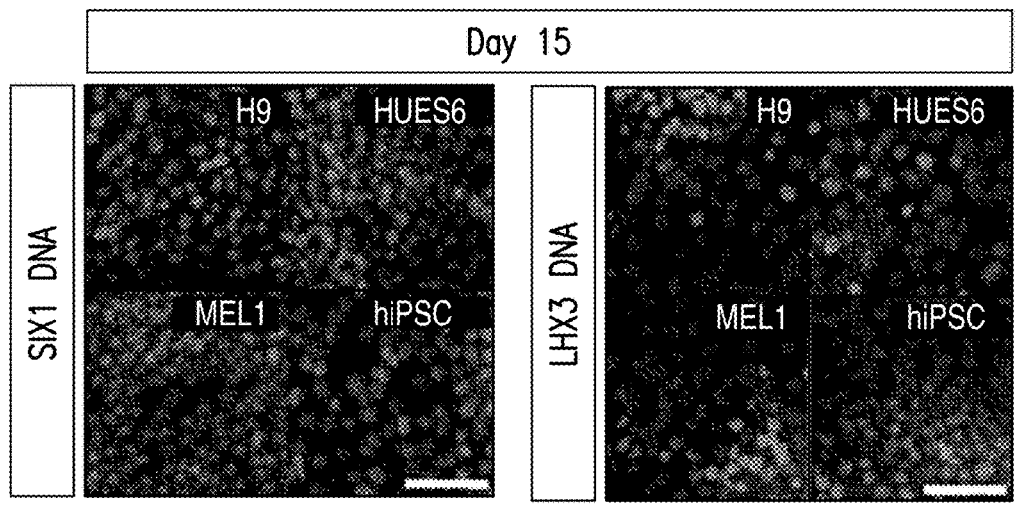
Figure 31D:
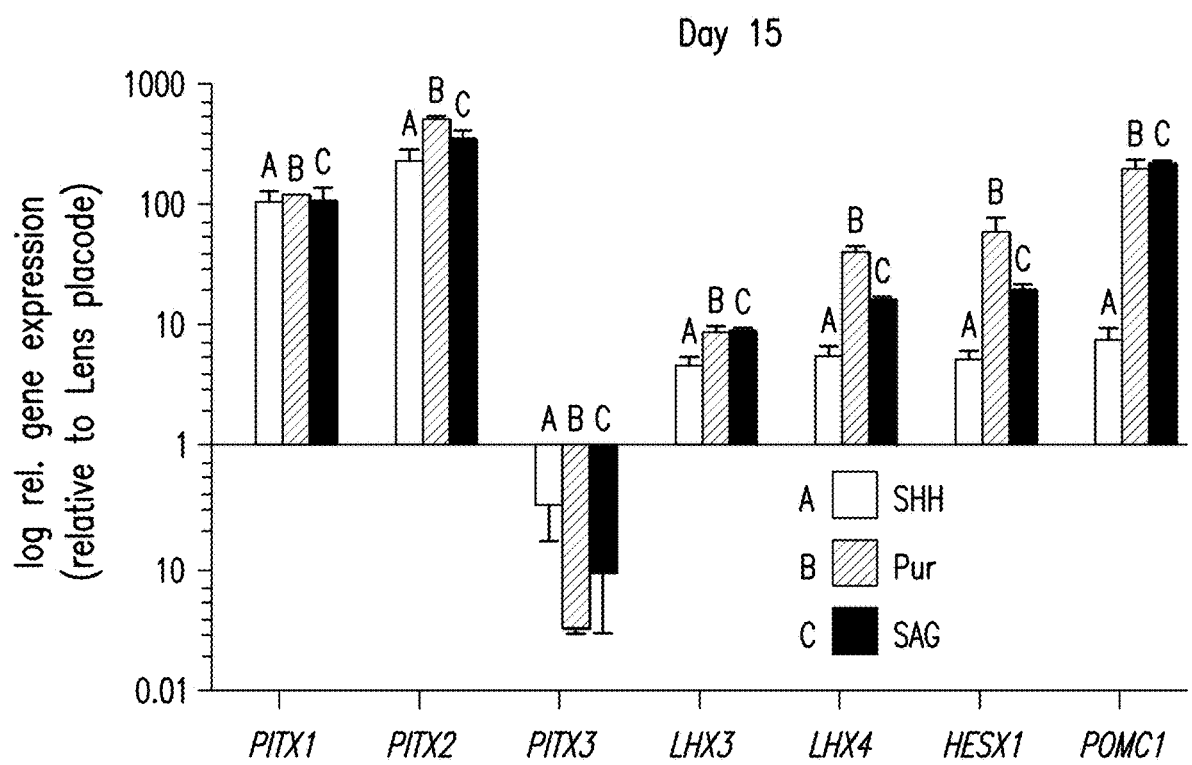
Figure 31E:
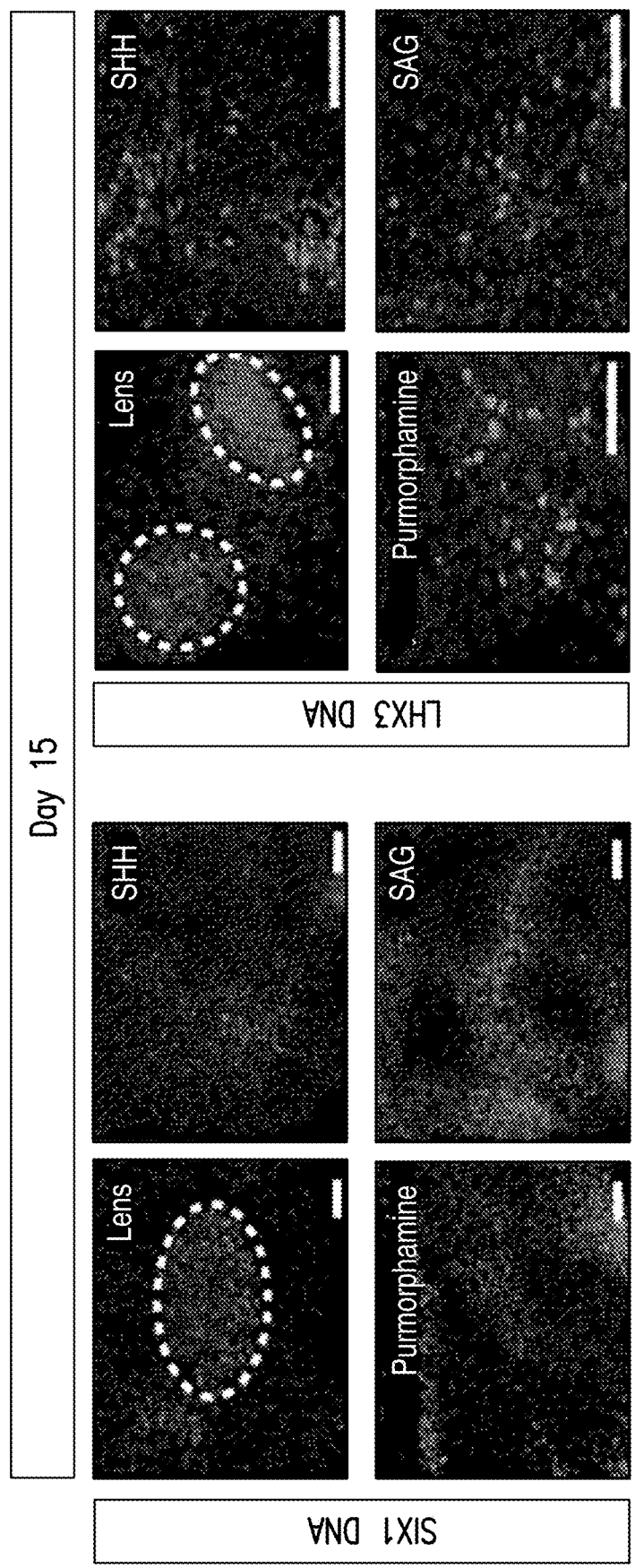

We compared our cGMP-ready E8/E6-based induction protocol with our published KSR-based placode induction protocol (PIP) (Dincer et al., 2013). To compensate for KSR lot-to-lot variability, which can dramatically affect differentiation efficiency, we performed PIP using two distinct concentrations of the BMP inhibitor LDN-193189. After 15 days of differentiation, the cells were analyzed using qRT-PCR probing for pan-placodal markers such as SIX1 as well as the pan-pituitary markers PITX1, PITX2, LHX3, and LHX4. In addition, the neuroectoderm marker PAX6 and the non-neural ectoderm transcription factor TFAP2A were included in the analysis (FIG. 30A). Cell identity was further confirmed at the protein level using immunofluorescence staining for SIX1 and LHX3 (FIG. 30B). The KSR lot used for these experiments failed to effectively induce pituitary or placode identity as shown by the low expression of SIX1 and TFAP2A and high expression of PAX6. Lowering the LDN-193189 concentration was able to partially but not fully rescue that effect compared with our new E8/E6-based protocol. The cGMPready protocol presented here works reliably and with comparable efficiency across various hESC and hiPSC lines (FIGS. 31A-31C). Furthermore, we confirmed that the recombinant protein SHH can be replaced by small-molecule smoothened agonists such as purmorphamine and SAG (FIGS. 31D and 31E). However, despite robust induction of anterior pituitary-lineage markers, we observed an increase in cell death when using the small-molecule-based induction conditions, which prompted us to use recombinant SHH for subsequent studies.

Interestingly, medium conditioned by hPSC-derived hypothalamic anlage (Maroof et al., 2013; Merkle et al., 2015) (FIG. 24) was not sufficient to robustly induce pituitary marker expression (FIG. 16B). Specifically, there was a lack of induction of LHX4 as well as HESX1 and SIX6 when using CM only. LHX4 and SIX6 have been implicated in pituitary progenitor expansion, which could explain the reduced total numbers of cells generated in the presence of hypothalamic lineage CM. There is evidence in mouse ESCs that direct tissue interaction with the hypothalamic anlage may be needed during pituitary development (Suga et al., 2011). However, our data suggest that defined extrinsic cues may be sufficient to induce pituitary placode identity. In order to more directly assess the role of hypothalamic tissue during pituitary placode induction and differentiation, we made use of the SIX1::H2BGFP reporter cell line (FIG. 25). Early placode cells differentiated under default conditions were sorted at day 6 of differentiation for SIX1::H2B-GFP expression followed by further differentiation under either lens conditions (default), in the presence of SHH, FGF8 and FGF10 (pituitary conditions) or in the presence of medium conditioned by hPSC-derived hypothalamic neuroectoderm (FIG. 17A). Gene expression analysis revealed that even in purified SIX1::H2B-GFP+ cells, that are devoid of any hypothalamic lineage cells, our defined induction conditions are sufficient to induce expression of all the key pituitary markers. In contrast, hypothalamic CM failed to induce LHX4 expression above levels observed under the default lens conditions (FIG. 17B). Since pituitary induction was started later compared to the standard protocol to exclude patterning of the preplacode tissue (day 6 vs. day 4) the levels of induction, especially of LHX4, was slightly lower in SIX1::H2B-GFP purified cells compared to our standard pituitary placode induction protocol on unsorted cells. Alternatively, the sorting process could also decrease induction efficiency.

In a different set of experiments we co-cultured the day 6 sorted SIX1:H2B-GFP+ cells in direct contact with hPSC-derived hypothalamic anlage, and stained the cells for the plan-placodal marker SIX1 as well as the pituitary marker LHX3 at 9 days of additional differentiation (day 15). As additional controls we included the "default" lens conditions as well as our standard pituitary condition and hypothalamic conditioned medium (FIG. 17A). While the lens condition started to form lentoid-like clusters and downregulated SIX1 expression the pituitary condition resulted in SIX1/LHX3 double positive cells. The conditioned medium was able to maintain SIX1 while inducing only weak levels of LHX3 expression. Although the co-culture condition was able to maintain SIX1 expression, no LHX3 expression was observed (FIG. 17C). These findings support the idea that exposure to the correct extrinsic developmental cure is sufficient to direct hPSC into pituitary lineages cells in the absence cell contact mediated signal from hypothalamic lineage cells. While we cannot rule out that further optimization of the co-culture conditions may eventually yield pituitary lineage cells the use of defined signals acting on a defined lineage of hPSC-derived cells may reduce variability inherent to more complex co-culture based systems, and present a platform more suitable for subsequent translational applications.

hPSC Derived Adenohypophyseal Cells are Functional

The main function of the adenohypophysis is to secrete 6 different hormones controlling key events in the human body including stress response (adrenocorticotropic hormone [ACTH]), skeletal growth (growth hormone [GH]), metabolism (thyroid-stimulating hormone [TSH]) and reproductive functions (prolactin [PRL], follicle-stimulating hormone [FSH], luteinizing hormone [LH]). We therefore assessed the presence of hormonal subtypes in our culture after 30 days of differentiation. We were able to detect ACTH, GH, PRL as well as FSH and LH expressing cells in our culture (FIG. 18A). ELISA measurements of cell culture supernatant confirmed that the cells exhibit a basal rate of secretion for ACTH, GH and FSH (FIG. 18B). Hormone release in the anterior pituitary gland is tightly regulated by several feedback mechanisms from various factors secreted by various target organs as well as from upstream factors released by hypothalamus cells through the portal veins. Therefore the functional response of pituitary cells needs to be closely linked to those various regulatory stimuli. hPSC-derived pituitary cells at day 30 of differentiation showed induced release of ACTH in response to stimulation with CRF, stressin or urocortin. In contrast, exposure to inappropriate stimuli such as Ghrelin or somatocrinin did not trigger ACTH release (FIG. 18C). On the other hand, somatocrinin but not CRF exposure triggered robust increase in GH release (FIG. 18D). Finally, we were able to show induction of FSH upon exposure to Nafarelin (FIG. 18E).

Single Cell Gene Expression Analysis Reveals Diversity of Hormonal Lineages

Figure 19A:
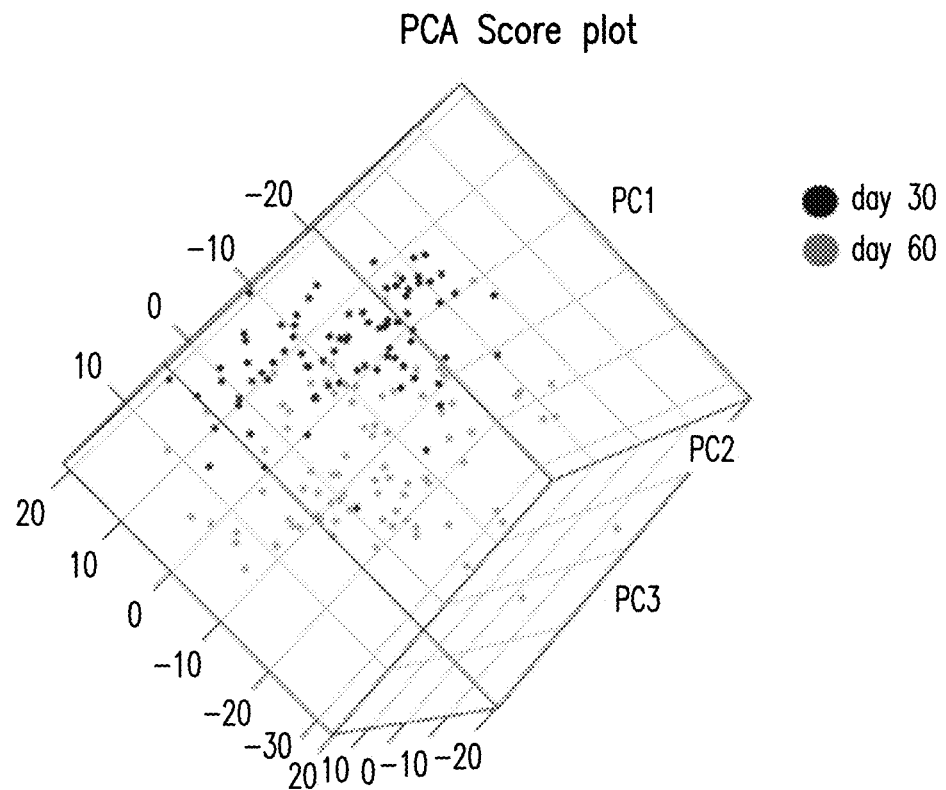
Figure 19B:
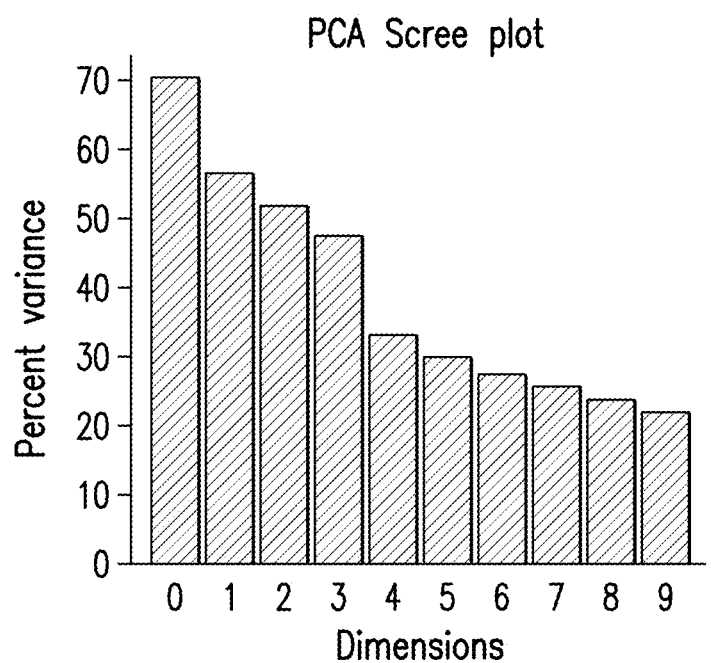
Figure 19C:
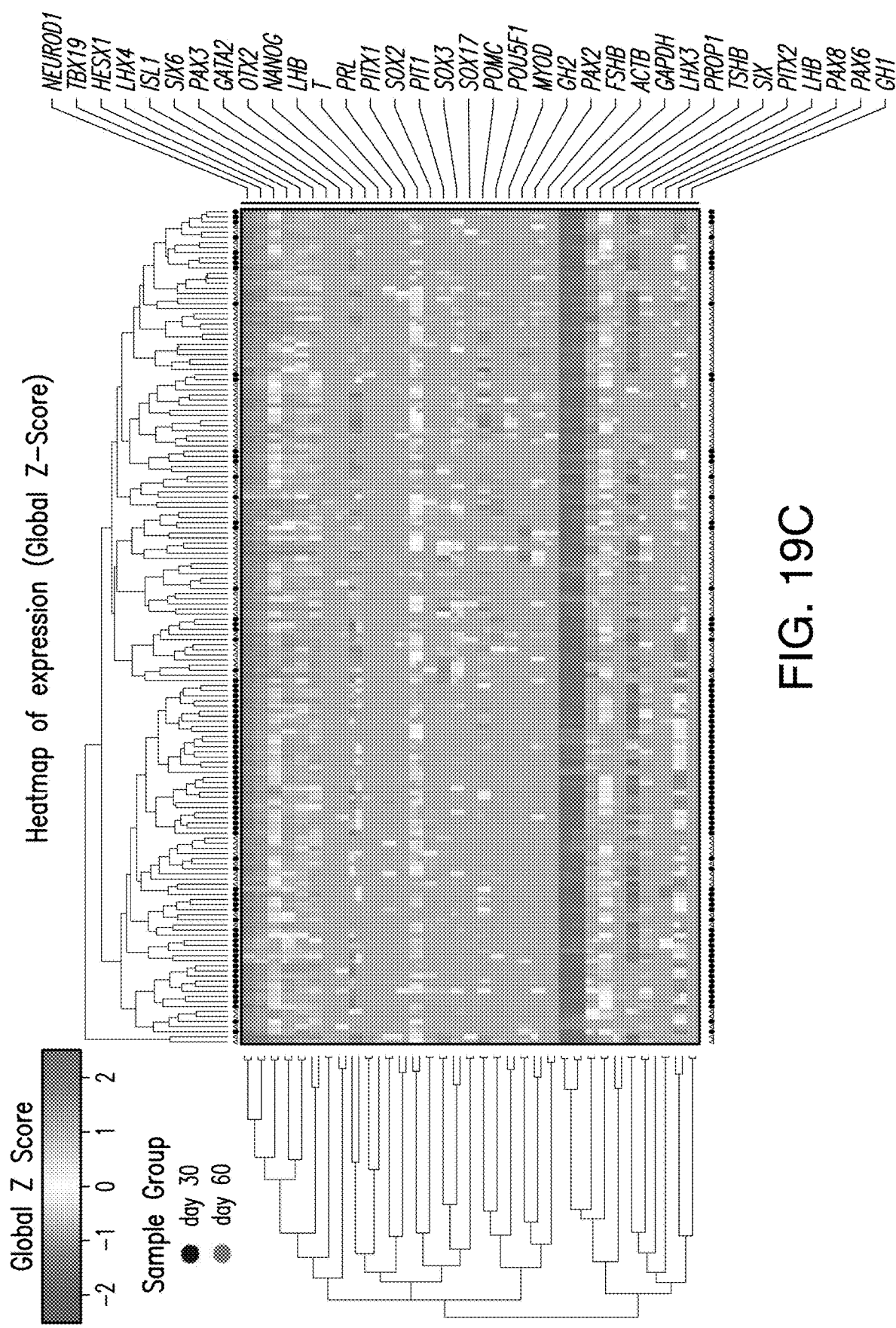

Differentiation of the various hormonal progenitor lineages within the adenohypophysis (Tabar, 2011) is a tightly regulated spatial and temporal process involving various patterning events (FIG. 16A). To address the diversity of progenitor fates in our hPSC-based culture system we performed a single cell qRT-PCR experiment using the Fluidigm platform. We probed for 34 genes spanning the entire pituitary development from pluripotent stem cells to mature hormone-expressing cells. We also included primers to assay for potential mesodermal or endodermal contaminants such as T (Brachyury), MYOD and SOX17. Principal component analysis (PCA) of cells at day 30 and day 60 of differentiation showed that most cells show a clear time dependent change with only few cells moving ahead of schedule (i.e. day 30 cells showing a day 60 profile) or being delayed (i.e. day 60 cells retaining a day 30 signature) (FIG. 19A, B). The scree plot (FIG. 19B) defined the PCA components that explain most of the variability of the data. Hierarchical clustering confirmed a separation of cells largely along the time axis resulting in two main clusters interspersed with several smaller subclusters (FIG. 19C).

In addition, heatmaps based on the raw ct values are provided in FIG. 32. We further validated our single-cell data by immunofluorescence staining in day-30 cultures for the progenitor marker HESX1, and for NEUROD1, a more mature marker transiently expressed in corticotrophs. Immunofluorescence analysis at day 15 of differentiation served as negative control for NEUROD1 (FIG. 33A). We confirmed co-labeling of HESX1 and NEUROD1 in the same cell at day 30 of differentiation. However, the levels of HESX1 expression were much lower at day 30 compared with day 15.

Our analysis revealed that day 30 cultures contain a high percentage of pituitary like cells with ~70% of cells co-expressing the pituitary markers PITX1 and LHX3. This percentage further increased by day 60. On the other hand, by day 30 we could only detect 4 cells (~5% of all cells analyzed) expressing T, SOX17 or MYOD suggesting a low percentage of potential contaminants. Most of the cells expressed TBX19 (TPIT) a transcription factor shown to be key for the development of the POMC lineage in the pituitary gland (Lamolet et al., 2001). Furthermore, most cells (~84%) expressed the pan placodal marker SIX1. Most SIX1+ cells also expressed PAX6, compatible with pituitary placode fate. However we also observed expression of other placode fates including PAX2 (epibranchial), PAX3 (trigeminal) or PAX8 (otic) in small subsets of cells representing a total of 20% of the cells in combination.

Figure 19E:
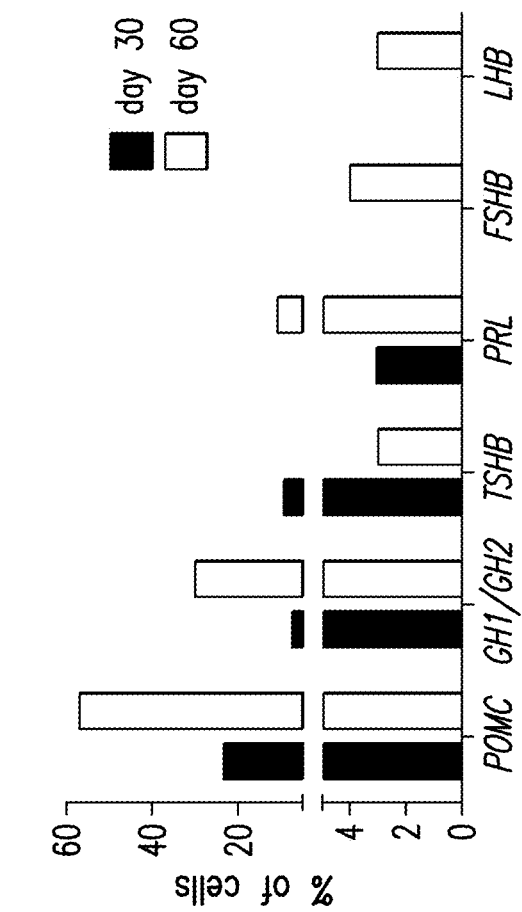
Figure 19D:
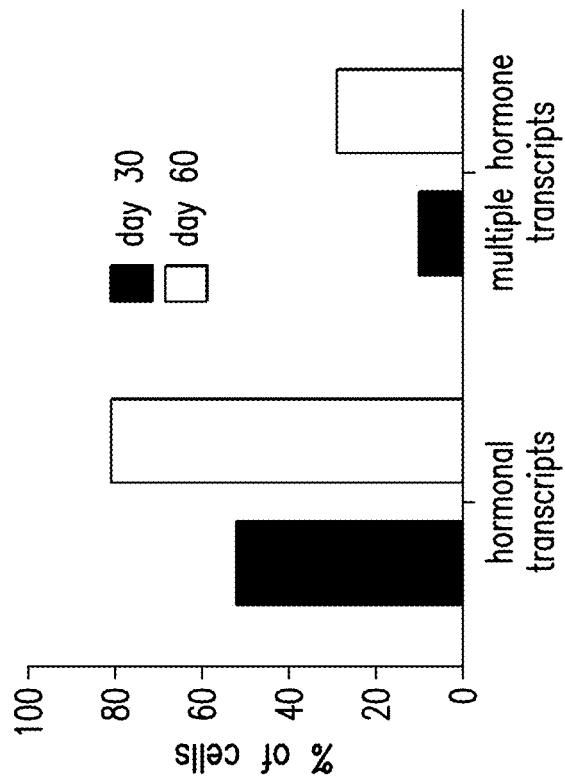

The ultimate functional unit of the anterior pituitary is cells expressing and secreting specific hormones. Our single cell analysis showed that at day 30 of differentiation approximately 50% of the cells expressed at least one hormonal mRNA species. This percentage increased to about 80% by day 60, indicating further in vitro maturation (FIG. 19D). There have been reports suggesting that both the developing and adult rodent pituitary gland can contain cells that express more than a single hormone (Nunez et al., 2003; Villalobos et al., 2004). Indeed, in our hPSC-derived cultures we could detect expression of more than one hormonal transcript ("plurihormonal") in 10% of the cells by day 30 of differentiation. By day 60 of differentiation, this percentage increased to ~30% of the total cell population (FIG. 19D). We found that the majority of plurihormonal cells by day 60 expressed both POMC and GH (~10%). Cells expressing more than two transcripts were only detected by day 60 and always contained POMC (FIG. 26).

The most frequent hormonal transcript expressed in hPSC-derived pituitary cells at day 30 of differentiation was POMC (30% of total cells), which is thought to emerge from the dorsal pituitary anlage. The more ventral cell types such as GH or TSH made up a lower percentage (about 20%) of the total cell population by day 30 of differentiation. PRL was expressed in an even smaller subset of cells. Finally, FSH and LH, the two most ventral cell types, which appear only at later stages of development, were not detected by day 30 (FIG. 19E). At day 60 of differentiation the number of POMC and GH expressing cells increased to 55% and 30% respectively. Still only few cells expressed FSH and LH at day 60 of differentiation (FIG. 19E). In addition to the single-cell PCR we characterized the cell-surface marker expression of the day-30 culture using the commercially available BD Lyoplate screening kit (FIG. 34).

Dorsal-Ventral Patterning of Anterior Pituitary Cells In Vitro Using Morphogens

Hypopituitarism is a very diverse and complex disease. Depending on the cause of pituitary dysfunction the type of hormones affected can vary. For example GH deficits are commonly observed in patients with inborn genetic disease (van Gelderen and van der Hoog, 1981) but can also occur in patients following radiation treatment (Sklar and Constine, 1995). In contrast, lymphocytic hypophysitis, an auto-immune disease of the pituitary gland, affects primarily ACTH (Rivera, 2006). Therefore, for the broad application of hPSC derived pituitary cells in the future, cell replacement therapy may need to be customized to the specific needs of a given patient population. Since our standard conditions mostly yield dorsal, ACTH+ cells, we asked whether additional signals can be used to enhance the production of more ventral cell types.

Figure 20A:
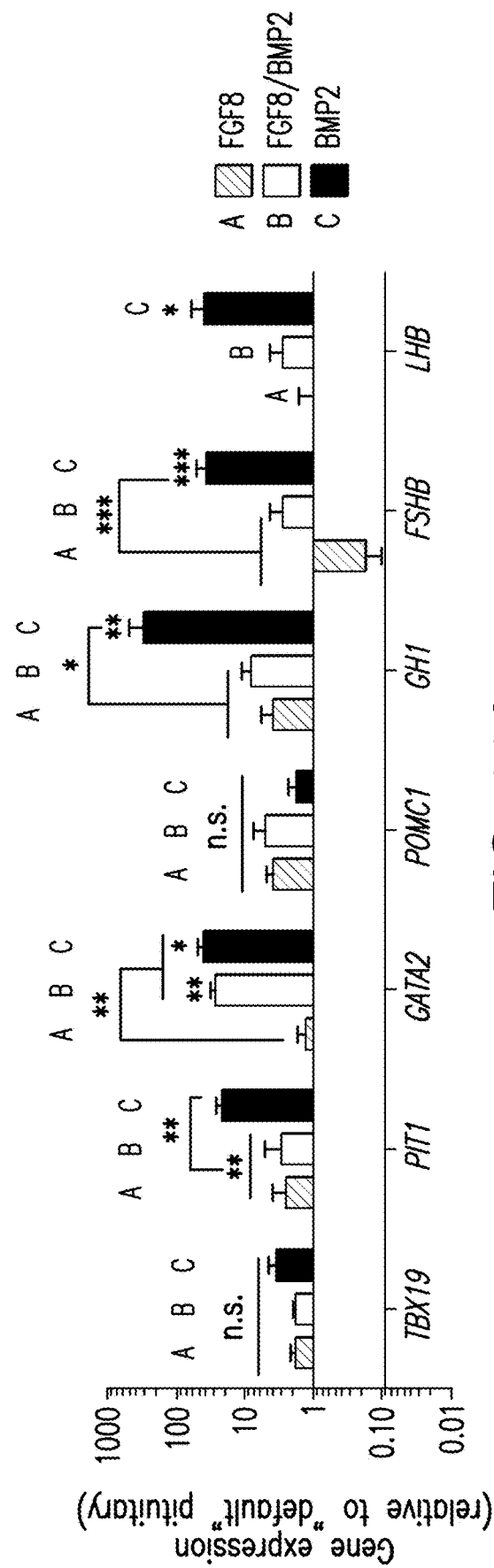

It has been shown that FGF8 and BMP2 signaling gradients play an important role in dorsal-ventral patterning of the mouse pituitary gland (Rosenfeld et al., 2000) (FIG. 16A). We therefore treated pituitary-lineage cells with high concentration of either FGF8 (dorsalizing) or BMP2 (ventralizing), or with a mixture of the two patterning factors at intermediate concentration levels to mimic morphogen gradients occurring in vivo. Gene expression studies for key transcription factors of pituitary precursor lineage and hormonal subtypes confirmed the need for BMP2 to generate the most ventral cell types. FSHB and LHB were significantly upregulated in the presence of BMP2 while FGF8 exerted a negative effect on FSHB yield (FIG. 20A).

Figure 20B:
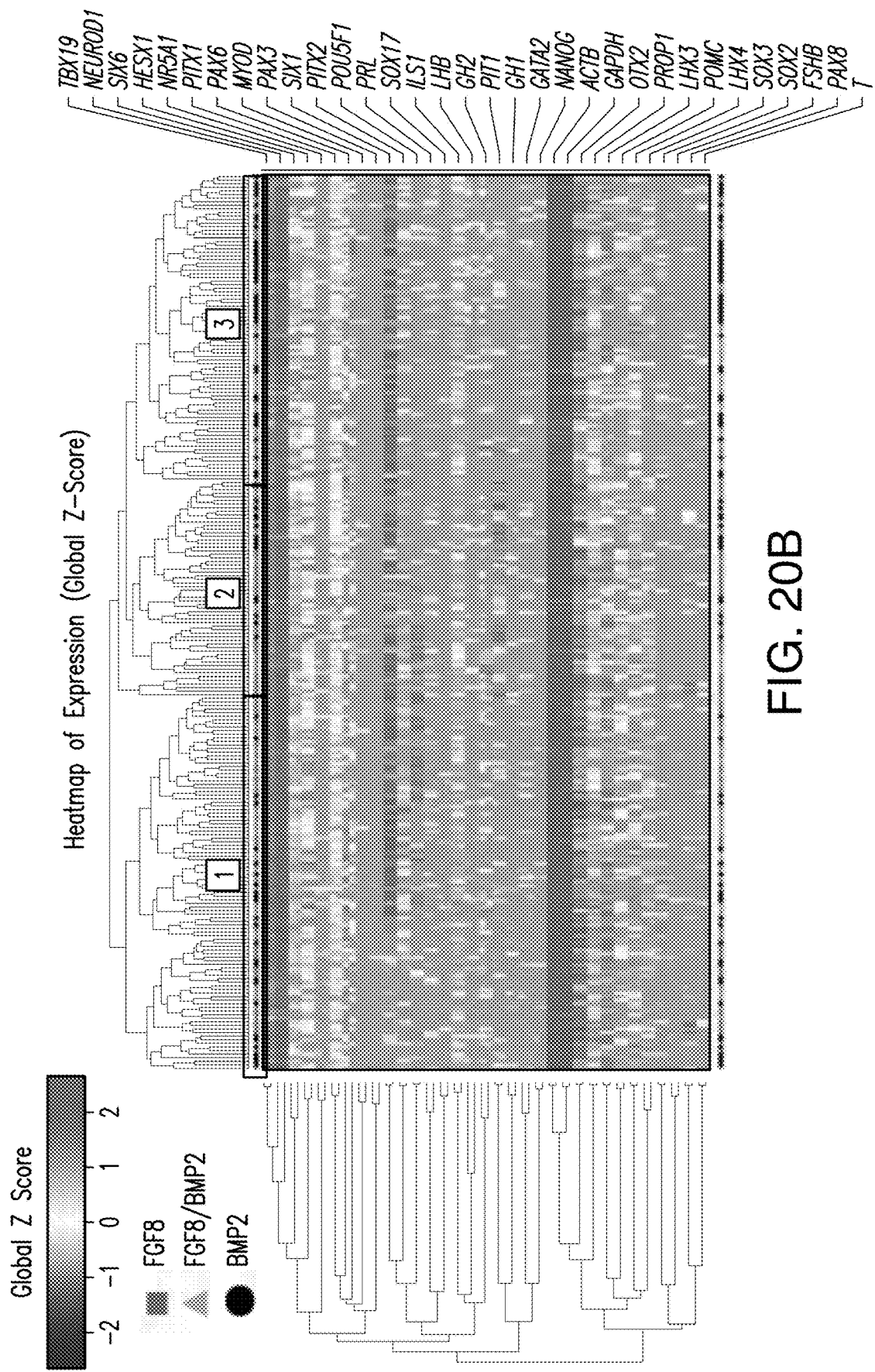

We next performed single cell qRT-PCR analysis to increase the resolution of our analysis. Unsupervised hierarchical clustering of single cells at day 60, treated with FGF8, BMP2 or a combination of both factors, revealed three larger clusters of cells (FIG. 20B). In addition, heatmaps based on the raw ct values are provided in FIG. 32. Cells corresponding to each of the three treatments were observed in every cluster. However, 49% of all the total cells in cluster 3 were from the BMP2 treated group while 56% of all the cells in cluster 2 were derived from the FGF8 group. Cluster 1 represented cells from all 3 treatments in roughly equal proportions. By analyzing single cell expression for each of the anterior pituitary hormones we were able to confirm findings predicted from mouse in vivo studies (Rosenfeld et al., 2000) in our hPSC-based culture system. High concentrations of FGF8 led to an increase in the number of cells expressing POMC compared to high concentrations of BMP2 (75% versus 40% respectively) (FIG. 20C). Furthermore intermediate concentrations of both signaling molecules resulted an increase of cells expressing GH and TSHB compared to either FGF8 or BMP2 alone (FIG. 20C). Finally, high concentrations of BMP2 not only decreased the number of ACTH+ dorsal cell types but also increased the number of ventral cell types expressing FSHB and LHB.

We next validated our single cell qRT-PCR data using traditional immunofluorescence staining for 4 different hormones under the three culture conditions (FGF8, FGF8/BMP2, BMP2; FIG. 20D). Quantification of the immunocytochemical data confirmed a bias towards dorsal ACTH expressing cells in the FGF8 treated culture. PRL and GH were the most abundant hormones observed following the combination treatment with FGF8/BMP2 while FSH was the most abundant cell type in BMP2 treated cultures (FIG. 20E). POMC is the precursor polypeptide of ACTH and 44 amino acids are removed during translation, which ultimately gives rise to the hormone ACTH.

Grafted Human ESC-Derived Anterior Pituitary Cells are Functional in an In Vivo Model of Hypopituitarism To assess the ability of hPSC-derived pituitary cells to survive and function in vivo we transplanted day 30 cells into hypophysectomized rats. After surgical removal of the pituitary gland (FIG. 21A) using parapharyngeal methods, hypopituitarism in the rats was confirmed by measuring ACTH levels in the blood. Rats that were successfully hypopysectomized were divided into 2 experimental groups, the sham group (n=4) receiving Matrigel only injections and the grafting group (n=7) receiving Matrigel containing hESC-derived pituitary cells (day 30, standard conditions without BMP2 treatment). Following transplantation of $2 \times 10^6$ cells subcutaneously, both treatment and control groups were followed for 7 weeks post-transplantation monitoring pituitary hormone levels in the blood stream (FIG. 21B-D). Starting at 3 weeks after transplantation, hormone levels in the grafted group started to increase compared with the 1-week time point while the levels in the sham group remained largely unchanged. ACTH levels remained at constantly higher levels in the grafted versus control group for the 7 week period of the experiment (FIG. 21B). Compared to ACTH levels observed in unlesioned animals, the grafted group recovered about 60% of the ACTH levels (data not shown). Increases in the level of two other hormones, namely GH and LH were more variable and did not reach significance at all the time points tested. However we could detect significant increases in the GH levels 3 and 7 weeks after transplantation (FIG. 21C). No significant increase in LH level was observed (FIG. 21D).

Hormone levels in grafted animals were compared with levels in intact agematched rats and found to be ~40% for ACTH, ~28% for GH, and ~20% for PRL (FIG. 35). In a final step to evaluate the function of the transplanted cells we performed measurements of the downstream factors affected by hormone secretion. Upon release of ACTH there is an increase in glucocorticoids secreted by the adrenal glands as part of the normal HPA-axis response (Webster and Sternberg, 2004). In humans, ACTH triggers release of cortisol whereas the main glucocorticoid in rodents is corticosterone (Wand, 2008). We therefore measured corticosterone levels in both experimental groups (FIG. 21E). The grafted group showed a consistently higher level of corticosterone resulting in a statistical significant difference by 7 weeks after transplantation. Those data indicate that human ACTH released by hPSC-derived cells can trigger steroid hormone release from the host adrenal gland. At 7 weeks after transplantation, the animals were sacrificed and the graft was analyzed histologically (FIG. 21F-G). We were able to detect cells expressing each of the 6 anterior pituitary hormones with the graft (FIG. 21F). Those data confirm in vivo cell survival and suggest further in vivo differentiation and maturation of the cells. Stereological quantification of the grafts showed an average of $3.08 \times 10^6 \pm 0.42 \times 10^6$ (average ±SD; n=3) human cells per graft, with the majority (>95%) having a placode identity, as determined by co-expression of SIX1 and human nuclear antigen (hNA) by immunohistochemistry. The proportion of Ki67-positive proliferating cells in the graft was 9.6%±0.6% (average ±SD; n=3) of the hNA+ population. The entire graft stained negative for the pluripotency-associated surface markers SSEA-4 and Tral-60. No signs of tumors were detected up to 7 weeks after transplantation. Stereological quantification of the grafts showed an average of 18212±2969 ACTH$^+$ cells per animal (optical fractionator method), with a graft volume of 81±10 mm$^3$ graft (Cavalieri estimator; average ±SD; n=3).

Methods

ESCs and Culture Conditions

The human pluripotent stem cells H9 (WA-09, XX, passage 35-50), MEL-1 (XY, passage 20-40), HUES-6 (XX, passage 24-40), hiPSCs (in-house generated hiPSCs derived from the fetal fibroblast cell line MRCS (ATCC CCL-171) (Chambers et al., 2009), XY, passage 15-30) and modified reporter cell lines (all H9 background, passage 40-75) were maintained on VTN-N (Fisher Scientific) using Essential8 medium (E8) (Fisher Scientific) (Chen et al., 2011) and passaged twice a week using EDTA (Chen, 2008). Cells were tested for *mycoplasma* contamination once a month.

ESC Differentiation

Differentiation into neural ectoderm was performed as previously described (Chambers 2009) with slight modifications. Briefly, cells were plated at 250 000 cells/cm$^2$ on VTN-N coated dishes in E8+Y-27632 (Tocris). After 24 h (day0) medium was changed to Essential6 (E6) (Chen) supplemented with 10 μM SB431542 (Tocris Biosciences), 500 nM LDN193189 (Stem Cell Technologies) and 1 μM XAV939 (Tocris Biosciences) (until day 5). From day 5 on XAV939 was removed from the medium. Medium was changed every day until day 11.

Hypothalamic ectoderm differentiation was performed as described earlier (Maroof et al., 2013; Merkle et al., 2015) with slight modifications. Briefly, cells were plated at 250 000 cells/cm$^2$ on VTN-N coated dishes in E8+Y-27632. After 24 h (day0) medium was changed to E6 supplemented with 10 μM SB431542 for 2 days. From day 2 on E6 medium was supplemented with high concentrations of SHH (1 µg/ml) until day 11. For conditioned medium preparation cells were cultured for 24 h in E6 only and washed twice afterwards to remove potential SHH from the induction medium. On day 13 E6 only was added to the cells and conditioned for 24 h. Prior to using it, the conditioned medium was sterile filtered to get rid of debris and dead cells.

For lens differentiation cells were plated at 250 000 cells/cm$^2$ on VTN-N coated dishes in E8+10 µM Y-27632. After 24 h (day0) medium was changed to E6 supplemented with 10 µM SB431542 and 5 ng/ml BMP4 (R&D Systems). Medium was changed every day. On day 3 BMP4 was removed from the medium and cells were cultured in E6+10 µM SB431542 until day 15. From day 15 on cells were maintained in E6 only for up to 120 days. From day 30 on, medium was supplemented with VTN-N (1:100) once a week during feeding to prevent cells from peeling of the plate.

For pituitary differentiation cells were plated at 250 000 cells/cm$^2$ on VTN-N coated dishes (differentiation works best in 24 well plates) in E8+10 µM Y-27632. After 24 h (day0) medium was changed to E6 supplemented with 10 µM SB431542 and 5 ng/ml BMP4 (R&D Systems). Medium was changed every day. On day 3 BMP4 was removed from the medium and cells were cultured for 1 day in E6+10 µM SB431542. For the standard differentiation conditions, on day 4 E6 was supplemented with 10 µM SB431542, 200 ng/ml SHH (R&D Systems, C25II), 100 ng/ml FGF8b (R&D Systems) and 50 ng/ml FGF10 (Peprotech Inc.). For some experiments SHH was replaced by 1 µM purmorphamine (Stemgent) or 1 µM SAG (Stemcell Technologies). From now on medium volume was doubled and cells were feed every other day until day 15. On day 15 of differentiation SIX1 H2B::GFP$^+$ cells were sorted using a BDFACS Aria III cell sorter. Purified cells were then plated as droplets (50 000 cells/10 µl drop) in E6 supplemented with 10 µM Y-27632, 200 ng/ml SHH, 100 ng/ml FGF8b and 50 ng/ml FGF10 on polyornithine/laminin/fibronectin-coated plates. After 24 h medium was changed to E6 containing SHH, FGF8 and FGF10 until day 30. Medium was changed every other day. For some experiments pituitary induction was started slightly later (day 6) or cells were differentiated in medium conditioned by hypothalamic neuroectoderm from either day 4 or day 6 on. For the co-culture experiment SIX1 H2B::GFP positive cells were sorted on day 6 and 50 000 cells/cm$^2$ were plated directly on hypothalamic neuroectodermal cells in E6 only supplemented with 10 µM SB431542.

Pituitary Cell Maturation and Subtype Specification

For standard (unless mentioned otherwise in the text) pituitary maturation, medium on day 30 was changed to "E6 only" for additional 30 days. For patterning experiments (indicated in the text) E6 medium was supplemented with either high concentrations of FGF8 (100 ng/ml, dorsalize), high concentrations of BMP2 (20 ng/ml, ventralize) or intermediate concentrations of both (FGF8 50 ng/ml, BMP2 10 ng/ml).

RNA Extraction and Traditional Quantitative Real Time PCR

Total RNA was extracted from at least 3 independent experiments using the TRIzol (Fisher Scientific) reagent in combination with Phase-lock tubes (5Prime) according to the manufactures protocol. 1 µg of total RNA was reverse transcribed into cDNA using iScript (BioRad). For quantitative RT PCR we used the SSoFast EvaGreen Mix (BioRad) in combination with QuantiTect primer assays (Qiagen) on a BioRad CFX96 Thermal Cycler. All reactions were run according to the manufacturer's protocol. Gene expression was normalized to glyceraldehyde 3-phosphate dehydrogenase (GAPDH) and a control cell type (indicated in the Figures). Results are calculated using the ΔΔCt method (Livak and Schmittgen, 2001).

Single Cell Quantitative RT-PCR

For single cell PCR analysis cells were detached using Accutase. After filtering through a 40 µm cell strainer DAPI negative cells were sorted on a BDFACS Aria III machine, essentially cleaning up the cell preparation of debris and dead cells. Sorted cell suspension was adjusted to a concentration of 400 000 cells/ml. Single cells were captured using the Fluidigm C1 system according to the manufactures manual. Capture rate of for each C1 chip was confirmed microscopically using a standard tissue culture bright flied microscope. Capture rates were as follows: day 30: 91% (87/96) day 60: 94% (90/96) day 60 FGF8: 93% (89/96) day 60 FGF8/BMP2: 89% (85/96) day 60 BMP2: 93% (89/96). Cells were lysed, RNA was extracted and transcribed into cDNA using the C1 in combination with wet-lab tested Fluidigm DELTAgene assays (FIG. 27) following the manufactures protocol. Wet-lab tested DELTAgene assays were purchased directly from Fluidigm. The resulting cDNA was diluted 1:5 and subjected to Single cell PCR amplification using the Fluidigm BioMark system in combination with EvaGreen chemistry according to the manufactures manual ("Fast Gene Expression Analysis Using EvaGreen on the BioMark or BioMark HD System"). PCR was run using a Fluidigm 96.96 Dynamic Array. Each primer pair was run in technical duplicates on the chip. Only single cells with consistent amplification results between the technical primer replicates were considered to minimize false positive calls on the expense of increasing the number of false negatives. Overall discrepancy rate was low (>3% per primer pair). Expression data was analyzed using the Fluidigm Real-Time PCR analysis software in combination with the Fluidigm SINGuLAR Analysis Toolset for R (Version 3.0.2 (2013-09-25) "Frisbee Sailing").

Microscopy, Antibodies and Flow Cytometry

After washing the cells once with PBS, cells were fixed with 4% (v/v) paraformaldehyde for 20 min, washed twice with PBS, permeabilized using 0.1% (v/v) Triton X-100 in PBS, Cells were blocked with 10% (v/v) FCS in PBS for 1-5 h at room temperature. Cells were incubated with primary antibodies diluted in 2% FCS (v/v) in PBS at 4° C. overnight. A list of the primary antibodies used in this study is provided as FIG. 28. After primary antibody incubation cells were washed twice with PBS followed by incubation with appropriate AlexaFluor-conjugated secondary antibodies diluted in PBS at room temperature for 1 h (1:1000; Molecular Fisher Scientific). After washing twice with PBS nuclei were stained using DAPI. After and additional 2 washing steps, fluorescence images of the cells were taken using an Olympus IX71 inverted microscope equipped with a Hamamatsu ORCA CCD camera.

For immunohistochemical analysis, the animals were perfused with PBS and then 4% paraformaldehyde. Matrigel plugs were post-fixed in 4% paraformaldehyde and subsequently immersed in 30% sucrose. Matrigel plugs were cryosectioned at 30 µm for immunohistochemical analysis. The sections were pretreated with Antigen Retrieval Reagent-Universal solution (R&D systems). The sections were washed with PBS and then blocked with blocking solution (1% BSA-0.3% Triton-PBS) for 1 hour at room temperature. The sections were stained with hNA, Ki67, ACTH, GH, TSH, PRL, FSH and LH and subsequently with an Alexa-568 conjugated secondary antibody. The images were acquired using an Olympus BX51 Microscope equipped with a Hamamatsu camera. Stereological quantification of the number of ACTH cells in the whole matrigel plug was conducted using the optical fractionator probe, and the graft volume was analyzed using the Cavalieri estimator method. (Stereo Investigator Software, Microbrightfield Bioscience).

For Flow Cytometry analysis cells (different reporter cell lines) were detached from cell culture plastic using TrypLE (Fisher Scientific). After washing once with PBS cells were suspended in 2% FCS, 1 mM EDTA in PBS and DAPI. Cells were filtered using a 40 μm cell strainer and analyzed on BD LSRFortessa Flow Cytometer. Only single (doublet exclusion) live (DAPI−) cells were analyzed. Data was further processed using FlowJo Version 9.7.6 (FLOWJO LLC).

Cell Surface Marker Screen

For the BD Lyoplate™ cell surface marker screen day 30 cells were replated at a density of 100 000 cells/cm' into 96 well imaging plates using Accutase. After a 4 hour attachment phase cells were stained according to the user's manual for bioimaging. Cells were analyzed on an Operetta High Content Imaging System (Perkin Elmer). Images were processed and analyzed using the Harmony Software package (Perkin Elmer).

Stimulation of Hormone Release

To stimulate hormone release in vitro, cells were differentiated in 24 well plates as described above. On day 30 of differentiation cells were washed once with PBS and 2500 of fresh medium containing either the solvent or the stimulant were added to each well. After 12 h the supernatant was removed and centrifuged for 5 min at 2000 g to pellet debris. Supernatant was transferred into fresh reaction tubes, flash frozen and stored at −80° C. until ELISA measurements. Stimulants used were: CRF (Tocris, 1 μM), Stressin I (Tocris, 2 μM), Ghrelin (Tocris, 1 μM), Somatocrinin (Accurate Chemical, 1 μg/ml), Nafarelin (Tocris, 1 μM) and Urocortin (Tocris, 500 nM).

ELISA Measurements

Hormone concentration in the supernatant of cells or in animal serum was analyzed using ELISA measurements. Hormone concentration in the cell culture supernatant was assessed using traditional single hormone ELISA Kits according to the manufactures manual. ACTH (Calbiotech, detects rat and human ACTH), hGH (R&D Systems, human specific), FSH (Calbiotech, FSH (lumELISA, human specific) and corticosterone (Abcam). Plates were read using an EnSpire Multimode plate reader (PerkinElmer). Hormone concentration in in vivo samples was analyzed using either traditional ELISA (for ACTH only, serum diluted 1:2) or species specific (human or rat) Milliplex multiplex ELISA using Luminex technology (Millipore). Magnetic bead-based sandwich immunoassay was performed according to the manufactures manual. 250 μl of undiluted serum samples in duplicate wells were analyzed by Luminex FlexMap 3D (Luminex Corp, Austin, Tex.). Cytokine concentrations were determined by Luminex Xponent 4.1 and EMD-Millipore Milliplex Analyst v5.1 using 5-p log analysis.

Grafting of Cells into Hypophysectomized Rats, Sample Preparation

Male Athymic nude rats (RNU rat Crl:NII-1-Foxn1rnu, Charles River Laboratories) were hypophysectomized using the parapharyngeal approach at the age of 8 weeks. Plasma ACTH was measured 1 week after hypophysectomy to confirm hypopituitarism. The hypophysectomized rats were randomized into two groups: Sham control (n=4), Human ES derived pituitary cells subcutaneously grafted group (n=7). Syringes (1 ml, BD biosciences) and matrigel (BD biosciences) were chilled on ice prior to injection to prevent gel forming of matrigel before injection. The neck of rat was shaved and prepared with Betadine and 70% Ethanol. 0.9 ml Matrigel was mixed with a 2 million human pituitary cell suspension (in 1000 essential E6 medium). The mixture of matrigel and cells was injected into subcutaneous tissue on the neck of rats.

Blood was taken by retro orbital bleeding before graft, 1 week, 3 weeks, 5 weeks and 7 weeks after the transplantation under isoflurane anesthesia at 8 a.m. Blood was collected with K2 EDTA-treated BD Microtainer MAP (BD Biosciences) and plasma was isolated and stored at −80° C.

Seven weeks after grafting, the animals were anesthetized (Fatal Plus, 60 mg/kg) and intracardially perfused with 0.1M phosphate buffered saline (PBS, pH 7.4) and then 4% paraformaldehyde (in 0.1M PBS, pH7.4). Matrigel plugs were excised and post-fixed in 4% paraformaldehyde for 6 hours and subsequently immersed in 30% sucrose for 24 hours at 4° C., then frozen in embedding compound (OCT, Tissue-Tek, Sakura Finetek USA, Inc.). Matrigel plugs were cryosectioned at 30 μm for immunohistochemical analysis. The sections were stained with ACTH, GH, TSH, PRL, FSH and LH (rabbit IgG, 1:100, the National Hormone and Peptide Program) and subsequently with Alexa 568 conjugated goat anti-rabbit (life technologies). The images were taken by a Hamamatsu camera and an Olympus BX51 Microscope. Stereological quantification of the number of ACTH cells in the whole matrigel plug was conducted using the optical fractionator probe, and the graft volume was analyzed using the cavalieri estimator method (Stereo Investigator Software, Microbrightfield Bioscience).

Statistical Analysis

Data are presented as sample means±SEM, as indicated in each figure legend. Means represent the data of independent experiments (number indicated in the corresponding figure legend). Differences between groups were analyzed by unpaired t tests or one-way ANOVA with Bonferroni multiple-comparison post hoc test. $p<0.05=*$, $p<0.01=$, $p<0.001=*$, $p<0.0001=****$

REFERENCES

1. Bailey, A. P., Bhattacharyya, S., Bronner-Fraser, M., and Streit, A. (2006). Lens specification is the ground state of all sensory placodes, from which FGF promotes olfactory identity. Developmental cell 11, 505-517.
2. Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nature biotechnology 27, 275-280.
3. Chambers, S. M., Qi, Y., Mica, Y., Lee, G., Zhang, X. J., Niu, L., Bilsland, J., Cao, L., Stevens, E., Whiting, P., et al. (2012). Combined small-molecule inhibition accelerates developmental timing and converts human pluripotent stem cells into nociceptors. Nature biotechnology 30, 715-720.
4. Chemaitilly, W., and Sklar, C. A. (2010). Endocrine complications in long-term survivors of childhood cancers. Endocrine-related cancer 17, R141-159.
5. Chen, G. (2008). Splitting hESC/hiPSC lines with EDTA in feeder free conditions. In StemBook (Cambridge (Mass.)).
6. Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Chemically defined conditions for human iPSC derivation and culture. Nat Methods 8, 424-429.

7. Dincer, Z., Piao, J., Niu, L., Ganat, Y., Kriks, S., Zimmer, B., Shi, S. H., Tabar, V., and Studer, L. (2013). Specification of functional cranial placode derivatives from human pluripotent stem cells. Cell reports 5, 1387-1402.

8. Dreser, N., Zimmer, B., Dietz, C., Sugis, E., Pallocca, G., Nyffeler, J., Meisig, J., Bluthgen, N., Berthold, M. R., Waldmann, T., et al. (2015). Grouping of histone deacetylase inhibitors and other toxicants disturbing neural crest migration by transcriptional profiling. Neurotoxicology 50, 56-70.

9. Ezzat, S., Asa, S. L., Couldwell, W. T., Barr, C. E., Dodge, W. E., Vance, M. L., and McCutcheon, I. E. (2004). The prevalence of pituitary adenomas: a systematic review. Cancer 101, 613-619.

10. Lamolet, B., Pulichino, A. M., Lamonerie, T., Gauthier, Y., Brue, T., Enjalbert, A., and Drouin, J. (2001). A pituitary cell-restricted T box factor, Tpit, activates POMC transcription in cooperation with Pitx homeoproteins. Cell 104, 849-859.

11. Lee, G., Ramirez, C. N., Kim, H., Zeltner, N., Liu, B., Radu, C., Bhinder, B., Kim, Y. J., Choi, I. Y., Mukherjee-Clavin, B., et al. (2012). Large-scale screening using familial dysautonomia induced pluripotent stem cells identifies compounds that rescue IKBKAP expression. Nature biotechnology 30, 1244-1248.

12. Leung, A. W., Kent Morest, D., and Li, J. Y. (2013). Differential BMP signaling controls formation and differentiation of multipotent preplacodal ectoderm progenitors from human embryonic stem cells. Developmental biology 379, 208-220.

13. Livak, K. J., and Schmittgen, T. D. (2001). Analysis of relative gene expression data using real-time quantitative PCR and the 2(-Delta Delta C(T)) Method. Methods 25, 402-408.

14. Maroof, A. M., Keros, S., Tyson, J. A., Ying, S. W., Ganat, Y. M., Merkle, F. T., Liu, B., Goulburn, A., Stanley, E. G., Elefanty, A. G., et al. (2013). Directed differentiation and functional maturation of cortical interneurons from human embryonic stem cells. Cell stem cell 12, 559-572.

15. Merkle, F. T., Maroof, A., Wataya, T., Sasai, Y., Studer, L., Eggan, K., and Schier, A. F. (2015). Generation of neuropeptidergic hypothalamic neurons from human pluripotent stem cells. Development 142, 633-643.

16. Mica, Y., Lee, G., Chambers, S. M., Tomishima, M. J., and Studer, L. (2013). Modeling neural crest induction, melanocyte specification, and disease-related pigmentation defects in hESCs and patient-specific iPSCs. Cell reports 3, 1140-1152.

17. Murry, C. E., and Keller, G. (2008). Differentiation of embryonic stem cells to clinically relevant populations: lessons from embryonic development. Cell 132, 661-680.

18. Nunez, L., Villalobos, C., Senovilla, L., and Garcia-Sancho, J. (2003). Multifunctional cells of mouse anterior pituitary reveal a striking sexual dimorphism. The Journal of physiology 549, 835-843.

19. Regal, M., Paramo, C., Sierra, S. M., and Garcia-Mayor, R. V. (2001). Prevalence and incidence of hypopituitarism in an adult Caucasian population in northwestern Spain. Clinical endocrinology 55, 735-740.

20. Rivera, J. A. (2006). Lymphocytic hypophysitis: disease spectrum and approach to diagnosis and therapy. Pituitary 9, 35-45.

21. Rosenfeld, M. G., Briata, P., Dasen, J., Gleiberman, A. S., Kioussi, C., Lin, C., O'Connell, S. M., Ryan, A., Szeto, D. P., and Treier, M. (2000). Multistep signaling and transcriptional requirements for pituitary organogenesis in vivo. Recent progress in hormone research 55, 1-13; discussion 13-14.

22. Sklar, C. A., and Constine, L. S. (1995). Chronic neuroendocrinological sequelae of radiation therapy. International journal of radiation oncology, biology, physics 31, 1113-1121.

23. Smith, J. C. (2004). Hormone replacement therapy in hypopituitarism. Expert opinion on pharmacotherapy 5, 1023-1031.

24. Smith, S. M., and Vale, W. W. (2006). The role of the hypothalamic-pituitary-adrenal axis in neuroendocrine responses to stress. Dialogues Clin Neurosci 8, 383-395.

25. Steinbeck, J. A., Jaiswal, M. K., Calder, E. L., Kishinevsky, S., Weishaupt, A., Toyka, K. V., Goldstein, P. A., and Studer, L. (2015). Functional Connectivity under Optogenetic Control Allows Modeling of Human Neuromuscular Disease. Cell stem cell.

26. Suga, H., Kadoshima, T., Minaguchi, M., Ohgushi, M., Soen, M., Nakano, T., Takata, N., Wataya, T., Muguruma, K., Miyoshi, H., et al. (2011). Self-formation of functional adenohypophysis in three-dimensional culture. Nature 480, 57-62.

27. Szarek, E., Farrand, K., McMillen, I. C., Young, I. R., Houghton, D., and Schwartz, J. (2008). Hypothalamic input is required for development of normal numbers of thyrotrophs and gonadotrophs, but not other anterior pituitary cells in late gestation sheep. The Journal of physiology 586, 1185-1194.

28. Tabar, V. (2011). Making a pituitary gland in a dish. Cell stem cell 9, 490-491.

29. van Gelderen, H. H., and van der Hoog, C. E. (1981). Familial isolated growth hormone deficiency. Clinical genetics 20, 173-175.

30. Villalobos, C., Nunez, L., and Garcia-Sancho, J. (2004). Phenotypic characterization of multi-functional somatotropes, mammotropes and gonadotropes of the mouse anterior pituitary. Pflugers Archiv: European journal of physiology 449, 257-264.

31. Wand, G. (2008). The influence of stress on the transition from drug use to addiction. Alcohol Res Health 31, 119-136.

32. Webster, J. I., and Sternberg, E. M. (2004). Role of the hypothalamic-pituitary-adrenal axis, glucocorticoids and glucocorticoid receptors in toxic sequelae of exposure to bacterial and viral products. J Endocrinol 181, 207-221.

33. Zhu, X., Gleiberman, A. S., and Rosenfeld, M. G. (2007). Molecular physiology of pituitary development: signaling and transcriptional networks. Physiol Rev 87, 933-963.

34. Zimmer, B., Lee, G., Balmer, N. V., Meganathan, K., Sachinidis, A., Studer, L., and Leist, M. (2012). Evaluation of developmental toxicants and signaling pathways in a functional test based on the migration of human neural crest cells. Environ Health Perspect 120, 1116-1122.

6.3 Example 3: Derivation of Neural Crest from Pluripotent Stem Cells

Pluripotent stem cells were cultured in E8/E6 media to differentiate into neural crest progenitor cells. Spontaneous differentiation of these neural crest progenitor cells generated both autonomic neurons, marked by MASH1 expression, and sensory neurons, marked by ISL1 and/or BRN3a expression.

Pluripotent stem cells were differentiated in E8/E6 media as described by Example 1, and as shown by FIG. 29A. In particular, the pluripotent stem cells were differentiated in E6 media supplemented with SB431542, BMP4 and CHIR99021 for two days (i.e., from d0 to d2 of culture in E6 media). At d2, BMP4 was removed from the culture media, and the cells were cultured in E6 media supplemented with SB431542 and CHIR99021 for culture days d2 to d11. At day 11, cells were FACS sorted for cells expressing CD49d and Sox10, and further cultured in neural crest differentiation media. At d15, spheroids from the culture were selected and replated, which were again replated at d18. At d25, the sorted neural crest cells expressed MASH1 and ISL1 (FIG. 29B).

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. An in vitro method for inducing differentiation of stem cells, comprising contacting stem cells with at least one inhibitor of transforming growth factor beta (TGFβ)/Activin-Nodal signaling and at least one activator of bone morphogenetic protein (BMP) signaling for at least about 2 days, and contacting said cells with
- at least one activator of wingless (Wnt) signaling
  to obtain a population of differentiated cells that express at least one neural crest lineage marker.

2. The method of claim 1, wherein said stem cells are contacted with said at least one inhibitor of TGFβ/Activin-Nodal signaling for at least about 12 days.

3. The method of claim 1, wherein said stem cells are contacted with said at least one inhibitor of TGFβ/Activin-Nodal signaling and said at least one activator of BMP signaling concurrently.

4. The method of claim 1, wherein said stem cells are contacted with said at least one inhibitor of TGFβ/Activin-Nodal signaling and said at least one activator of Wnt signaling concurrently.

5. The method of claim 1, wherein said stem cells are differentiated to said differentiated cells that express said at least one neural crest lineage marker on or after about 12 days from the initial contact of the stem cells with said at least one inhibitor of TGFβ/Activin-Nodal signaling.

6. The method of claim 1, wherein said at least one inhibitor of TGFβ/Activin-Nodal signaling is selected from the group consisting of SB431542, derivatives thereof, and combinations thereof.

7. The method of claim 1, wherein said at least one activator of Wnt signaling lowers glycogen synthase kinase 3β(GSK3β) for activation of Wnt signaling.

8. The method of claim 1, wherein said at least one activator of Wnt signaling is selected from the group consisting of CHIR99021, WNT3A, derivatives thereof, and combinations thereof.

9. The method of claim 1, wherein said at least one neural crest lineage marker comprises SOX10.

10. The method of claim 1, wherein said stem cells are selected from the group consisting of human embryonic stem cells, human induced pluripotent stem cells, human parthenogenetic stem cells, primordial germ cell-like pluripotent stem cells, epiblast stem cells, and F-class pluripotent stem cells.

* * * * *